United States Patent
Olson et al.

(10) Patent No.: US 11,774,457 B2
(45) Date of Patent: Oct. 3, 2023

(54) IDENTIFICATION AND ANALYSIS OF PROTEIN BIOMARKERS

(71) Applicant: Wright State University, Dayton, OH (US)

(72) Inventors: James Edwin Olson, Freeport, ME (US); April Daubenspeck, Fairborn, OH (US); David Cool, Fairborn, OH (US); Bryan Ludwig, Oakwood, OH (US)

(73) Assignee: Wright State University, Dayton, OH (US)

( * ) Notice: Subject to any disclaimer, the term of this patent is extended or adjusted under 35 U.S.C. 154(b) by 137 days.

(21) Appl. No.: 16/506,639

(22) Filed: Jul. 9, 2019

(65) Prior Publication Data

US 2020/0011880 A1 Jan. 9, 2020

Related U.S. Application Data

(60) Provisional application No. 62/695,504, filed on Jul. 9, 2018.

(51) Int. Cl.
*G01N 33/68* (2006.01)

(52) U.S. Cl.
CPC . *G01N 33/6893* (2013.01); *G01N 2800/2871* (2013.01); *G01N 2800/52* (2013.01); *G01N 2800/56* (2013.01); *G01N 2800/60* (2013.01)

(58) Field of Classification Search
None
See application file for complete search history.

(56) References Cited

U.S. PATENT DOCUMENTS

2015/0276763 A1* 10/2015 Garcia-Berrocoso ........... G01N 33/6893
506/9

OTHER PUBLICATIONS

Chen H-J, Shen Y-C, Shiao Y-J, Liou K-T, Hsu W-H, Hsieh P-H, et al. (2015) Multiplex Brain Proteomic Analysis Revealed the Molecular Therapeutic Effects of Buyang Huanwu Decoction on Cerebral Ischemic Stroke Mice. PLoS ONE 10(10): e0140823. https://doi.org/10.1371/journal.pone.0140823 (Year: 2015).*
Daubenspeck, April "Proteomic Analysis of Ischemic Stroke Blood Biomarkers." Electronic Thesis or Dissertation. Wright State University, 2017. https://etd.ohiolink.edu/ (Year: 2017).*
Program: Biomedical Sciences, PhD—Wright State University https://catalog.wright.edu/preview_program.php?catoid=20&poid=16519&hl=dissertation&returnto=search Downloaded Mar. 10, 2023 (Year: 2023).*
Breiman, Leo "Random Forests" Machine Learning, 45, p. 5-32, 2001, Kluwer Academic Publishers.

* cited by examiner

*Primary Examiner* — Aurora M Fontainhas
(74) *Attorney, Agent, or Firm* — McNees Wallace & Nurick LLC

(57) ABSTRACT

Protein biomarkers may be used to rapidly and accurately diagnose stroke. Biomarkers may be utilized in a rapid and inexpensive test that could be used at the bedside or ambulatory setting to definitively indicate the presence or absence of stroke and its severity. Such a test would quickly stratify patients in need of immediate stroke treatment from those who are not having a stroke. The test may aid emergency personnel in the decision for the most appropriate treatment plan and treatment location, thereby minimizing morbidity and mortality of stroke patients.

9 Claims, 60 Drawing Sheets

FIG 5 /IMAGE INTENSITY (ARBITRARY UNIT)

IDENTIFICATION AND ANALYSIS OF PROTEIN BIOMARKERS

PRIORITY

The present Patent Application claims priority to and benefit of U.S. Provisional Patent Application No. 62/695,504, filed Jul. 9, 2018, entitled "IDENTIFICATION AND ANALYSIS OF PROTEIN BIOMARKERS," which is hereby incorporated by reference in its entirety.

TECHNICAL FIELD

The innovation relates to blood biomarkers that can be used to identify patients suffering from a stroke.

BACKGROUND

Stroke is a major worldwide public health concern, second only to heart disease as the leading cause of mortality. According to the American Heart Association's 2016 statistical update, stroke is the fifth leading cause of death in the United States with a fatal stroke occurring approximately every 4 minutes. Stroke also is the leading cause of serious long-term disability, resulting in an annual direct cost of $17.2 billion in the United States alone. Given this high morbidity and its economic impact, numerous public health measures are underway to decrease the incidence of this preventable disease.

Although many of the gross effects of stroke are similar, stroke is considered a multifactorial disease due to the various mechanisms by which it develops. Stroke can result from blockage in a cerebral artery supplying brain tissue (ischemic stroke) or from a rupture of an artery with resulting extravasation of blood into the brain parenchyma or meningeal spaces (hemorrhagic stroke). In the case of transient ischemic attacks (TIA)—sometimes referred to as mini-strokes—there is a disruption of blood flow that does not cause an infarction and also self-resolves within 24 hours. Ischemic stroke accounts for 87% of all strokes and typically occurs when a blood clot occludes a vessel. During an ischemic stroke, approximately 1.9 million neurons and 14 billion synapses die every minute—the equivalent of aging 3.6 years each hour. The amount of time the brain experiences ischemic conditions therefore crucially influences patient outcome.

Reperfusion of the ischemic brain within the shortest time interval is a primary goal of emergency health care providers. Currently two treatment options are available for reperfusion of the ischemic, non-hemorrhagic, brain tissue: thrombolytic therapy and mechanical thrombectomy. Thrombolytic therapy dissolves the clot using a specific enzyme cocktail injected into the blood vessel near the site of the blockage. This ultimately results in the clot being digested by the enzyme. Conversely, during a thrombectomy procedure, the occluding blood clot is removed via an intravascular catheter positioned under fluoroscopic guidance. While the current gold standard of treatment for ischemic stroke is thrombolytic therapy using tissue plasminogen activator (tPA), recent studies have shown equivalent outcomes for patients receiving thrombectomy. The caveat is that whichever treatment is used, it must be started within a short time span of symptom onset to achieve maximal effectiveness—currently 4.5 hours for tPA and 6-8 hours for mechanical thrombectomy.

The risk of morbidity and mortality following stroke decreases when earlier diagnosis and treatment are achieved. Stroke patients who present to the emergency room within 3 hours of their first symptoms experience less disability at 3 months compared to those who receive delayed care. Public education of symptom recognition and the need to promptly seek medical attention is aimed at increasing the number of patients who arrive at the hospital before significant brain damage has occurred. However, once patients seek medical help, the time to diagnosis is the next critical step for obtaining definitive treatment. Quality metrics for hospitals treating patients with acute stroke include time intervals of less than 25 min from arrival to CT scan and 60 min from arrival to definitive treatment. To achieve these metrics, rapid diagnosis and treatment decisions are necessary.

It is estimated that between 15,000 and 165,000 cerebrovascular events are misdiagnosed annually in the US. This translates to a significant portion of stroke victims who present to the emergency department in the early stages of the disorder being sent home without receiving proper treatment. In addition, the rate of stroke over-diagnosis is estimated at 19-31%, exposing patients to significant risks from thrombolysis or thrombectomy procedures with no treatment benefit for their actual underlying condition.

When a patient presents to the emergency department with stroke-like symptoms, a number of conditions must be ruled out before a diagnosis of stroke can be made. Conditions that mimic stroke are diverse and include seizure, systemic infection, syncope, hypoglycemia, tumor, vertigo, migraine, and dementia. While clinicians are performing various tests to rule out these conditions, damage to the ischemic brain is progressing. Currently, clinical examination and medical imaging are used to diagnose stroke. However, there are a number of drawbacks to these strategies including low diagnostic accuracy and lengthy time requirements.

The National Institutes of Health Stroke Scale score (NIHSS) is a standardized assessment tool for the diagnosis of the disease. It scores clinical symptoms such as level of consciousness, limb drift, facial palsy, and speaking ability. The scale ranges from 0 to 42, with the higher severity associated with higher scores. It is most useful for large artery, anterior circulation strokes because they commonly exhibit the symptoms assessed by the tool. However, complex stroke syndromes and posterior circulation strokes could actually end up with an NIHSS score of 0, leading to a missed diagnosis because the symptoms exhibited by the patient were limited to headache, nausea, vomiting, and dizziness—symptoms which are not evaluated by the NIHSS. The accuracy of stroke screening tools is low and variable with sensitivities ranging between 82% and 93% and specificities between 74% and 99%. The diagnostic sensitivity of EMS first responders is 50%, while that of emergency physicians is 92%. The reliability of the diagnosis also decreases with less experienced or less confident examiners.

When stroke is suspected via clinical examination, the next step is neuroimaging. This approach is often used to distinguish between hemorrhagic stroke and ischemic stroke and rule out certain stroke mimics. CT scans can be performed rapidly, but have low accuracy for identifying ischemic stroke (sensitivity=26% to 39% and specificity=52% to 100%). While CT scans can reveal bleeding in the brain, they are not able to image acute infarction. MRI scans—although much more accurate in detecting acute infarction—are more time consuming, less cost effective, and not widely available in emergency departments. Additionally, there is a subset of patients who are ineligible to be scanned by MRI such as those with implanted pacemaker devices or those with claustrophobia.

Decreasing the time it takes to diagnose a stroke patient leads to quicker treatment times and therefore less likelihood of disability. But to achieve this, the patient must arrive at the hospital within the treatment time limits. Many efforts are underway to decrease the triage time of stroke patients. Examples of this include the prioritization of transporting patients to hospitals with stroke expertise, pre-notification of incoming stroke patient by EMS to hospitals, and telemedicine from smaller hospitals to stroke centers. Having a point-of-care laboratory in the hospital is also shown to decrease the door-to-therapy time by half. The mobile stroke unit (MSU) is another such approach. Instead of transporting a patient to the most convenient hospital, the MSU—which is equipped with CT imaging, point-of-care lab, telemedicine capabilities, and treatment drugs—is designed to diagnose and treat at the site of the emergency. Appropriate triage of patients would decrease time to treatment, especially for those patients with large vessel occlusion who would benefit from endovascular therapy such as mechanical thrombectomy. When directly transported to a stroke center where patients can receive such treatment, a time-consuming secondary transport from the primary hospital to the comprehensive stroke center is avoided.

Multiple pre-hospital assessment tools have been developed for the appropriate triaging of patients by dispatchers and EMTs. The ROSIER scale (Recognition of Stroke in the Emergency Room) and the DIASE (Dispatcher Identification Algorithm of Stroke Emergency) are two such instruments. The first scale has a sensitivity of 93% and specificity of 83% while the later has a sensitivity of 53% and specificity of 97%. The number of stroke patients potentially missed using these tools leaves room for vast improvement.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

Cerebrovascular disease is one of the top causes of mortality and morbidity. Because of this, it is important to continue efforts in diagnosing and treating the disease. A rapid diagnostic blood test has yet to be developed and adopted into hospital processes, despite the potential for it to decrease time to treatment. Numerous blood protein biomarkers have been identified, but to date, none have proven clinically useful.

According to an aspect, the innovation provides a system to differentiate stroke from non-stroke patients via blood biomarkers.

In one embodiment, the innovation provides a system and a method to identify and evaluate novel blood protein biomarker(s) to diagnose stroke. In one embodiment, the method includes using serum from ischemic stroke patients. In one embodiment, the method to identify includes using proteomic and statistical techniques to investigate the differential abundance of proteins in the blood of stroke and non-stroke groups. According to an example, biomarker discovery techniques focused on 2D gel analysis and statistical exploration of SOMAscan assay results. A number of biomarker candidates, including biomarker panels, for ischemic stroke diagnosis, were identified.

In one example, high-abundance serum proteins were found to be differentially expressed between the ischemic brain of stroke patients undergoing mechanical thrombectomy and the same patient's circulating arterial blood. Albumin, transferrin, and immunoglobulin gamma protein spots were significantly higher in the circulating blood, and hemoglobin had a large fold change in abundance in the ischemic blood of a few patients. Further analysis of these individual proteins in a new cohort of patients suggested a lower diagnostic accuracy for these protein biomarkers.

A comparison of the venous blood of stroke patients to that of two non-stroke groups identified thirteen serum proteins that can differentiate stroke patients from healthy individuals. Further analysis of these thirteen individual proteins in stroke patients compared to stroke-mimicking patients suggested a lower diagnostic accuracy for these protein biomarkers.

Biomarkers were evaluated in a comparison of stroke patients to stroke mimicking patients, evaluating previously published biomarkers as well as exploring for new biomarker candidates. Here 27 additional proteins were identified that were significantly different between stroke and stroke-mimicking patient groups. These proteins, as single diagnostic biomarkers, were unlikely to be clinically useful. However, stroke biomarker panels show great promise. Random Forest Analysis identified a combination of proteins to distinguish stroke patients from TIA patients and non-TIA stroke-mimicking patients that may be clinically useful.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1A:
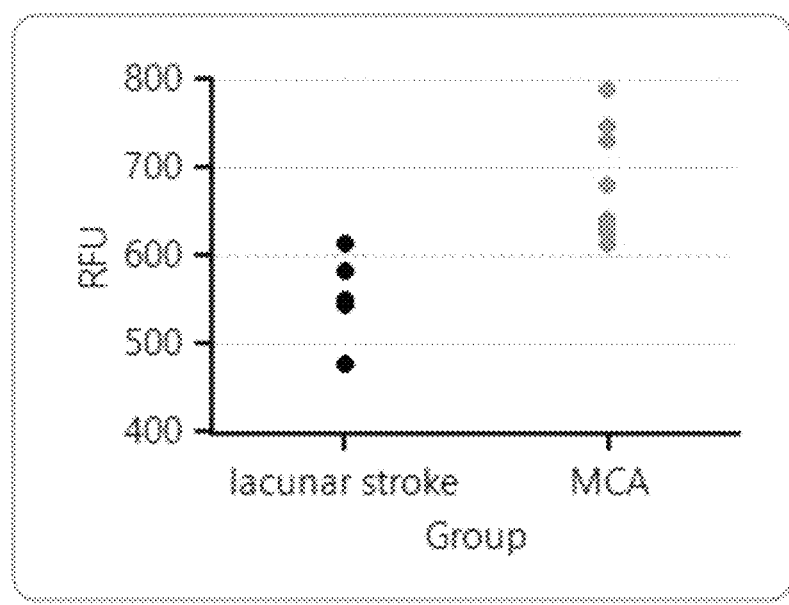
FIG. 1A depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1B:
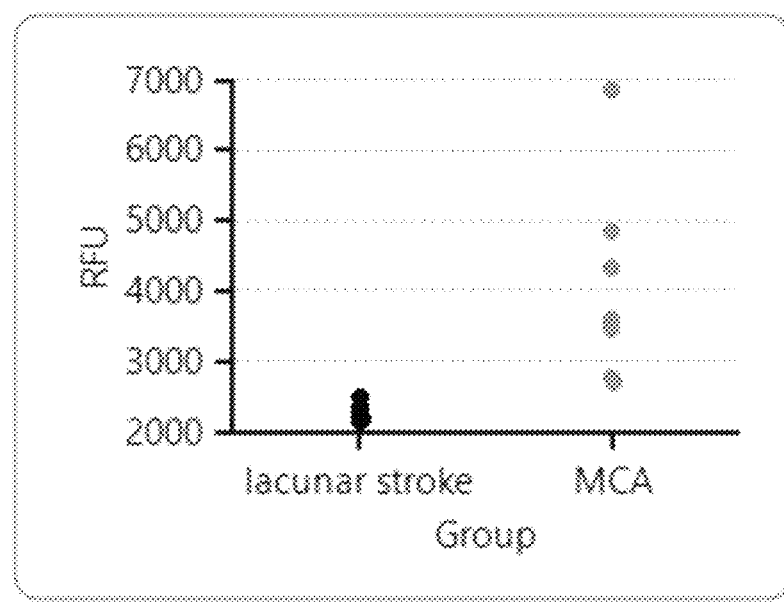
FIG. 1B depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1C:
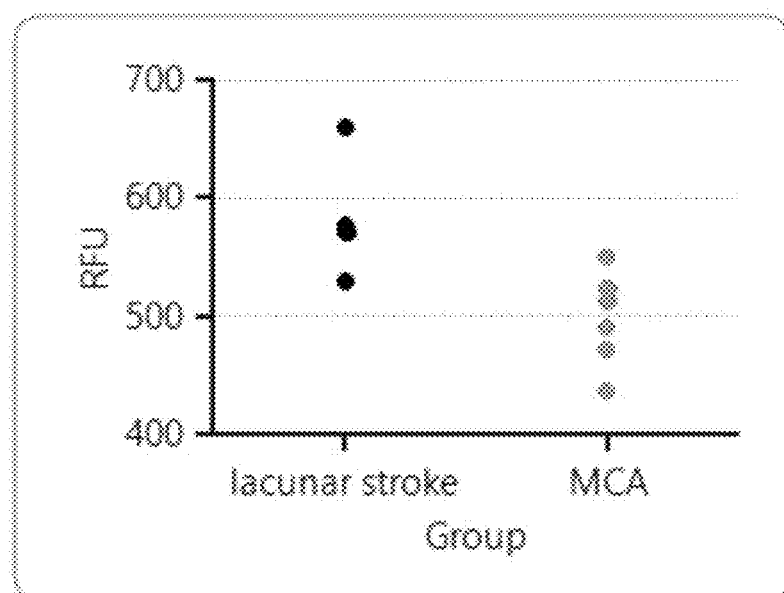
FIG. 1C depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1D:
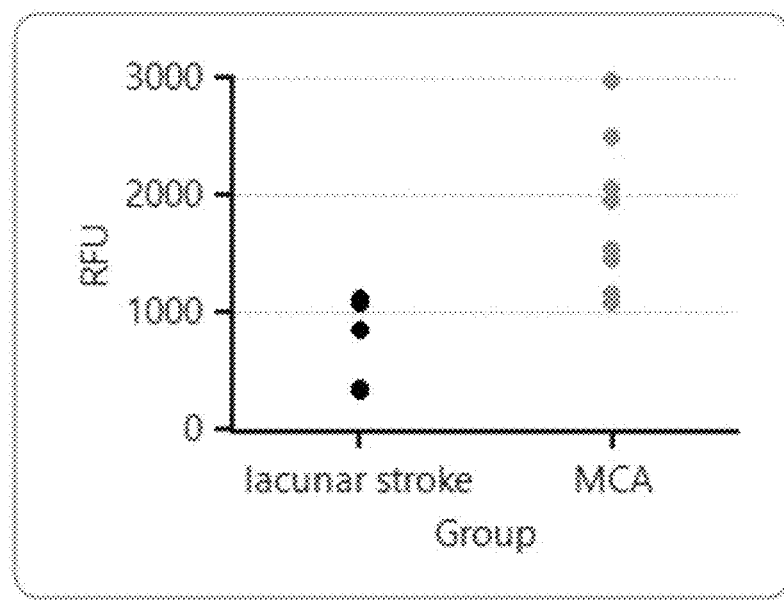
FIG. 1D depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1E:
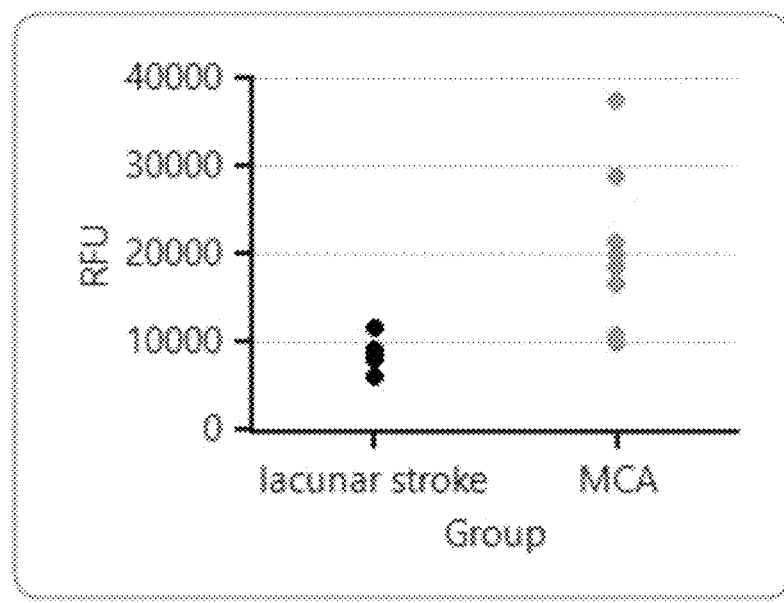
FIG. 1E depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1F:
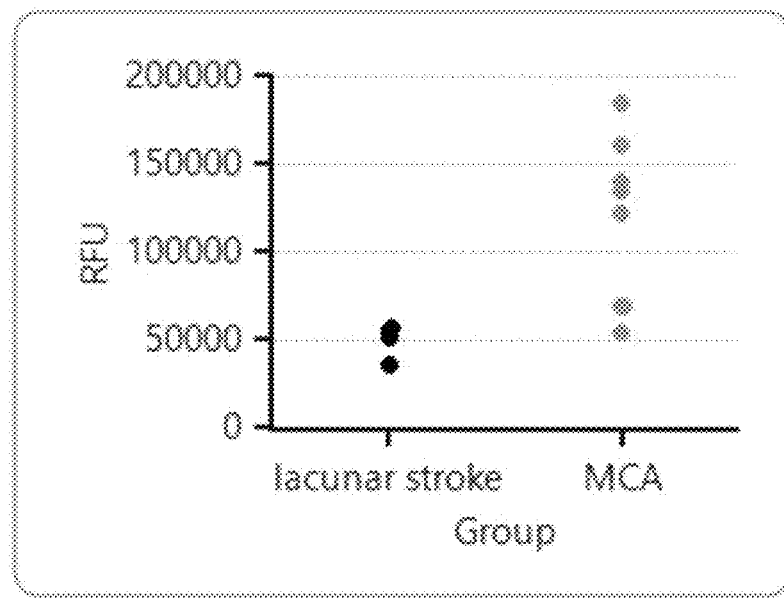
FIG. 1F depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1G:
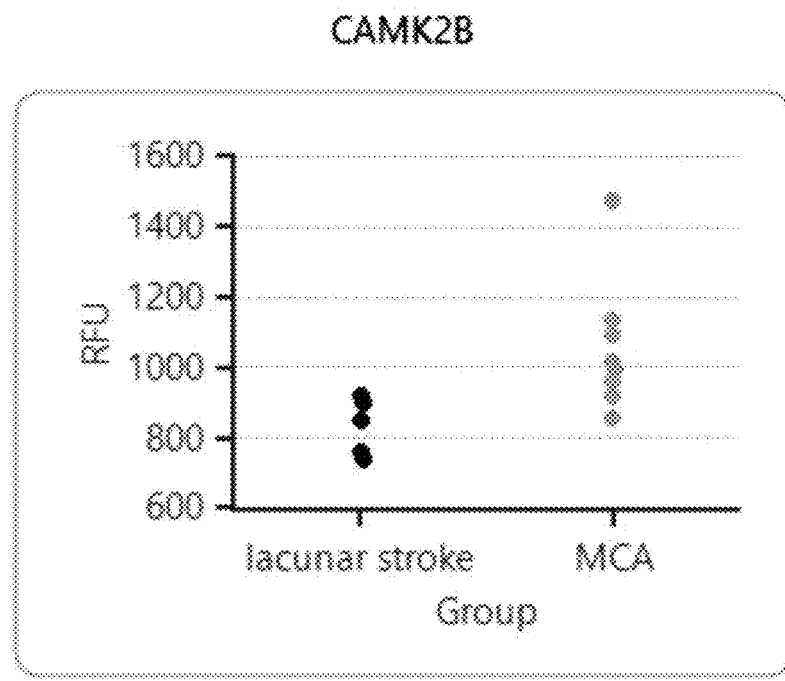
FIG. 1G depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1H:
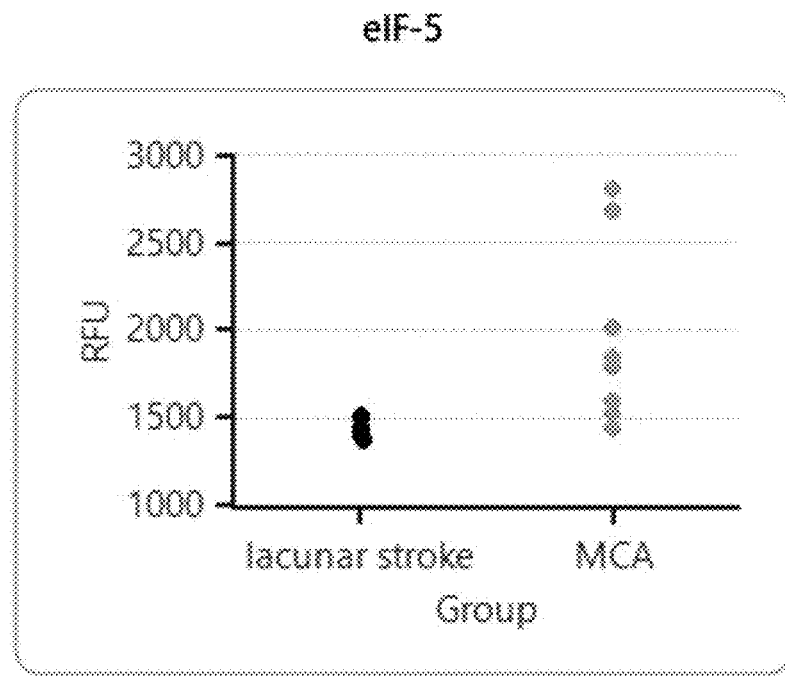
FIG. 1H depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1I:
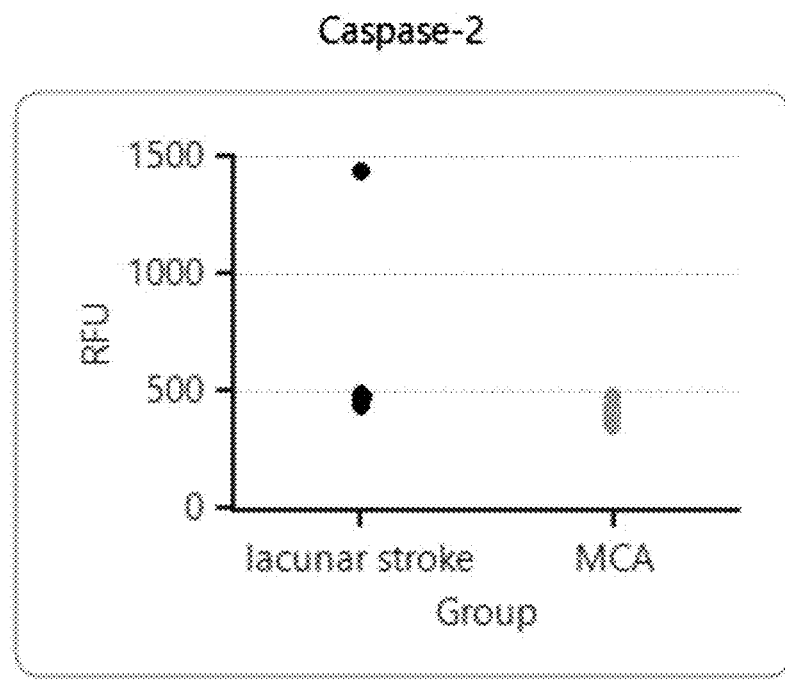
FIG. 1I depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1J:
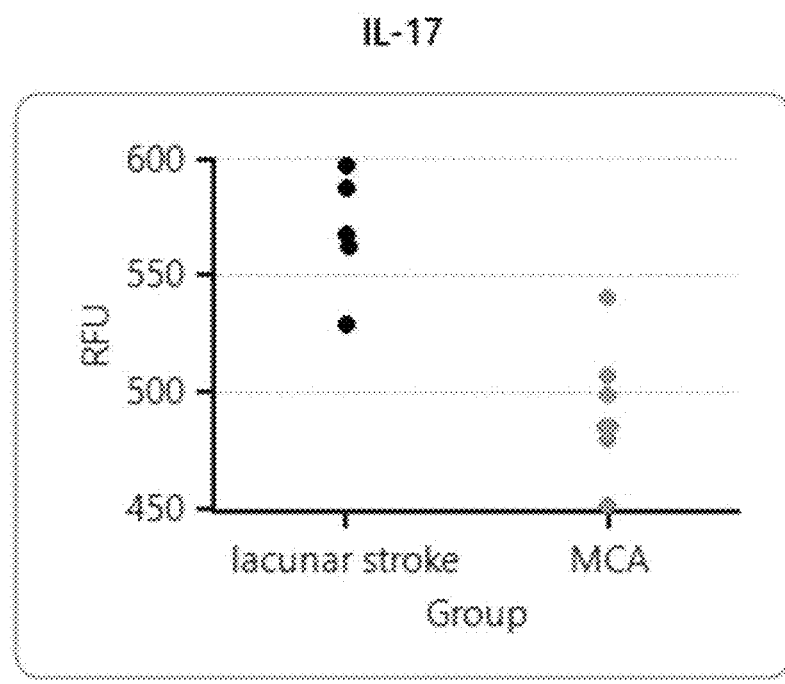
FIG. 1J depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1K:
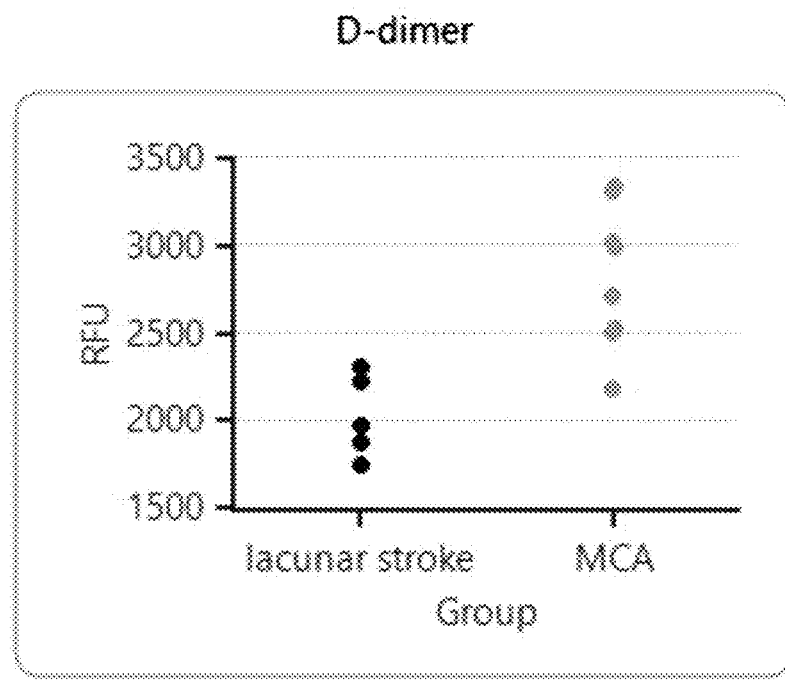
FIG. 1K depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1L:
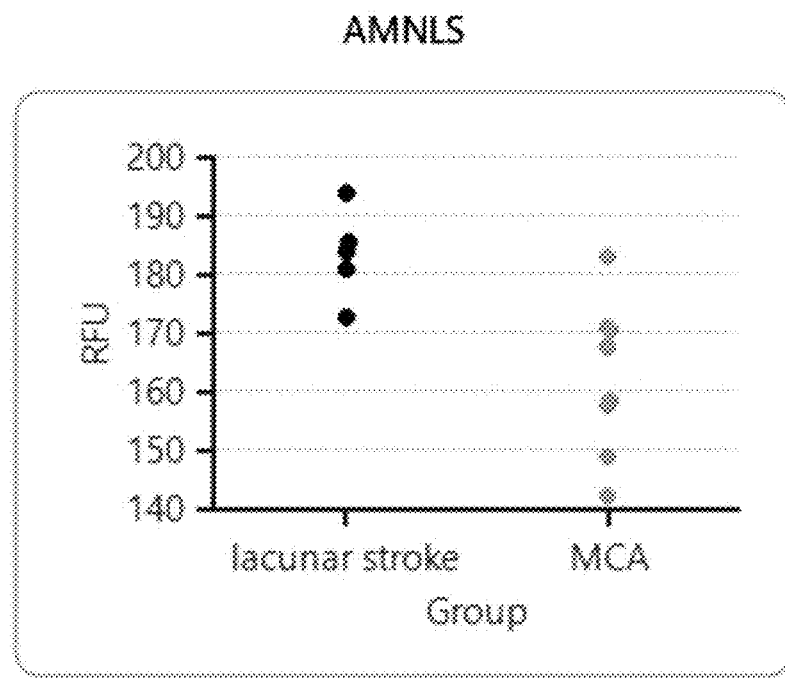
FIG. 1L depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.
Figure 1M:
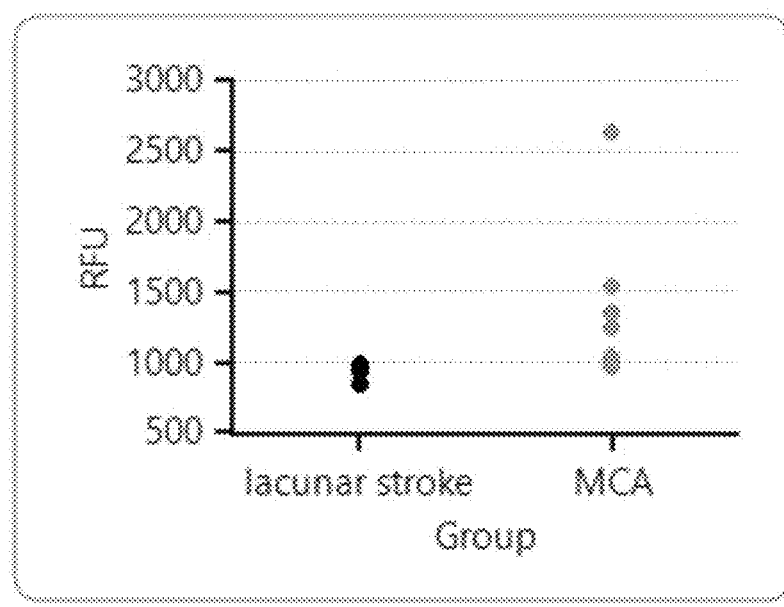
FIG. 1M depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation. A diagnostic biomarker that would indicate the presence of stroke, the time of onset, and the type, location and magnitude of injury would be useful to guide treatment for each stroke patient.

According to an aspect, the innovation provides a rapid and accurate test to diagnose stroke. In one embodiment, biomarkers may be used to rapidly and accurately diagnose stroke. In one embodiment, the biomarkers may be utilized in a rapid and inexpensive test that could be used at the bedside or ambulatory setting to definitively indicate the presence or absence of stroke and its severity. Such a test would quickly stratify patients in need of immediate stroke treatment from those who are not having a stroke. The test may aid emergency personnel in the decision for the most appropriate treatment plan and treatment location, thereby minimizing morbidity and mortality of stroke patients. Furthermore, it would help reduce costs for further stroke work-up in non-stroke patients.

Biomarkers are defined as characteristics that can be objectively measured and evaluated as an indicator of normal biological processes, pathogenic processes, or pharmacologic responses to therapeutic interventions. Common clinical biomarkers include blood pressure and blood glucose levels. For stroke, the NIHSS score, other pre-hospital assessment tools mentioned above, and neuroimaging are all considered biomarkers. In other diseases, common biomarkers are often molecules found in blood or other tissues. For example, patients with tumors are tested for cancer-specific antigens in the biopsied tissue. Patients with suspected heart attack are tested for blood troponin levels to indicate myocardial infarction.

According to an aspect, the innovation provides a test to detect and/or quantify protein biomarkers in the blood of a patient suspected of having or having had a stroke. Using blood and probing for proteins has marked advantages for point-of-care diagnostics, including speed. In one embodiment, the test may include an antigen-based protein detection device designed to minimize the time needed for clinical diagnosis.

There has been considerable effort to find a single biomarker for ischemic stroke by targeting the analysis on specific proteins or other substances which are only expressed in brain tissue. Peripheral blood can reflect the brain's pathophysiology following a stroke because the dying and lysed brain cells release antigens, which move into the blood when the brain endothelial barrier is compromised. However, the pathology of stroke is complex, variable, and involves many cellular signaling and metabolic pathways. Proteins reflective of blood coagulation/thrombosis, oxidation, inflammation, and CNS tissue injury have been shown to increase significantly in blood plasma or cerebral spinal fluid following brain injury. Energy failure, excitotoxicity, oxidative stress, blood brain barrier disruption, inflammation, necrosis, and apoptosis also may cause different molecules to appear in the blood stream. Despite this plethora of biomarker candidates, none have shown adequate sensitivity and specificity in clinical studies. Factors such as the inherent heterogeneity of the disease and the impedance of the blood-brain barrier to most proteins and metabolites may preclude finding a single biomarker for stroke. Thus, the present innovation utilizes a panel of biomarkers.

Finding a combination of biomarkers that is sensitive and specific enough to be clinically relevant is an ongoing challenge, although there are some promising initial studies. For example, one study's biomarker panel achieved a remarkable 98% specificity; however, the panel's sensitivity was only 17%. Montaner, J., et al., J. Intern. Med., 2011. 270(2): p. 166-74. Three studies have shown at least a 90% sensitivity with their biomarker panels. Sharma, R., et al., J. Stroke and Cerebrovascular Diseases 2014. 23(5): p. 910-918; Reynolds, M. A., et al., Clin Chem, 2003. 49(10): p. 1733-9; and Lynch, J. R., et al., Stroke, 2004. 35(1): p. 57-63. The most promising of these panels was from a study conducted by Reynolds et al (2003). Here, a 5-protein panel including BNGF, MCP-1, MMP-9, S100B, vWF was evaluated. The panel achieved a 92% sensitivity and 93% specificity; however, their control group was comprised of healthy individuals—in practice, this is an unlikely population to be suspected of stroke. Even with a seemingly high sensitivity, given the probability that many true stroke patients would be missed, this is not sensitive enough to be clinically useful.

Ideally, a biomarker or panel would be 100% sensitive and specific. It would perfectly classify stroke and non-stroke patients. This is, however, very unrealistic in practice. Researchers are faced with a tradeoff between the two characteristics—an analyte has high specificity but low sensitivity, or vice versa. To replace the current gold-standards of stroke diagnostics or at the least be used as a supplementary diagnostic tool, the accuracy must be higher than the methods already employed (i.e., NIHSS, pre-hospital assessments). The necessity of high diagnostic accuracy comes from the potential dangers of treating patients with thrombolytics. For example, a patient that is misdiagnosed with stroke and is given thrombolytic therapy could be at risk of hemorrhaging—a potential side effect of tPA. Because previous biomarker panels have not improved upon current diagnostic paradigms, the pursuit of a clinically useful biomarker panel is ongoing.

An ideal disease biomarker is specific to the disease. Therefore, biomarker candidates should be molecules expressed as a direct result of the disease. For ischemic stroke, the pathological change originates in the brain. If the pathology causes a release of proteins into the blood at the ischemic insult, these proteins would make for promising biomarker candidates. In one example, blood from the ischemic region of the brain of stroke patients was collected during mechanical thrombectomy for large vessel occlusions. Due to the invasive nature of this type of blood sampling, comparison of this blood to that of a non-stroke patient was not possible; however, a comparison to the same patient's arterial circulation was performed. This permitted a determination of differential abundances of proteins between blood found in the area of the stroke and blood from the general arterial circulation. This is significant because to be established as a biomarker candidate, the protein must be measurable in the circulating blood in an embodiment of the innovation. This is because such a biomarker could be developed into a clinically useful point-of-care diagnostic test which does not require invasive blood sampling.

As described more fully in the Examples, in one embodiment, arterial samples from the ischemic area of the brain and peripheral circulation were collected from stroke patients undergoing mechanical thrombectomy. To visualize overall differences in protein patterns between these two blood sources, equal amounts of ischemic serum proteins from every patient were pooled and separated via 2D gel electrophoresis, and the same procedure was done for circulating serum proteins. To visualize serum proteins from individual patients, each patient's paired samples—ischemic and circulating—were labeled with Cy5 and Cy3 fluorescent dyes, respectively, and then separated on the same gel by 2D gel electrophoresis. The normalized intensity of each protein spot was measured for each patient's blood samples and the relative protein abundance was calculated as the percent change in the intensity measured in the ischemic blood sample relative to that of the circulating blood sample. Proteins determined to have a significant difference in protein abundance between the ischemic and circulating samples were identified by mass spectrometry or by referencing the Swiss 2D PAGE database. Identified proteins, if available on the SOMAscan assay, were measured in venous blood collected from a different cohort of stroke patients and compared to venous blood of non-stroke patients.

Protein biomarkers were evaluated to identify potential candidates to differentiate/diagnose stroke patients from non-stroke patients . . . . There are many different methods for evaluation proteins, including two-dimensional gel electrophoresis, 2D-DIGE, MALDI-TOF, and the like.

Two-dimensional gel electrophoresis is a known proteomic technique for separating proteins. The first dimension of separation involves iso-electric focusing, which separates proteins along a polyacrylamide gel's horizontal dimension by their isoelectric point (the pH at which a protein has zero net charge). The second dimension of separation is SDS-PAGE, which separates proteins along a gel's vertical dimension by their molecular weight. For biomarker discovery, there is a marked advantage to two-dimensional separation over only one dimension. Given a sample with a mixture of proteins—in this case, serum—there is a probability of having numerous proteins with the same molecular weight. If one of those proteins had a measurable difference in abundance between two sample groups, that difference may be masked by other proteins. While it is possible that more than one protein can be present in a single spot from a 2-D gel, the probability of separation is higher than that of a 1-D gel.

Two-dimensional differential gel electrophoresis (2D-DIGE) is a technique that builds on 2D GE by combining multiple samples into one gel. When comparing samples with 2D GE, each sample requires its own gel. The disadvantage of separate gels becomes evident when comparing a particular protein spot from one gel with the equivalent protein spot in another gel. Although the separate gels may have been run under the same conditions, it does not always result in exactly the same spot separation. Because of this, alignment between gels may be slightly askew. The 2D DIGE method resolves this issue by running two samples simultaneously in the same gel, allowing for precise spot alignment. The two samples are labeled with different fluorescent dyes, so although any protein that is present in both samples will be located in the same gel spot, the wavelength of the fluorescent signal emitted from the protein will indicate to which sample it originated.

MALDI-TOF (Matrix Assisted Laser Desorption Ionization-Time of Flight) mass spectrometry is a technique used to identify protein spots from 2D gels. Proteins are removed from the gel by tryptic digestion, mixed with a matrix and then spotted to a target plate fitted for the mass spectrometer. The MALDI-TOF MS laser is used to excite and ionize the sample-matrix compound. Singly-charged ions then accelerate down an electric field, and the time required for the ions to reach the detector is reflective of their mass. The spectra of mass/charge ratios are then compared to a database to determine the likely identification for the protein.

The SomaLogic SOMAscan assay is a targeted high-throughput approach to differential protein analysis. It can measure the abundance of over 1300 proteins in a single 150 µL sample. The assay uses an aptamer-based technology where proprietary reagents bind to intact proteins within a sample. The bound reagents are then hybridized to DNA sequences which can be measured by fluorescence. The result is a proteomic dataset ready for bioinformatics analysis.

Endovascular mechanical thrombectomy directly recanalizes clogged arteries in stroke patients. During this procedure, a catheter is guided through the arterial line under fluoroscopic guidance until it reaches the occluded artery. A microcatheter is then extended past the offending clot, where it attaches itself to the thrombus, allowing it and the clot to be drawn out of the artery together. A previous study (Flores, A., et al. Journal of Neuroimaging, 2013. 23(2): p. 180-184.) showed the ability to 'safely and feasibly' draw blood samples simultaneously from the areas proximal and distal to the clot prior to clot removal. The investigator's intention was to permit real-time analysis of arterial blood gas concentrations as a means of assessing the value of proceeding with the thrombectomy. Their findings showed a differential arterial oxygen concentration across the thrombus; however, there was not a statistically significant difference for other measurements taken, including pH, and glucose, $Na^+$, $K^+$, $Ca^{2+}$, and $Cl^-$ concentrations. The blood collection method applied in Flores was used to examine differences in the concentration of proteins. Evaluation of these differences may provide insight into the biochemistry and pathophysiology of ischemic brain tissue, and ultimately to identify clinically relevant markers.

Protein biomarkers differentiating large versus small vessel occlusion were identified as described herein. Ischemic stroke patients with large vessel occlusions are candidates for treatment via mechanical thrombectomy. While thrombolytic therapy using tissue plasminogen activator (tPA) can be administered in most hospitals, the mechanical thrombectomy procedure is only performed in comprehensive stroke centers. When a patient that could benefit from mechanical thrombectomy is taken to facility that does not offer this endovascular therapy, they are often transported to the more appropriate stroke center. Time to treatment (and therefore risk of disability) can be significantly decreased if emergency medical personnel can assess en route whether the patient can be treated at the closest hospital or whether the patient needs to be transported to a comprehensive stroke center. A diagnostic test that differentiates large and small vessel occlusions is therefore clinically relevant.

In one example the venous blood of ischemic stroke patients with large vessel occlusions as well as patients with lacunar (small vessel) strokes was evaluated. The main goal was to determine what proteins are differentially expressed in the blood of stroke patients with large vessel occlusions when compared to stroke patients with small vessel occlusions. The SOMAscan assay data was used to evaluate the differential expression of 1310 proteins between these two patient groups. Univariate analyses were used to identify individual proteins that were significantly different between the two groups. Data from eight patients with middle cerebral artery (large vessel) occlusions and five patients with lacunar (small vessel) stroke were compared using the Mann Whitney U test. Of the 1310 proteins in the assay, 72 proteins were statistically different ($p \leq 0.05$) (Table 1).

TABLE 1

Proteins that distinguish large vessel from small vessel occlusions in stroke patients.

| Target | p | U | AVG(lacunar) | AVG(MCA) | SD(lacunar) | SD(MCA) |
| --- | --- | --- | --- | --- | --- | --- |
| TGF-b3 | 0.002 | 40 | 553.980 | 682.600 | 51.109 | 65.551 |
| COLEC12 | 0.002 | 40 | 2280.080 | 4013.100 | 146.309 | 1356.178 |
| KLRF1 | 0.003 | 1 | 581.840 | 502.388 | 47.430 | 36.124 |
| IL-17 | 0.005 | 1 | 568.620 | 491.838 | 26.265 | 25.411 |
| D-dimer | 0.006 | 38 | 2025.520 | 2817.900 | 234.365 | 410.070 |
| Hemopexin | 0.006 | 38 | 751.080 | 1845.013 | 385.343 | 664.367 |
| FABPL | 0.006 | 38 | 8732.220 | 20518.750 | 1996.253 | 9154.080 |

TABLE 1-continued

Proteins that distinguish large vessel from small vessel occlusions in stroke patients.

| Target | p | U | AVG(lacunar) | AVG(MCA) | SD(lacunar) | SD(MCA) |
|---|---|---|---|---|---|---|
| Fibrinogen | 0.006 | 38 | 50321.180 | 117205.650 | 8432.737 | 47765.553 |
| KYNU | 0.006 | 38 | 973.160 | 1325.750 | 169.790 | 194.100 |
| AMNLS | 0.006 | 2 | 183.220 | 162.300 | 7.648 | 13.247 |
| CAMK2B | 0.006 | 38 | 831.920 | 1056.250 | 80.043 | 190.630 |
| eIF-5 | 0.006 | 38 | 1448.700 | 1963.975 | 61.060 | 512.628 |
| Caspase-2 | 0.006 | 2 | 666.460 | 405.575 | 433.692 | 39.299 |
| ER | 0.006 | 38 | 941.740 | 1349.413 | 61.463 | 557.965 |
| WNT7A | 0.011 | 3 | 367.860 | 305.188 | 45.468 | 20.863 |
| Activin AB | 0.011 | 37 | 1183.840 | 1607.050 | 110.531 | 270.663 |
| Fibrinogen g-chain dimer | 0.011 | 37 | 8158.440 | 12215.638 | 930.625 | 2954.241 |
| BMX | 0.011 | 3 | 458.760 | 387.263 | 77.580 | 26.169 |
| RASA1 | 0.011 | 37 | 1402.940 | 1916.600 | 72.014 | 516.807 |
| NANOG | 0.011 | 3 | 270.040 | 202.163 | 99.397 | 12.629 |
| CAMK2D | 0.011 | 37 | 2644.400 | 3329.925 | 204.052 | 733.470 |
| AMPK a1b1g1 | 0.019 | 4 | 686.160 | 562.013 | 73.346 | 61.988 |
| CD70 | 0.019 | 4 | 453.480 | 383.138 | 30.983 | 40.950 |
| MMP-7 | 0.019 | 36 | 2434.120 | 3740.725 | 280.397 | 984.056 |
| Activin A | 0.019 | 36 | 4089.540 | 6536.638 | 749.605 | 2020.107 |
| H31 | 0.019 | 36 | 1435.460 | 1890.038 | 158.076 | 354.081 |
| UFC1 | 0.019 | 36 | 14624.920 | 19301.563 | 1214.973 | 3731.801 |
| sICAM-5 | 0.019 | 36 | 1202.820 | 1795.100 | 226.865 | 513.949 |
| MO2R1 | 0.019 | 4 | 1213.080 | 1039.300 | 156.060 | 78.908 |
| VEGF sR3 | 0.019 | 4 | 10348.040 | 7631.838 | 1710.641 | 1650.799 |
| SREC-II | 0.019 | 4 | 563.460 | 469.413 | 75.574 | 62.174 |
| Adrenomedullin | 0.019 | 4 | 3002.820 | 2474.863 | 387.158 | 344.423 |
| CLF-1/CLC Complex | 0.019 | 4 | 1023.480 | 659.813 | 659.523 | 37.124 |
| HGH | 0.030 | 5 | 633.500 | 459.325 | 137.669 | 58.598 |
| Aurora kinase A | 0.030 | 5 | 2899.040 | 1963.550 | 1049.113 | 176.515 |
| HTRA2 | 0.030 | 35 | 4437.420 | 5446.113 | 301.265 | 779.709 |
| SHP-2 | 0.030 | 35 | 4700.140 | 6952.438 | 1363.174 | 1665.286 |
| IL-7 Ra | 0.030 | 5 | 502.620 | 461.825 | 19.640 | 29.790 |
| MMP-1 | 0.030 | 35 | 3760.220 | 11361.325 | 1805.245 | 7944.916 |
| hnRNP K | 0.030 | 5 | 409.400 | 366.663 | 30.305 | 27.442 |
| IL-18 BPa | 0.030 | 35 | 5209.720 | 7489.575 | 1563.922 | 1603.100 |
| NR1D1 | 0.030 | 5 | 954.700 | 859.125 | 42.182 | 78.498 |
| CLC7A | 0.030 | 5 | 418.900 | 328.800 | 77.488 | 54.638 |
| MMP-17 | 0.030 | 35 | 1492.220 | 1765.450 | 78.072 | 252.767 |
| ENPP7 | 0.030 | 35 | 3893.100 | 8056.513 | 1215.072 | 4081.738 |
| Ubiquitin+1 | 0.030 | 35 | 1411.880 | 2101.138 | 382.568 | 680.975 |
| tau | 0.030 | 5 | 421.200 | 220.700 | 375.967 | 21.671 |
| Tenascin | 0.030 | 35 | 24804.060 | 30200.363 | 4194.023 | 6442.157 |
| cIAP-2 | 0.030 | 5 | 460.180 | 402.988 | 76.293 | 140.435 |
| EPHA3 | 0.030 | 5 | 919.720 | 411.038 | 1354.551 | 403.247 |
| OAS1 | 0.030 | 5 | 572.880 | 686.688 | 22.409 | 554.693 |
| PSME3 | 0.045 | 6 | 545.220 | 370.713 | 153.352 | 35.901 |
| AMPM2 | 0.045 | 34 | 12826.480 | 18872.400 | 3091.215 | 4636.649 |
| KI2L4 | 0.045 | 34 | 1107.780 | 1521.775 | 244.625 | 312.938 |
| paraoxonase 1 | 0.045 | 6 | 263.900 | 239.588 | 17.813 | 15.850 |
| Ubiquitin | 0.045 | 34 | 30571.280 | 42331.500 | 7532.182 | 9069.998 |
| Galectin-3 | 0.045 | 34 | 22080.700 | 27861.925 | 3059.793 | 4838.796 |
| CRK | 0.045 | 34 | 11585.900 | 15894.513 | 1548.399 | 3242.429 |
| FGFR-2 | 0.045 | 6 | 645.480 | 435.013 | 277.348 | 35.400 |
| VEGF sR2 | 0.045 | 6 | 12034.260 | 9570.300 | 1744.259 | 1758.932 |
| prostatic binding protein | 0.045 | 34 | 3635.280 | 6059.713 | 1509.813 | 2430.873 |
| RANTES | 0.045 | 6 | 104045.100 | 62386.200 | 35502.738 | 32336.383 |
| IL-1F8 | 0.045 | 6 | 924.400 | 802.800 | 153.602 | 60.362 |
| NSF1C | 0.045 | 34 | 1418.120 | 2646.638 | 580.193 | 1710.595 |
| FGF23 | 0.045 | 34 | 950.220 | 1263.250 | 151.628 | 301.337 |
| HB-EGF | 0.045 | 6 | 404.320 | 316.263 | 125.756 | 32.347 |
| TFPI | 0.045 | 34 | 62021.360 | 82255.550 | 6786.145 | 22271.176 |
| GFAP | 0.045 | 34 | 809.760 | 2217.988 | 48.741 | 2150.110 |
| PDGFRA | 0.045 | 34 | 2887.460 | 3515.063 | 398.043 | 721.101 |
| KI3L2 | 0.045 | 6 | 3088.260 | 886.775 | 4717.833 | 77.687 |
| MMP-13 | 0.045 | 34 | 861.140 | 1404.550 | 79.393 | 1092.460 |
| LRRT1 | 0.045 | 34 | 130.660 | 244.075 | 7.409 | 268.170 |

Using a univariate Mann Whitney U-test, 72 serum proteins were found that showed significantly different concentrations (p≤0.05) in stroke patients with small vessel occlusions (lacunar) compared with patients with large vessel occlusions (MCA).

Figure 1N:
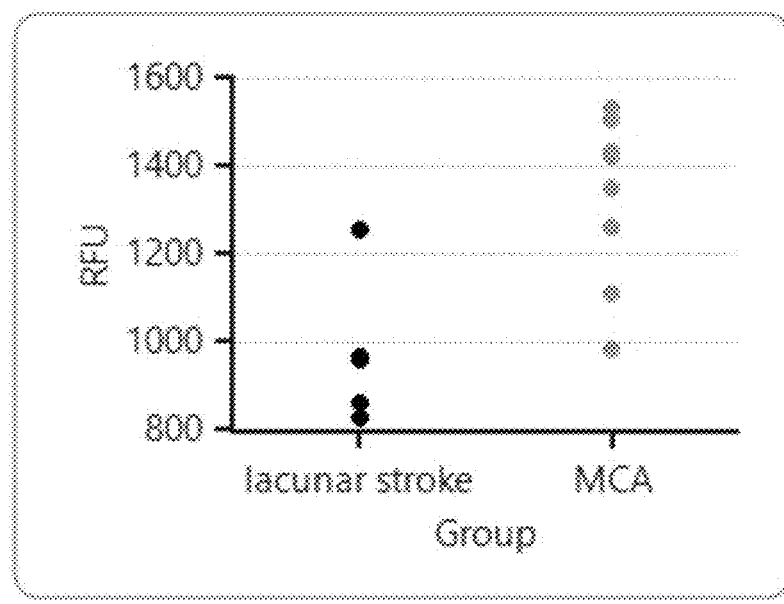
FIG. 1N depicts a scatter plot that compares serum concentrations of proteins with highly significantly differences between large vessel occlusions (MCA) and small vessel occlusions (lacunar). Following Mann Whitney U test on all stroke patients fourteen proteins were found to have a p-value p<0.01. RFU=relative fluorescent units.

When examining the scatter plots for the top 14 proteins (p≤0.01), the distribution of the RFU measurements for each group has excellent separation, making a threshold value easy to define for calculating a clinically valuable sensitivity and specificity (FIGS. 1A-1N).

In one aspect, the innovation provides a method for characterizing protein biomarker candidates for inclusion in biomarker panels for diagnosing stroke.

Example I

In one example, characterization of patients' blood was performed using various proteomic techniques described below. The proteomic analysis was not restricted to specific protein biomarker targets, as has been the focus of previous studies. Rather a comprehensive proteomic approach was undertaken using 2-dimensional protein separation, mass spectrometry, and high-throughput aptamer-based technology to study differences in blood protein expression between ischemic stroke patients and non-stroke patients. Blood was collected from patients upon admission to the hospital due to the importance of finding a diagnostic biomarker that is measurable in the blood within a few hours of stroke onset. Additionally, blood was collected directly from the ischemic core of stroke patients undergoing an established clot-removal procedure—a source that has not previously been explored to identify novel protein biomarkers.

Two main proteomic approaches were used to study blood biomarkers. The first is two-dimensional gel electrophoresis (2D GE) and two-dimensional differential gel electrophoresis (2D DIGE) and the second is a high-throughput aptamer-based protein assay (SOMAscan). Both approaches allow for a broad analysis of differential protein expression in either a non-targeted or targeted fashion.

Blood Sample Collection

Two IRB-approved studies were executed for blood collection. In the thrombectomy study, arterial blood from the ischemic core of stroke patients undergoing mechanical thrombectomy was collected. In the peripheral blood study blood was collected via venipuncture from patients presenting to the emergency department with stroke-like symptoms. All blood collection took place at Miami Valley Hospital (Dayton, Ohio), with the exception of healthy controls, which were obtained from commercial vendors.

Patients undergoing endovascular mechanical thrombectomy for treatment of ischemic stroke and whose legally authorized representative gave informed consent were subjects of this study. Exclusion criteria included minors, pregnant women, and patients with known infectious disease. If (1) the patient met these criteria, (2) the family was present to sign the informed consent before the procedure was initiated, and (3) penumbral blood was able to be aspirated during the procedure, the patient was included in this study. Blood collection occurred between November 2015 and October 2016. During this time, informed consents were obtained for 18 patients, and blood samples were obtained for 9 patients.

Figure 2:
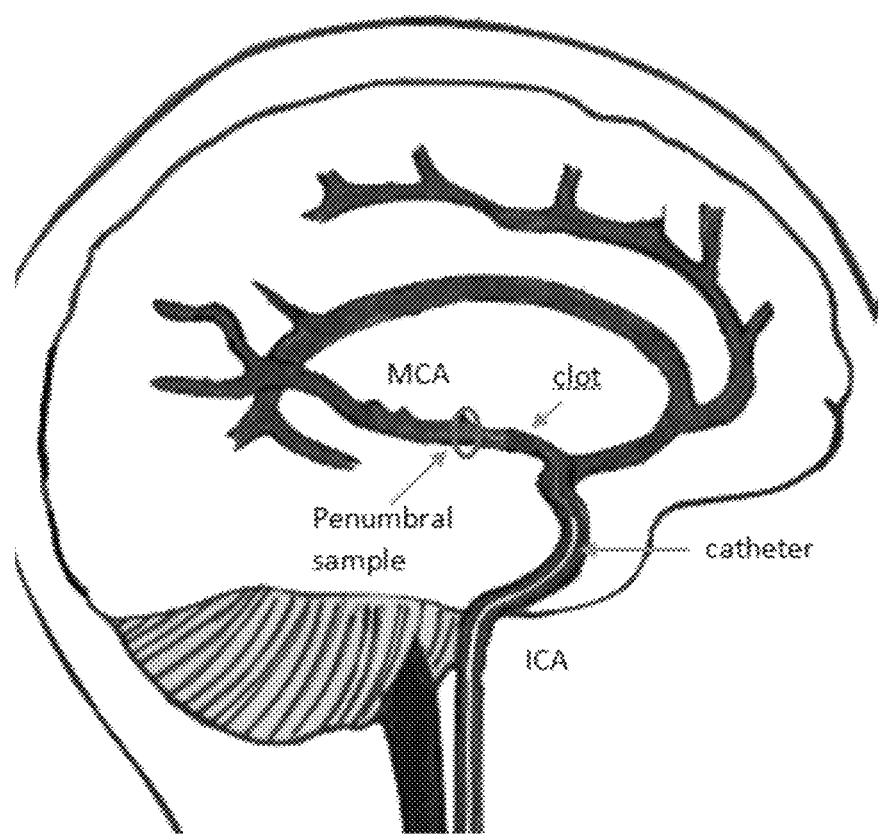
FIG. 2 is an illustration of a mechanical thrombectomy procedure from the sagittal view. A catheter passes through the clot before collecting blood from the occluded middle cerebral artery, MCA.
Figures 3A, 3B, 3C, 3D, 3E, 3F, 3G, 3H, 3I:
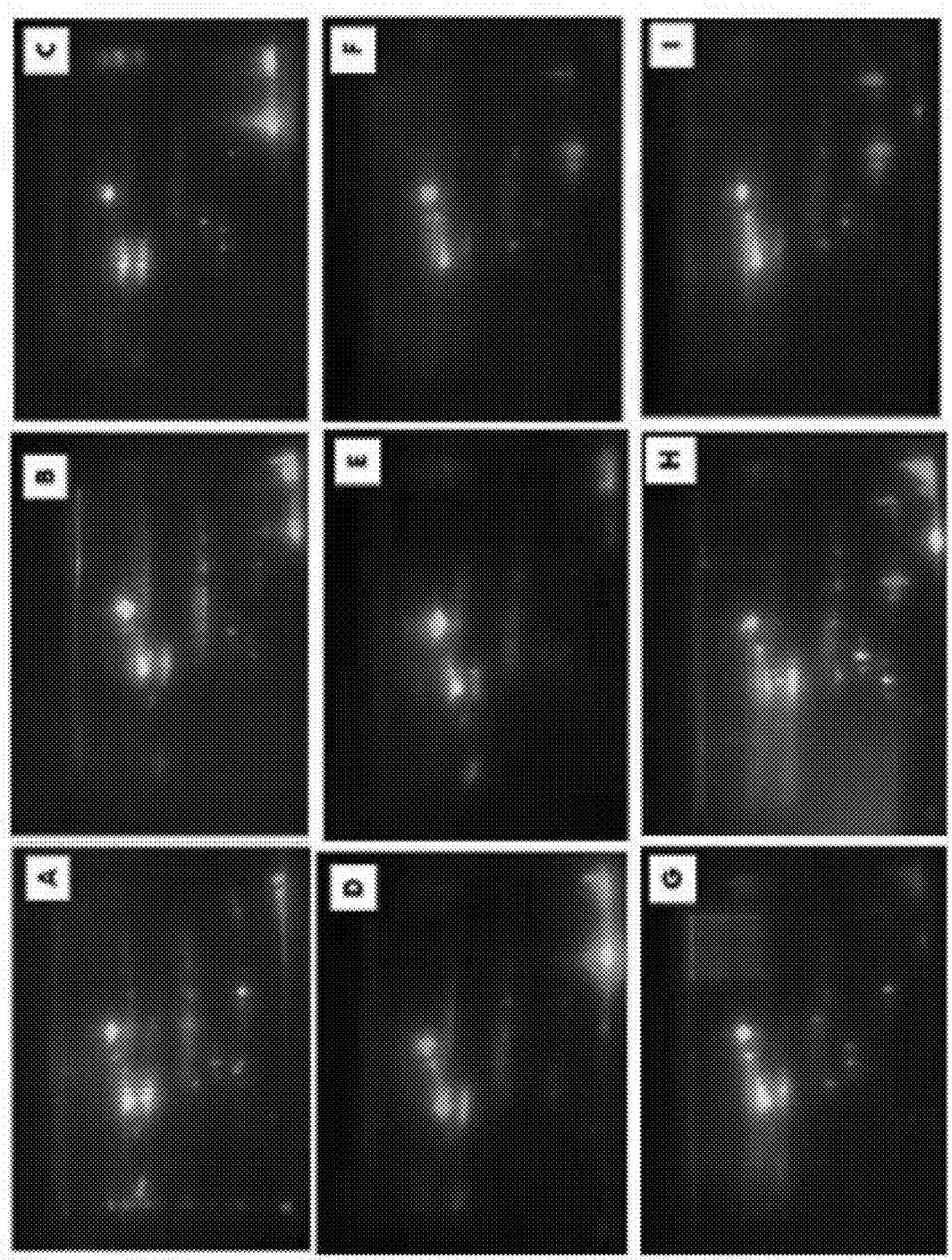
FIG. 3A shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3B shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3C shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3D shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3E shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3F shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3G shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3H shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.
FIG. 3I shows a 2D two-dimensional differential gel electrophoresis (DIGE) image for one of nine patients undergoing mechanical thrombectomy. Serum proteins more abundant in the circulating sample appear green while those more abundant in the ischemic sample appear red. Proteins found equally in both samples appear yellow.

Ischemic core and circulating arterial blood samples were obtained in the angiosuite by a neurointerventional radiologist. Mechanical thrombectomy was performed with Solitaire Revascularization Device (Medtronic, Minneapolis, MN) delivered through a microcatheter guided from the femoral artery to the occluded cerebral artery (FIG. 2). Prior to clot retrieval, a small sample of blood was obtained from the systemic circulation in the internal carotid artery (arterial sample). The microcatheter and Solitaire device was then extended to pass through the clot. While the Solitaire device was expanding prior to clot removal, a small amount of blood was aspirated distal to the clot in the ischemic core (ischemic sample). Then the clot was retracted with the Solitaire device through the arterial line.

Arterial and ischemic blood samples were collected in red-top tubes, allowed to clot at room temperature, and centrifuged for 15 min at 3,000×g in a refrigerated centrifuge (4° C.). The supernatant serum was removed and stored at −80° C. in aliquots for later analysis.

Patients presenting to hospital emergency department with stroke-like symptoms (termed "stroke-alert") and whose legally authorized representative gave informed consent were subjects of this study. Exclusion criteria included minors and patients with known infectious disease. Patient samples were categorized into three groups based on the final diagnosis noted in their medical records: (A) Patients with a final diagnosis of ischemic stroke, (B) Patients with a diagnosis of transient ischemic attack (TIA), and (C) Patients—referred to as stroke mimics—with a diagnosis other than ischemic stroke and other than TIA. Blood collection occurred between November 2016 and February 2017. Blood from healthy controls with similar age, race, and sex distribution to the stroke cohort was obtained from two commercial vendors: 11 samples from Conversant Bio (Huntsville, AL) and 15 samples from Innovative Research (Novi, MI).

All stroke-alert patients had blood drawn via venipuncture upon arrival to the emergency department according to the hospital's standard procedure. Blood was collected in gold-top (serum separator) tubes, inverted 5 times, then allowed to clot for up to 30 min. Samples were then centrifuged for 15 min at 3,000×g in a refrigerated centrifuge (4° C.). The supernatant serum was removed and stored at −80° C. in aliquots for later analysis.

Serum Preparation for 2D Separation.

Serum collected during thrombectomy was removed of albumin with Aurum Affi-Gel Blue mini columns (Bio-Rad, Hercules, CA), then salts, lipids, and nucleic acids were eliminated using the Ready Prep 2D CleanUp Kit (Biorad, Hercules, CA). This method was determined in optimization studies to yield the best separation and visualization of proteins on a gel. The resulting protein pellet was suspended in rehydration buffer (8 M Urea, 2% CHAPS, 50 nM DTT, 0.2% Bio-Lyte 3/10 Ampholyte) (BioRad, Hercules, CA)), and the concentration determined using the BioRad Protein Assay (BioRad, Hercules, CA). For some studies, a pooled sample was created by combining 40 μg of protein from each of five patient samples to make a 200 μg sample.

Isoelectric Focusing.

The first dimension of protein separation was achieved with isoelectric focusing, which separates proteins based on their isoelectric point (pI). Prepared protein samples were inoculated onto a ReadyStrip IPG strip (11 cm, pH 3-10 or 11 cm, pH 4-7) (Bio-Rad, Hercules, CA), and incubated at room temperature for approximately 12 hours. Iso-electric focusing (IEF) of the IPG strip was performed in a focusing tray on PROTEON IEF Cell (BioRad, Hercules, CA). IEF was programmed for 3 automated steps based on IPG strip length. A total of 30,000 Volt-hours was achieved over 5.3 hours total time with a maximum current of 50 μA and cell temperature of 20° C.

IPG Equilibration.

After IEF, the IPG strips were equilibrated in 2 mL of Equilibration Buffer I consisting of 6 M urea, 2% SDS, 0.375M Tris-HCl, pH 8.8, 20% v/v glycerol, and 2% w/v DTT (BioRad, Hercules, CA) for 10 min and then in 2 mL Equilibration Buffer II consisting of 6 M urea, 2% SDS, 0.375M Tris-HCl, pH 8.8, 20% v/v glycerol, and 0.5 g iodoacetamine (BioRad, Hercules, CA) for 10 min to reduce the disulfide bonds and alkylate the SH groups of the proteins, respectively.

SDS-PAGE.

Proteins on the IPG strip were then separated in a second dimension by molecular weight on AnykD Criterion TGX pre-cast polyacrylamide gel (11 cm IPG/Prep+1 well, 550 μL (BioRad, Hercules, CA)) in a Criterion electrophoresis cell run at 200 V, 70 mA, for approximately 40 min with 1×Tris/glycine/SDS running buffer (25 mM Tris, 192 mM glycine, 0.1% SDS, pH 8.3). The voltage was increased to 300 V when running two gels in one electrophoresis cell.

Staining and Imaging.

Following electrophoresis, the gel was removed from its cassette, washed in nanopure water, and then covered in Gel-Code Blue stain (BioRad, Hercules, CA) overnight. After destaining with nanopure water, the gel was imaged with a ChemiDoc Imager (BioRad, Hercules, CA).

Image Analysis and Spot Identification.

Because the gel is marked with a molecular weight standard and the range of pH values on the isoelectric strip is known, some spots were preliminarily identified based on weight and isoelectric point (pI) using known 2D gel databases, including SWISS-2DPAGE (http://world-2dpage.expasy.org/swiss-2dpage/) and literature which contains protein data on various 2-D PAGE and SDS-PAGE reference maps (Hoogland, C., et al., Proteomics, 2004. 4(8): p. 2352-6; Pieper, R., et al., Proteomics, 2003. 3(7): p. 1345-64). Otherwise, spots were identified using mass spectrometry following in gel digestion of proteins Serum Preparation for 2D Separation.

Albumin was removed from the serum samples collected during thrombectomy using Aurum Affi-Gel Blue mini columns (Bio-Rad, Hercules, CA). Salts, lipids, and nucleic acids were then removed using a ReadyPrep 2D CleanUp Kit (Biorad, Hercules, CA), resulting in a protein pellet.

Fluorescent Labelling of Serum Proteins.

Protein pellets were solubilized in 30 μL buffer consisting of 8 M Urea, 40 mM Tris, and 4% CHAPS at pH 8.0. The protein concentration of the resulting solution was measured with the BioRad Protein Assay (Bio-Rad, Hercules, CA) and a sample containing 25 μg of protein was used for analysis. Proteins in the arterial and ischemic samples then were stained with Cy3 and Cy5 dye, respectively, using the CyDye DIGE-Fluor Labeling Kit (GE Healthcare, Pittsburgh, PA). An internal standard was created using equal quantities of protein from arterial and ischemic samples. This combined sample was similarly stained with Cy2 dye. Dye reactions were stopped with addition of 10 mM lysine. Dye-labeled serum samples were diluted 1:1 with a solution of 8 M Urea, 4% CHAPS, and 130 mM dithiothreitol (DTT) and the three solutions of dye-labeled proteins from each patient were combined.

Isoelectric Focusing and IPG Equilibration.

Each combined dye-labeled sample was brought to 200 μL total volume using 8 M Urea, 2% CHAPS, 50 mM DTT, 0.2% Bio-Lyte 3/10 Ampholyte (BioRad) and then applied to an 11 cm, pH 3-10 immobilized pH gradient strip (ReadyStrip IPG, Bio-Rad, Hercules, CA). Iso-electric focusing (IEF) of the proteins was performed on the IPG strip using a PROTEON IEF Cell (Bio-Rad, Hercules, CA) automated to deliver a total of 30,000 Volt-hours over 5.3 hr at a cell temperature 20° C. and maximum current of 50 μA. After IEF, proteins on the IPG strips were reduced with 2% w/v DTT in a buffer of 6 M urea, 2% SDS, 0.375 M Tris-HCl, and 20% v/v glycerol at pH 8.8 (Bio-Rad Equilibration Buffer 1) for 15 min at room temperature and then alkylated in 6 M urea, 2% SDS, 0.375 M Tris-HCl, 20% v/v glycerol, 0.5 g iodoacetamide, pH 8.8 (Bio-Rad Equilibration Buffer 2) for 15 min at room temperature.

SDS-PAGE.

Proteins on the IPG strip were separated by molecular weight using electrophoresis in the second dimension on AnykD Criterion TGX polyacrylamide gels (Bio-Rad, Hercules, CA) run at 200 V, 70 mA, for approximately 40 min with a running buffer consisting of 25 mM Tris, 192 mM glycine, 0.1% SDS, at pH 8.3.

Imaging.

Following electrophoresis, gels were removed from their cassettes, briefly washed in ultrapure water, and then visualized with a ChemiDocMP+ Imager (Bio-Rad, Hercules, CA). Four images were generated for each gel: one image specific for each CyDye (Cy5, Cy3, Cy2) plus a composite image to visually display the relative abundance of proteins in serum samples taken from arterial (Cy3) and ischemic (Cy5) sites.

Image Analysis and Normalization.

Using the image analysis program ImageJ Version 1.51p, visible protein spots from the gels were manually selected with the ROI (region of interest) Manager Tool. Spot selections were saved as an overlaying template to ensure alignment of spots across all gel images for each patient. For each Cy3 and Cy5 image, the maximum and minimum signal intensity for each spot was measured and exported to Excel. To correct for the local background noise, each protein spot's minimum signal intensity value was subtracted from its maximum signal intensity. For each gel, the Cy5 values from all the spots were summed. Then the Cy5 value for each spot was normalized to this summed intensity. The same procedure was performed for Cy3 values. To account for gel-to-gel variation, an additional normalization step was performed based on the Melanie Total Volume Normalization method, Swiss Institute of Bioinformatics. For each gel, the Cy2 values from all the spots were summed. Then the mean of the summed intensities was calculated across the Cy2 gels for all patients. A reference image was selected by using the Cy2 gel with the summed intensity closest to the mean summed intensity. Each gel's normalization factor was then calculated as the reference image's summed intensity divided by the summed intensity for the gel being normalized. Each spot within that gel then was divided by this normalization factor. The process was repeated for all Cy3 and Cy5 gel images.

Statistical Analysis.

To determine the relative increase or decrease in abundance for each protein in the ischemic sample relative to that in the arterial sample, the normalized fluorescent image intensity from each protein spot in the ischemic sample (Cy5 dye) was divided by the normalized fluorescence image intensity from the same protein spot in the arterial sample (Cy3 dye). To determine proteins that had significant differences between these sample groups, the Wilcoxon signed rank test was used (Microsoft Excel v2013, Microsoft Corp, Redmond, WA). P-values below 0.05 were considered statistically significant.

Protein Identification

In Gel Digestion.

Spots of interest were excised from gels using 1.5 mm or 3 mm spot-picking tool (The Gel Company, San Francisco, CA). Following a standardized in-lab protocol, gel pieces were washed twice in 50% diluted acetonitrile (ACN) for 15 min, dehydrated with 100% ACN for 2 min, and rehydrated with 100 µL 100 mM ammonium bicarbonate ($NH_4HCO_3$) for 5 min. Next, 100 µL ACN was added for a 15 min incubation, the gel slice was covered with ACN until it turned white and then 100 µL 25 mM ammonium bicarbonate was added for 10 min. The supernatant was removed and 100 µL of a 1:1 mixture of 50 mM $NH_4HCO_3$:ACN was added. This step was repeated once again and then the samples were vacuum centrifuged for 5 min. The gel piece was treated with 25 mM $NH_4HCO_3$, 1 µL trypsin, and 15 µL 50 mM $NH_4HCO_3$ for overnight digestion. To recover peptides, the supernatant was removed and 20 µL 0.3% trifluoroacetic acid (TFA) was added to saturate the gel piece. Application of 30 µL of 50% ACN containing 0.3% TFA was repeated 3 times for 10 min each, with supernatants collected after each repetition. Combined supernatants were then reduced to 10 µL volume in a SpeedVac and stored at −20° C. until Zip-Tip clean up.

Zip Tip Cleanup and Target Plate Preparation.

Following digestion, proteins underwent C18 ZipTip clean up to de-salt and concentrate the peptide sample. Methanol was used to activate the C18 pipette tip (Millipore Sigma, Burlington, MA). Then 0.1% TFA was used to wash out the methanol. After the peptide sample was loaded onto the ZipTip, it was washed with 0.1% TFA and eluted to a fresh tube with 90% ACN containing 0.1% TFA. One microliter of the cleaned sample was then mixed with an equal volume α-cyano-4-hydroxycinnamic acid (CHCA). One microliter of this solution was spotted to an MTP 384 brushed-steel target plate for the Autoflex MALDI-TOF/TOF mass spectrometer (Bruker Daltonics, MA).

MALDI TOF Mass Spectrometry.

Prior to each session, the AutoFlex MALDI-TOF/TOF mass spectrometer was calibrated using a peptide mix from Bruker Daltonics. To generate protein/peptide spectra (MS data) for unknown samples, the FlexControl 3.4 software settings were set to reflector mode, with laser power set at 30% and detector gain set at 3.5. Spectra were obtained in the 200-5000 Dalton range. The laser was fired between 4000-10000 times until peaks were generated in the 104 or higher intensity range. The resulting spectrum was processed with the PMS FAMS Method which deselected for matrix-related peaks before being saved. A mass list was generated in the Flex Analysis software. To further fragment peaks of interest (MS/MS data), Bruker LIFT mode was implemented using automated settings for detector gain and Dalton range. Laser power ranged from 80-100% and the laser was fired 10,000-25,000 times.

Mass Spectrometry Data Analysis.

MS and MS/MS data were submitted to the MASCOT server (Matrix Science, London, United Kingdom) at Wright State University's Proteomics Analysis Lab. The data were searched against NCBI database using the following settings: *Homo sapiens* taxonomy, tryptic cleavage with maximum of two missed cleavages, variable modifications of carbamidomethylation and oxidation of methionine, a mass accuracy tolerance up to 2.5 Da for the MS and a tolerance up to 1.5 for the MS/MS. A Mowse probability score had to be considered significant to accept the identification.

2D Page Referencing.

When MS data was unavailable, protein spots of interest were identified by referencing two 2D PAGE databases for human plasma or serum. The approximate molecular weight and isoelectric point of the unknown protein spot, as well as its positional relationship to nearby MS-identified spots, were used to coordinate to the reference gel.

SOMAscan Data Analysis

Multiplex assay. Eighty serum samples were submitted to SomaLogic, LLC for measurement of 1310 proteins by the SOMAscan assay. For this analysis, SOMAmer reagents (aptamers) labeled with a photocleavable linker and biotin were immobilized on streptavidin-coated beads. Each serum sample was incubated with reagents and serum proteins were allowed to bind, forming SOMAmer-target protein complexes. Unbound proteins were washed away, and bound proteins were photocleaved with UV light, leaving only the reagents to represent the once-bound proteins. The reagents then were bound to complementary sequences of DNA hybridization probes on a microarray. Probes were then quantified by fluorescence. The result was measured as relative fluorescent units (RFU) and is directly proportional to the amount of target protein in the original serum sample.

Normalization.

The SOMAscan assay results were normalized using three methods. First, hybridization normalization corrects for systematic effects introduced during the DNA hybridization step. A control sequence that was introduced into the assay prior to hybridization was used to calculate a scaling factor, and each sample was normalized to this factor. Second, plate scaling corrects for variation that occurs between array plates. A calibrator control for serum was run in replicate within the same assay as the serum samples. Signals from this control were used to calculate a single scale factor for each plate. Third, the median normalization allows for comparison of signals across a plate by correcting for introduced variation from the assay or natural variation in samples' total protein concentrations. The median signal intensity from each subarray was used to calculate a sample-based scaling factor.

Univariate Statistical Analysis.

Univariate analyses were performed using SomaSuite software (SomaLogic, Boulder, CO) to determine proteins with a significant difference between groups. Non-parametric analysis was chosen because of small sample size. The Mann Whitney U test and the Kolmogorov—Smirnov (KS) test were used to compare two groups, while the Kruskal-Wallis test was used to compare three groups. The threshold for statistical significance was set at $p<0.05$.

Random Forest Analysis (RFA).

RFA is a machine learning program that can predict which variables are likely linked to the diagnosis outcome. RFA was programmed using R software. The program randomly selected patient samples with replacement. The program then randomly selected 37 proteins from the 1310-protein SOMAscan assay results and generated a decision tree using as many of the 37 proteins as necessary until it had categorized the patient samples into a diagnosis group (stroke, mimic, etc). This process was repeated 1,000 times to create a decision-tree forest (the random forest). Each set of patient data then was tested by the random forest. Based on the patient's 1310 protein RFU measurements, the forest votes—each decision tree classifies the patient into a diagnosis group in accordance with its decision parameters. The diagnosis group with the most votes is the group to which that patient was categorized. To create one decision tree that represents the entire random forest, replicate random forests were generated 1,000 times and the 10 proteins that appeared most frequently during these simulations were used to create a single tree (biomarker panel). This final tree was used to test all patient samples and generate a classification table, from which the sensitivity and specificity of the biomarker panel was determined, as shown schematically in Table 2, where letters represent the numbers of patients in each group.

TABLE 2

Classification table for calculation of sensitivity and specificity.

|  | Test Positive for Disease | Test Negative for Disease |
|---|---|---|
| Disease Present | a | b |
| Disease Absent | c | d |

Sensitivity, Specificity.

The sensitivity of a diagnostic test is determined by its ability to correctly classify patients with the disease diagnosis. It is also referred to as the true positive rate and is calculated as a/(a+b) using values shown in Table 2. The specificity of a diagnostic test is the tests ability to correctly classify patients who do not have the disease diagnosis. Specificity is also referred to as the true negative rate and is calculated as d/(c+d) using values shown in Table 2. These fractions were represented as percentages.

Likelihood Ratios.

A likelihood ratio was calculated for each biomarker panel created by the random forest analysis to assess the value of a diagnostic test. The positive likelihood ratio (LR+) is used to determine whether a positive test result is positively associated with the disease. It is the probability of a positive test given the presence of the disease divided by the probability of a positive test result given the absence of the disease. It is calculated as follows:

LR+=sensitivity/1−specificity

The negative likelihood ratio determines whether a negative test result is associated with the absence of disease. It is the probability of a negative test result given the presence of the disease divided by the probability of a negative test result given the absence of the disease. It is calculated as follows:

LR−=1−sensitivity/specificity

A high LR+ and low LR− are associated with high diagnostic accuracy.

Nine patients were included in the thrombectomy study (Table 3). The average age was 77 and NIHSS scores ranged from 10-31. The locations of the patients' occlusions varied, with the majority occurring in the left middle cerebral artery. Three of the patients received tPA thrombolytic therapy prior to the thrombectomy procedure.

TABLE 3

Patient characteristics for thrombectomy study.

| Patient # | Sex | Age | Clot Location | NIHSS score (initial) | tPA |
|---|---|---|---|---|---|
| 1 | M | 82 | Right ICA | 19 | N |
| 2 | F | 60 | Left MCA | 10 | N |
| 3 | M | 78 | Left MCA | 21 | N |
| 4 | F | 87 | Left MCA | 31 | N |
| 5 | M | 83 | Left MCA | 16 | N |
| 6 | M | 69 | Right MCA | 17 | Y |
| 7 | F | 79 | Basilar artery | 16 | N |
| 8 | F | 69 | Left MCA | 16 | Y |
| 9 | F | 83 | Left MCA | 26 | Y |

ICA = internal carotid artery;
MCA = middle cerebral artery;
NIHSS = National Institute of Health Stroke Scale;
tPA = tissue plasminogen activator (thrombolytic therapy)

Figure 4:
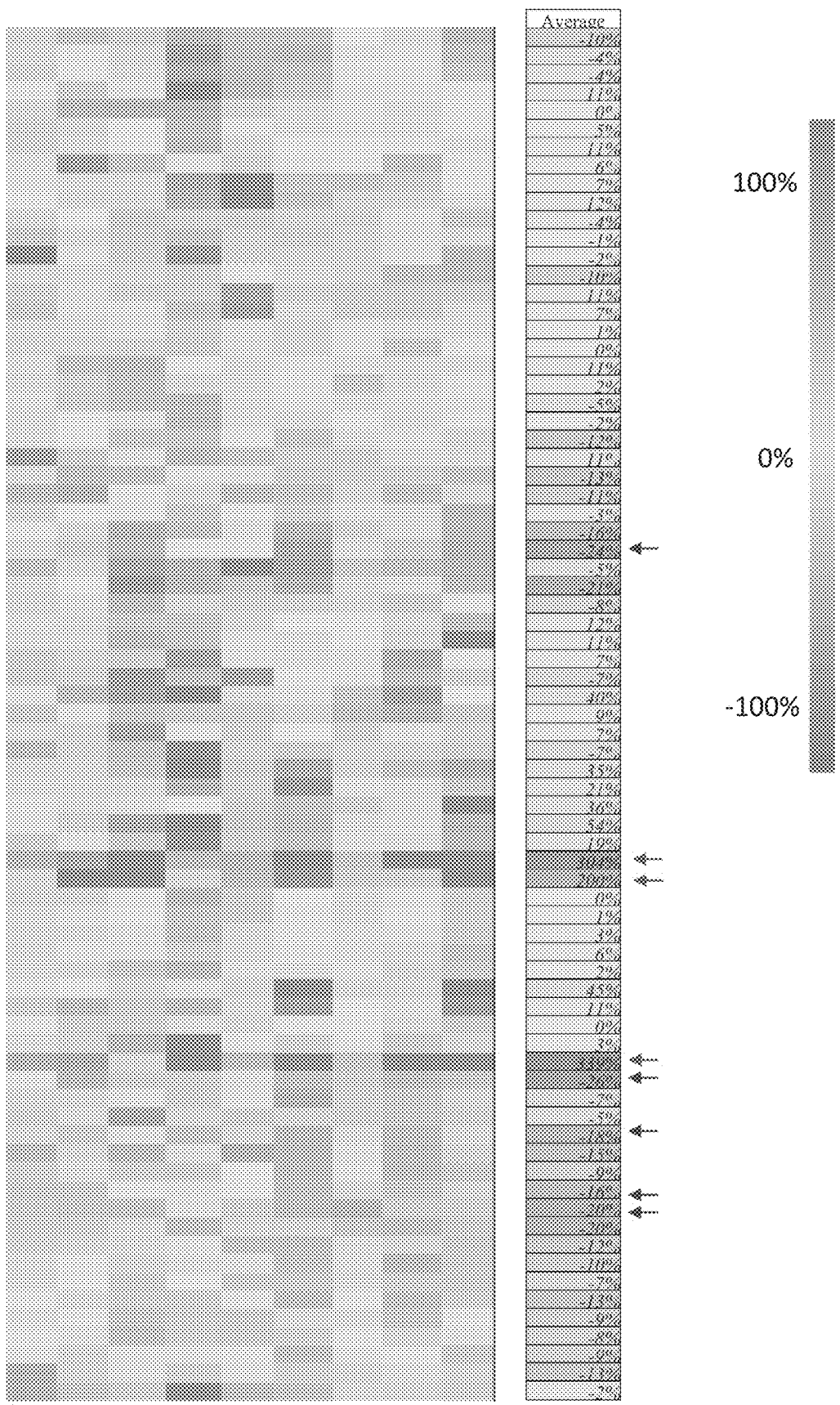
FIG. 4 is a heat map showing the percent increase or decrease in Cy5 image intensity relative to the Cy3 image intensity. Each column represents one of the nine patients analyzed. Each row represents one of seventy-five protein spots measured. Green indicates an increased signal in the ischemic blood. Orange to red indicates a decreased signal in the ischemic blood. The right column is the percent change in intensity averaged over all nine patients. Three spots showed greater than 200% increase in the average signal intensity (green arrows). However, this difference was not statistically significant. Five spots showed a statistically significant difference in the intensity of ischemic and circulating blood samples (p<0.05) when compared using Wilcoxon signed rank test (red arrows).
Figure 5:
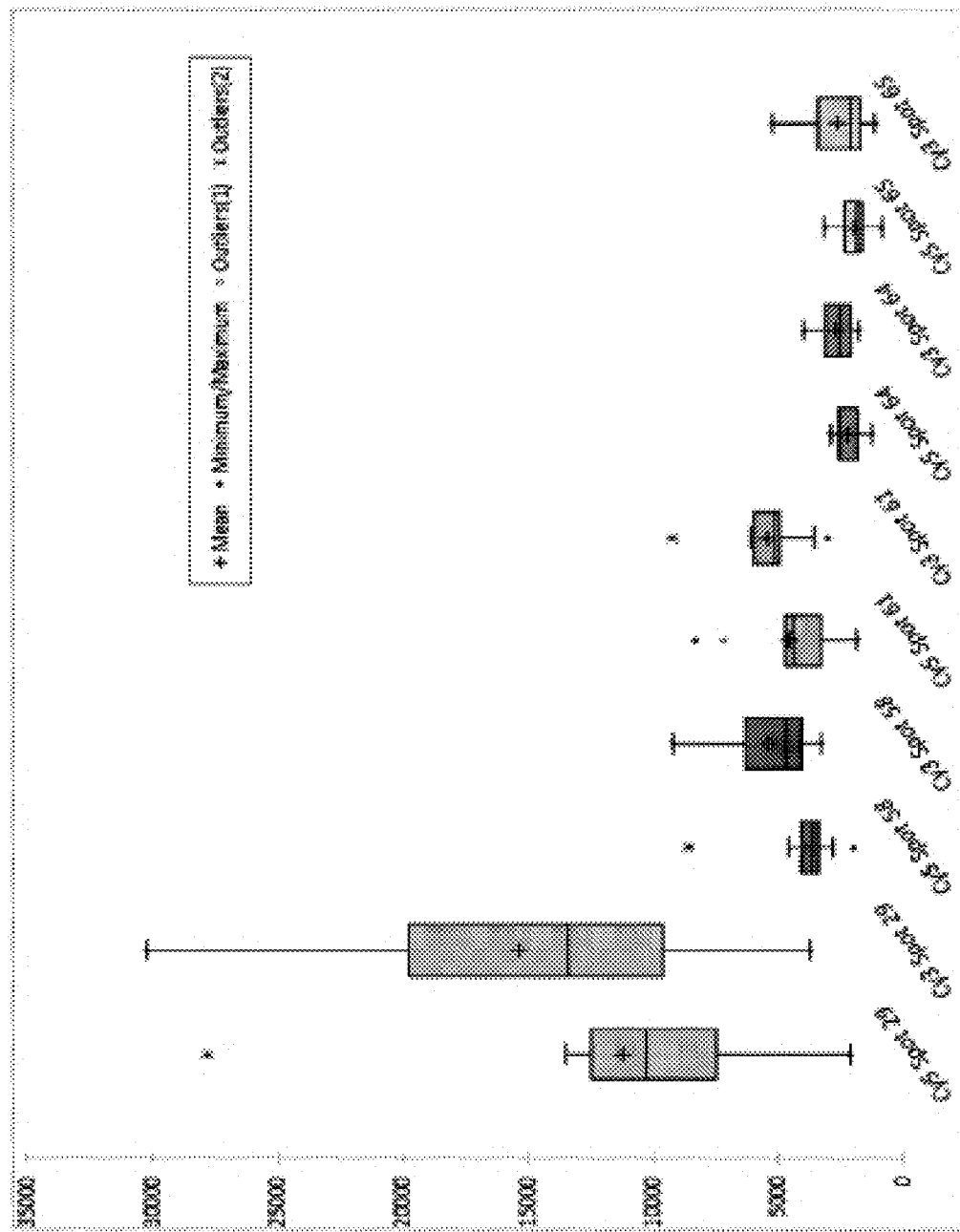
FIG. 5 is a comparison of statistically significant gel spots identified in thrombectomy study. Wilcoxon signed rank test resulted in 5 protein spots with statistically significant differences (p<0.05) between ischemic and circulating serum. The interquartile range box represents the middle 50% of data with the whiskers extending to the top and bottom 25%, excluding outliers. The horizontal line represents the median of the data.

Each patient's paired blood serum samples were analyzed with 2D-DIGE (FIGS. 3A-3I) to evaluate patient-specific changes in protein abundance in ischemic versus circulating blood. Protein spots were selected for quantitative analysis if they were present in the gels from all nine patients. The change in relative abundance of 75 selected protein spots for each patient is displayed as a heat map in FIG. 4. The average relative abundance across all patients for each protein is shown in the right hand column. High variability was seen across the nine patients. A number of protein spots had a high-fold increase in abundance in the ischemic serum of some patients. As an example, 4 of the 9 patients showed more than a 300% increase in abundance for protein spot 46 while another 2 patients had 47% and 70% increases and the remaining 3 patients showed a decrease in abundance. The average percent change was 304%; however, this value was not statistically significantly different by the Wilcoxon signed rank test (p=0.097). A similar finding was seen for spot 47 (average=200% increase in ischemic serum, p=0.097) and spot 57 (average=339% increase in ischemic serum, p=0.155). When the univariate Wilcoxon signed rank analysis was performed for the remaining protein spots, there were five protein spots which showed a statistically significant difference in abundance between ischemic serum samples and the arterial circulation serum samples (FIG. 5). Identifications of these spots are indicated in Table 4.

TABLE 4

Protein identifications for protein spots analyzed in thrombectomy study.

| Gel Spot | ExPASy SWISS 2D PAGE database ID* | Mascot Identification | Mowse score | % Sequence Coverage |
|---|---|---|---|---|
| Control 1 | Alpha-1-antitrypsin | Alpha-1-antitrypsin | 62 | 46% |
| Control 2 | Serotransferrin | Serotransferrin | 57 | 25% |
| Control 3 | Haptoglobin | Haptoglobin | 152 | 11% |
| Protein spot with statistical differences in image intensities between ischemic and circulating blood samples | | | | |
| 29 | Albumin | Serum Albumin | 79 | 10% |
| 58 | Spot present but not labeled | Chain A, Human Serum Transferrin Recombinant N-terminal lobe | 51 | 7% |
| 61 | Ig heavy chain gamma | Chain A, Apo-Human Serum Transferrin (Non-glycosylated) | 51 | 1% |

TABLE 4-continued

Protein identifications for protein spots analyzed in thrombectomy study.

| Gel Spot | ExPASy SWISS 2D PAGE database ID* | Mascot Identification | Mowse score | % Sequence Coverage |
|---|---|---|---|---|
| 64 | Ig heavy chain gamma | Ig gamma-4 Chain C | 84 | 3% |
| 65 | Ig heavy chain gamma | Unidentified | n/a | n/a |
| Protein spots with greater than 200% increased intensity in ischemic blood samples | | | | |
| 46 | Hemoglobin subunit beta | Hemoglobin beta | 178 | 32% |
| 47 | Hemoglobin subunit beta | Hemoglobin beta | 328 | 52% |
| 57 | Hemoglobin subunit alpha | Unidentified | n/a | n/a |
| 23 | Fibrinogen | Vitamin D-binding protein precursor | 67 | 12% |
| 25 | Fibrinogen | Fibrin gamma fragment | 188 | 70% |
| 39 | Transthyretin | Haptoglobin related protein precursor | 60 | 9% |
| 42 | Transthyretin | Transthyretin Chain A amyloidogenic variant | 117 | 21% |
| 44 | Haptoglobin | Haptoglobin Hp2 | 113 | 12% |
| 59 | No spot present, potentially Complement Factor B or Plasminogen | PRO1400 (serotransferrin) | 103 | 6% |

Figure 6:
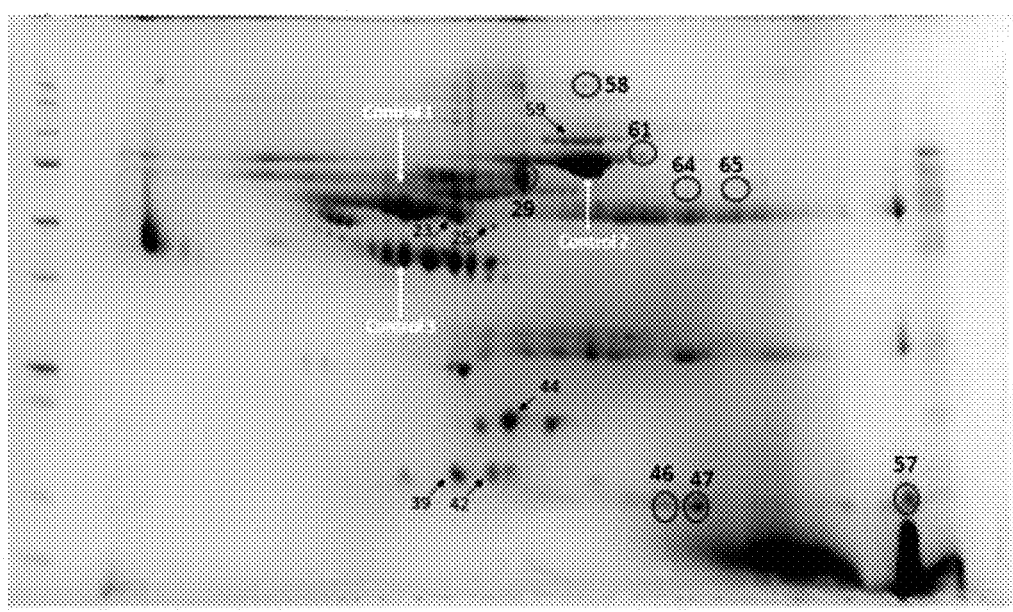
FIG. 6 is a map of protein spots picked for analysis. A 2D Coomassie-stained gel is shown to indicate protein spot mapping. Spots 29, 58, 61, 64, 65 had statistically different intensities in ischemic blood compared with circulating blood samples. Spots 46, 47, 57 had >200% increased intensity in ischemic blood, but were not significantly different from the intensity measured in the circulating blood samples.
Figure 7A:
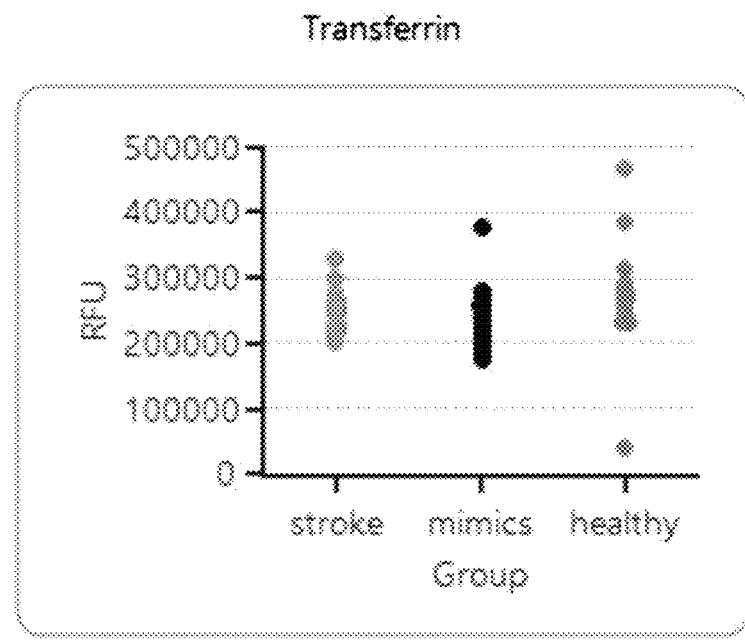
FIG. 7A shows comparison of serum protein concentrations between stroke, stroke-mimicking, and healthy patients for proteins identified by 2D gel analysis of thrombectomy patients. RFUs for transferrin, albumin and haptoglobin were statistically different (p≤0.05) by the Kruskal-Wallis test when comparing stroke patients to stroke-mimicking (mimic) patients and healthy individuals. RFU=relative fluorescent units.
Figure 7B:
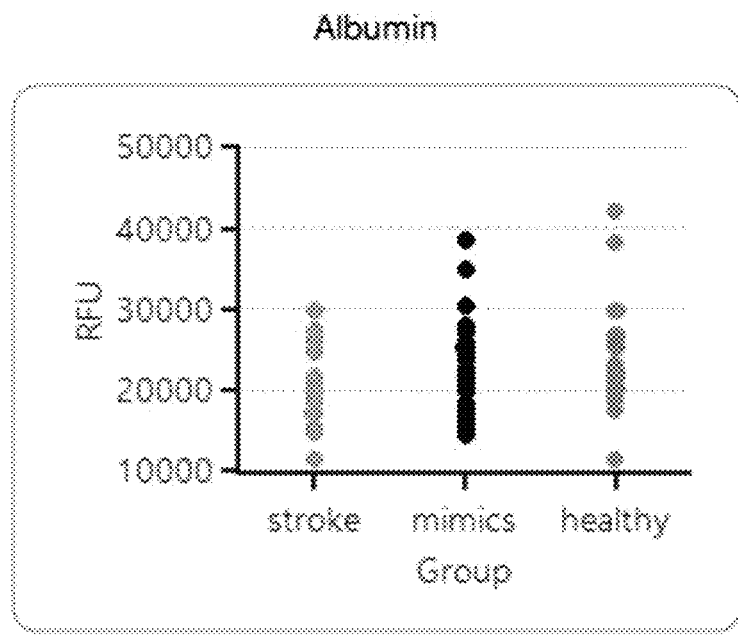
FIG. 7B shows comparison of serum protein concentrations between stroke, stroke-mimicking, and healthy patients for proteins identified by 2D gel analysis of thrombectomy patients. RFUs for transferrin, albumin and haptoglobin were statistically different (p≤0.05) by the Kruskal-Wallis test when comparing stroke patients to stroke-mimicking (mimic) patients and healthy individuals. RFU=relative fluorescent units.
Figure 7C:
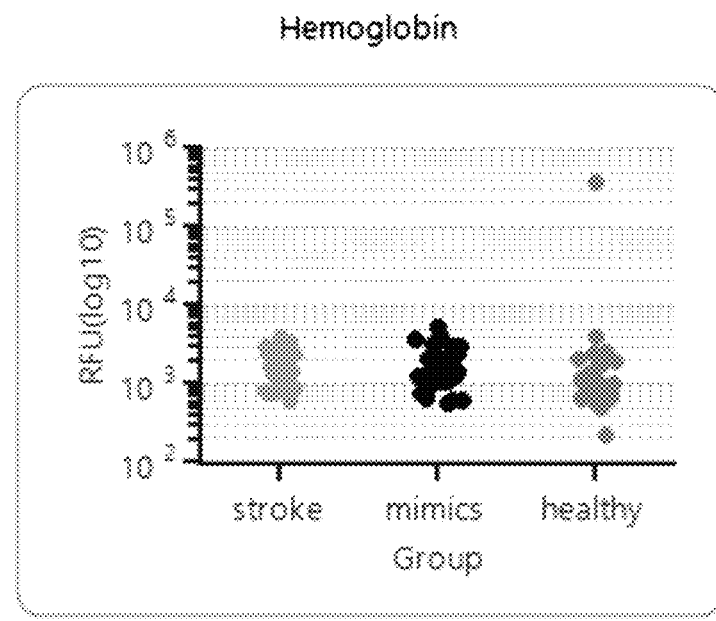
FIG. 7C shows comparison of serum protein concentrations between stroke, stroke-mimicking, and healthy patients for proteins identified by 2D gel analysis of thrombectomy patients. RFUs for transferrin, albumin and haptoglobin were statistically different (p≤0.05) by the Kruskal-Wallis test when comparing stroke patients to stroke-mimicking (mimic) patients and healthy individuals. RFU=relative fluorescent units.
Figure 7D:
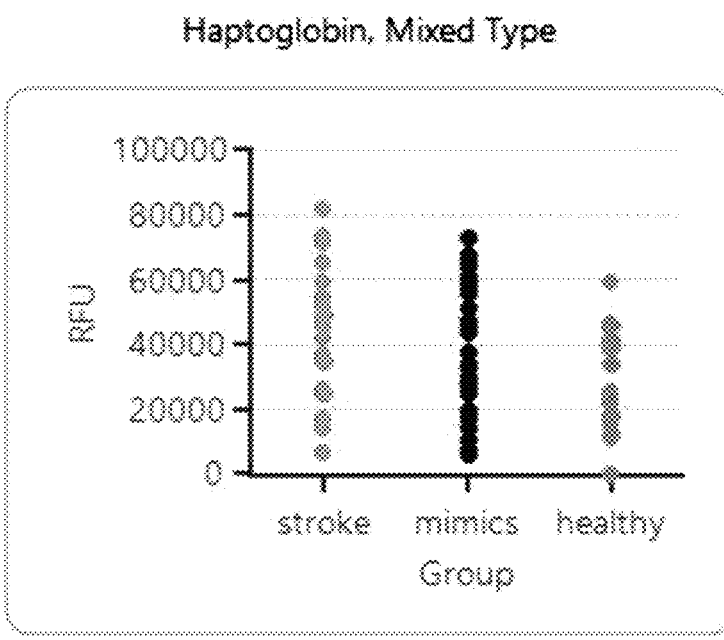
FIG. 7D shows comparison of serum protein concentrations between stroke, stroke-mimicking, and healthy patients for proteins identified by 2D gel analysis of thrombectomy patients. RFUs for transferrin, albumin and haptoglobin were statistically different (p≤0.05) by the Kruskal-Wallis test when comparing stroke patients to stroke-mimicking (mimic) patients and healthy individuals. RFU=relative fluorescent units.
Figure 7E:
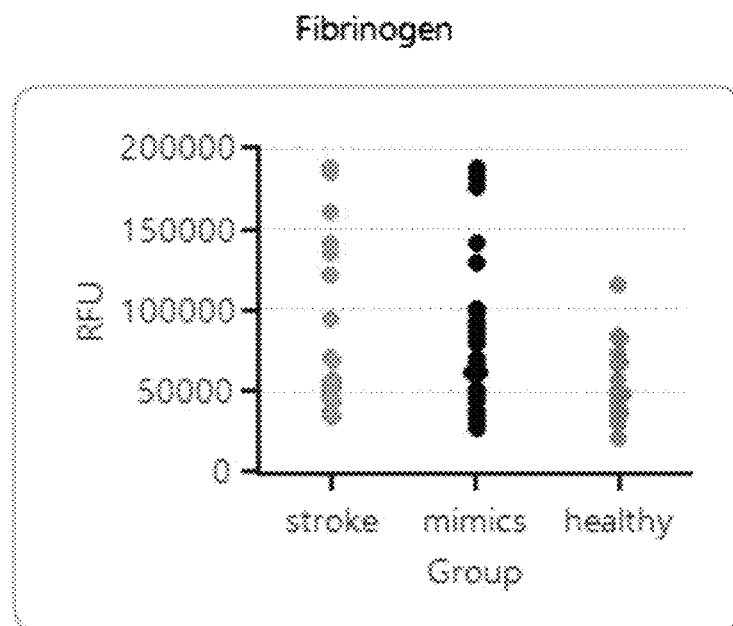
FIG. 7E shows comparison of serum protein concentrations between stroke, stroke-mimicking, and healthy patients for proteins identified by 2D gel analysis of thrombectomy patients. RFUs for transferrin, albumin and haptoglobin were statistically different (p≤0.05) by the Kruskal-Wallis test when comparing stroke patients to stroke-mimicking (mimic) patients and healthy individuals. RFU=relative fluorescent units.
Figure 7F:
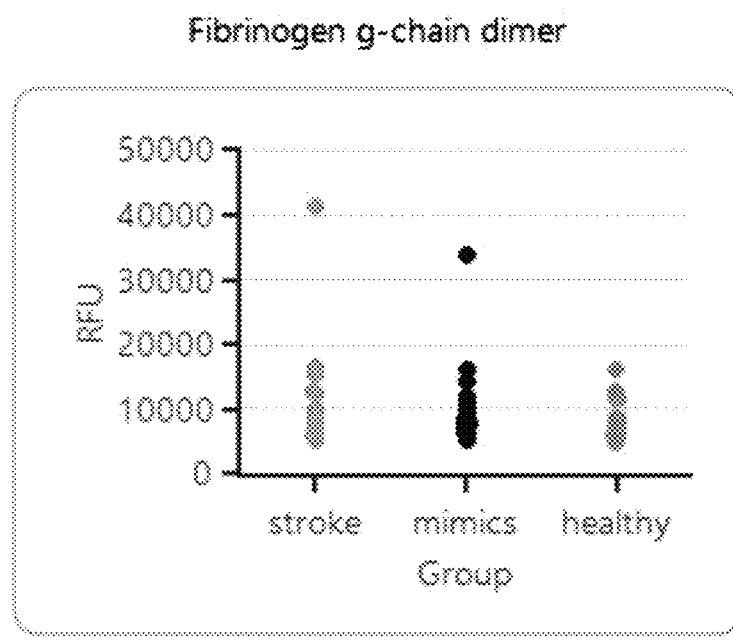
FIG. 7F shows comparison of serum protein concentrations between stroke, stroke-mimicking, and healthy patients for proteins identified by 2D gel analysis of thrombectomy patients. RFUs for transferrin, albumin and haptoglobin were statistically different (p≤0.05) by the Kruskal-Wallis test when comparing stroke patients to stroke-mimicking (mimic) patients and healthy individuals. RFU=relative fluorescent units.

Gel Spot number is annotated in FIG. 6. Protein spots were identified using either 2D PAGE database or MALDI-TOF/TOF mass spectrometry. The Mowse score is the probability-based score for protein identification: a high score denotes a low probability that the sequence's identification is due to chance. All scores listed in the table met the threshold of significance set by the MASCOT algorithm.

A Pearson correlation analysis showed that NUBS scores were correlated with age and sixteen of the protein spots analyzed by 2D DIGE (Table 5). The heat map profile for Patient 4, who had the highest age and stroke severity score of the cohort, showed several proteins with a more extreme percent change in abundance than that seen in the other patients. There was no apparent relationship between the percent change in abundance and the other patient parameters including treatment with tPA and the location of the occluded artery. Three of the nine patients received tPA, yet there is no pattern in these patients' heat map profiles that suggests tPA treatment changes protein expression. The one patient with a basilar artery occlusion also had no outstanding changes in her heat map profile when compared to that of patients with middle cerebral artery occlusions.

TABLE 5

Pearson correlation analysis for NIHSS score, age and the 75 protein spots analyzed for nine thrombectomy patients
Correlation of NIHSS score to age and protein spots

| | AGE | Spot 1 | Spot 2 | Spot 3 | Spot 4 | Spot 5 | Spot 6 | Spot 7 | Spot 8 |
|---|---|---|---|---|---|---|---|---|---|
| NIHSS | 0.763 | 0.450 | 0.449 | 0.461 | 0.768 | 0.573 | 0.725 | 0.597 | −0.426 |
| | 0.017 | 0.225 | 0.225 | 0.212 | 0.016 | 0.107 | 0.027 | 0.090 | 0.253 |

| | Spot 9 | Spot 10 | Spot 11 | Spot 12 | Spot 13 | Spot 14 | Spot 15 | Spot 16 | Spot 17 |
|---|---|---|---|---|---|---|---|---|---|
| NIHSS | −0.457 | −0.370 | −0.563 | −0.630 | −0.537 | −0.551 | 0.031 | −0.453 | −0.680 |
| | 0.217 | 0.327 | 0.114 | 0.069 | 0.136 | 0.124 | 0.938 | 0.220 | 0.044 |

| | Spot 18 | Spot 19 | Spot 20 | Spot 21 | Spot 22 | Spot 23 | Spot 24 | Spot 25 | Spot 26 |
|---|---|---|---|---|---|---|---|---|---|
| NIHSS | −0.356 | −0.438 | −0.602 | −0.806 | −0.641 | −0.641 | −0.569 | 0.608 | −0.013 |
| | 0.347 | 0.238 | 0.086 | 0.009 | 0.063 | 0.063 | 0.110 | 0.082 | 0.973 |

| | Spot 27 | Spot 28 | Spot 29 | Spot 30 | Spot 31 | Spot 32 | Spot 33 | Spot 34 | Spot 35 |
|---|---|---|---|---|---|---|---|---|---|
| NIHSS | 0.186 | −0.651 | −0.018 | −0.390 | −0.561 | −0.222 | 0.783 | 0.267 | 0.452 |
| | 0.632 | 0.058 | 0.964 | 0.299 | 0.116 | 0.566 | 0.013 | 0.488 | 0.222 |

| | Spot 36 | Spot 37 | Spot 38 | Spot 39 | Spot 40 | Spot 41 | Spot 42 | Spot 43 | Spot 44 |
|---|---|---|---|---|---|---|---|---|---|
| NIHSS | −0.439 | 0.675 | 0.415 | 0.205 | 0.538 | 0.719 | 0.541 | 0.448 | 0.782 |
| | 0.238 | 0.046 | 0.267 | 0.596 | 0.135 | 0.029 | 0.133 | 0.227 | 0.013 |

| | Spot 45 | Spot 46 | Spot 47 | Spot 48 | Spot 49 | Spot 50 | Spot 51 | Spot 52 | Spot 53 |
|---|---|---|---|---|---|---|---|---|---|
| NIHSS | 0.788 | 0.138 | 0.100 | 0.865 | 0.812 | 0.895 | 0.808 | 0.768 | 0.018 |
| | 0.012 | 0.724 | 0.798 | 0.003 | 0.008 | 0.001 | 0.008 | 0.016 | 0.963 |

| | Spot 54 | Spot 55 | Spot 56 | Spot 57 | Spot 58 | Spot 59 | Spot 60 | Spot 61 | Spot 62 |
|---|---|---|---|---|---|---|---|---|---|
| NIHSS | 0.592 | 0.541 | 0.717 | 0.115 | 0.248 | −0.166 | 0.059 | −0.045 | 0.069 |
| | 0.093 | 0.133 | 0.030 | 0.768 | 0.520 | 0.669 | 0.881 | 0.908 | 0.861 |

TABLE 5-continued

Pearson correlation analysis for NIHSS score, age and the 75
protein spots analyzed for nine thrombectomy patients Correlation of NIHSS score to age and protein spots

|  | Spot 63 | Spot 64 | Spot 65 | Spot 66 | Spot 67 | Spot 68 | Spot 69 | Spot 70 | Spot 71 |
|---|---|---|---|---|---|---|---|---|---|
| NIHSS | 0.376 | 0.591 | 0.338 | −0.303 | 0.072 | 0.111 | −0.131 | −0.388 | −0.264 |
|  | 0.319 | 0.094 | 0.374 | 0.427 | 0.854 | 0.775 | 0.737 | 0.302 | 0.492 |

|  | Spot 72 | Spot 73 | Spot 74 | Spot 75 |
|---|---|---|---|---|
| NIHSS | −0.323 | −0.044 | −0.254 | 0.695 |
|  | 0.396 | 0.910 | 0.510 | 0.038 |

Correlation of age to NIHSS score and protein spots

|  | NIHSS | Spot 1 | Spot 2 | Spot 3 | Spot 4 | Spot 5 | Spot 6 | Spot 7 | Spot 8 |
|---|---|---|---|---|---|---|---|---|---|
| AGE | 0.763 | 0.373 | 0.237 | 0.231 | 0.469 | 0.656 | 0.658 | 0.519 | −0.389 |
|  | 0.017 | 0.323 | 0.540 | 0.550 | 0.203 | 0.055 | 0.054 | 0.152 | 0.301 |

|  | Spot 9 | Spot 10 | Spot 11 | Spot 12 | Spot 13 | Spot 14 | Spot 15 | Spot 16 | Spot 17 |
|---|---|---|---|---|---|---|---|---|---|
| AGE | 0.132 | 0.170 | 0.028 | −0.094 | −0.070 | −0.147 | 0.557 | 0.194 | −0.299 |
|  | 0.736 | 0.662 | 0.943 | 0.811 | 0.858 | 0.706 | 0.119 | 0.618 | 0.435 |

|  | Spot 18 | Spot 19 | Spot 20 | Spot 21 | Spot 22 | Spot 23 | Spot 24 | Spot 25 | Spot 26 |
|---|---|---|---|---|---|---|---|---|---|
| AGE | −0.006 | −0.500 | −0.416 | −0.708 | −0.312 | −0.178 | −0.081 | 0.627 | −0.347 |
|  | 0.989 | 0.171 | 0.265 | 0.033 | 0.414 | 0.647 | 0.837 | 0.071 | 0.361 |

|  | Spot 27 | Spot 28 | Spot 29 | Spot 30 | Spot 31 | Spot 32 | Spot 33 | Spot 34 | Spot 35 |
|---|---|---|---|---|---|---|---|---|---|
| AGE | 0.262 | −0.209 | 0.348 | 0.136 | −0.143 | −0.271 | 0.671 | 0.276 | 0.125 |
|  | 0.496 | 0.589 | 0.358 | 0.726 | 0.713 | 0.481 | 0.048 | 0.473 | 0.749 |

|  | Spot 36 | Spot 37 | Spot 38 | Spot 39 | Spot 40 | Spot 41 | Spot 42 | Spot 43 | Spot 44 |
|---|---|---|---|---|---|---|---|---|---|
| AGE | −0.109 | 0.434 | −0.137 | −0.124 | 0.242 | 0.163 | 0.081 | 0.242 | 0.393 |
|  | 0.779 | 0.244 | 0.726 | 0.751 | 0.530 | 0.676 | 0.836 | 0.531 | 0.295 |

|  | Spot 45 | Spot 46 | Spot 47 | Spot 48 | Spot 49 | Spot 50 | Spot 51 | Spot 52 | Spot 53 |
|---|---|---|---|---|---|---|---|---|---|
| AGE | 0.249 | −0.202 | −0.022 | 0.396 | 0.288 | 0.518 | 0.509 | 0.635 | −0.241 |
|  | 0.518 | 0.602 | 0.954 | 0.292 | 0.452 | 0.153 | 0.162 | 0.066 | 0.532 |

|  | Spot 54 | Spot 55 | Spot 56 | Spot 57 | Spot 58 | Spot 59 | Spot 60 | Spot 61 | Spot 62 |
|---|---|---|---|---|---|---|---|---|---|
| AGE | 0.296 | 0.679 | 0.618 | −0.273 | 0.757 | −0.262 | −0.113 | 0.492 | 0.411 |
|  | 0.439 | 0.045 | 0.076 | 0.477 | 0.018 | 0.497 | 0.772 | 0.178 | 0.272 |

|  | Spot 63 | Spot 64 | Spot 65 | Spot 66 | Spot 67 | Spot 68 | Spot 69 | Spot 70 | Spot 71 |
|---|---|---|---|---|---|---|---|---|---|
| AGE | 0.436 | 0.719 | 0.502 | 0.113 | 0.220 | 0.413 | 0.319 | 0.015 | 0.155 |
|  | 0.241 | 0.029 | 0.168 | 0.772 | 0.569 | 0.269 | 0.403 | 0.970 | 0.690 |

|  | Spot 72 | Spot 73 | Spot 74 | Spot 75 |
|---|---|---|---|---|
| AGE | 0.209 | 0.355 | −0.076 | 0.342 |
|  | 0.589 | 0.348 | 0.845 | 0.368 |

The upper cell under the spot number is the correlation coefficient.
The lower cell is the p-value.

For those proteins identified from 2D gel analyses which are available on the SOMAscan assay, measurements were compared using the Kruskal-Wallis test on a cohort of 22 stroke patients, 32 stroke-mimicking patients, and 26 healthy patients (Table 6). Albumin and transferrin, two of the proteins found to have a statistical difference between ischemic and circulating blood, also had a statistical difference when comparing stroke and non-stroke groups ($p=0.025$ and $p=0.026$, respectively). Hemoglobin had an average percent change >300% between ischemic and circulating blood, but was not statistically significant between stroke and non-stroke groups ($p=0.052$). Haptoglobin was not statistically different between ischemic and circulating blood in the gel analysis but was statistically different in peripheral blood from stroke and non-stroke groups ($p=0.012$). Scatter plots for these proteins (FIGS. 7A-7F) show a large overlap in the range of measurements between the stroke, mimic, and healthy groups.

TABLE 6

Comparison of candidate biomarker proteins identified in the thrombectomy study between peripheral blood of stroke, stroke-mimicking, and healthy patients from a different patient cohort.

| Target | p | q | H | Mean ± SD | | |
|---|---|---|---|---|---|---|
| | | | | stroke | mimics | healthy |
| Transferrin | 0.026 | 0.114 | 7.3 | 246,331 ± 29,464 | 235,142 ± 36,141 | 258,726 ± 68,995 |
| Albumin | 0.025 | 0.110 | 7.4 | 20,004 ± 4,489 | 21,426 ± 5,995 | 240,010 ± 6,221 |
| Hemoglobin | 0.052 | 0.177 | 5.9 | 1,951 ± 981 | 1,760 ± 1,054 | 14,915 ± 69,609 |
| Haptoglobin, Mixed Type | 0.012 | 0.070 | 8.9 | 43,918 ± 19,961 | 40,685 ± 18,653 | 29,394 ± 14,701 |
| Fibrinogen | 0.062 | 0.199 | 5.6 | 80,420 ± 50,665 | 76,544 ± 43,988 | 53,642 ± 21,127 |
| Fibrinogen g-chain dimer | 0.080 | 0.234 | 5.1 | 10,737 ± 7,515 | 9,597 ± 5,048 | 7,940 ± 2,519 |

The large patient-to-patient variability seen in the 2D-DIGE experiments may result from a number of factors. These include the heterogeneity of stroke and the diversity of patient characteristics in a small sample size. The correlation analysis supported a relationship between NUBS score and the abundance of 16 proteins, making these proteins potential biomarkers of stroke severity. There was no obvious relationship between protein abundance and tPA treatment or infarct location. Therefore, variability in protein abundances may be due to a patient clinical parameter that was not documented.

Some patients showed a large fold change in abundance for protein spots 46, 47, and 57 between their ischemic and circulating blood. These spots were identified as isoforms of hemoglobin, and their increased abundance in the ischemic blood may be indicative of low blood oxygen levels or hemolyzed blood samples. Although the average protein abundances of these protein spots for all nine patients were not statistically significant, the inclusion of these proteins in a stroke biomarker panel may still be useful. For example, a significant increase in hemoglobin in such a biomarker panel may be indicative of stroke.

Five protein spots had statistically significant differences in abundance between ischemic and circulating blood. Interestingly, these proteins were less abundant in the ischemic area. All of the identified proteins are common blood proteins—albumin, transferrin, immunoglobulin gamma. Since these proteins are not 'brain-specific', this could be indicative of systemic changes following or preceding stroke. The concept of a systemic manifestation has been demonstrated in previous stroke studies. Systemic inflammation is commonly associated with cerebrovascular disease, and an impaired glucose metabolism has also been linked to this disease When the proteins identified as stroke biomarker candidates were measured in peripheral blood in a new cohort of patients, albumin, transferrin, and haptoglobin were found to be statistically significant between stroke, stroke-mimicking, and healthy groups. However, the scatter plots of these proteins were highly overlapping between the patient groups. This suggested the individual proteins would exhibit a low sensitivity and specificity for stroke diagnosis, and therefore would have little relevance in a clinical setting.

A portion of the transferrin protein in pooled serum samples was found to have a shift in molecular weight. The ischemic gel showed one spot of transferrin and the control gel showed the equivalent spot but also revealed a smaller second spot directly above it. Spots in both locations were identified as serotransferrin via a MASCOT database search, suggesting there was some change in post-translational modifications occurring in the protein due to the stroke. This shift in molecular weight could indicate a change in protein glycosylation, or the presence of a serotransferrin isoform.

Transferrin is secreted into the blood by the liver. Thus, it is expected to be present in the circulating blood. This protein has two isoforms: beta-1-transferrin is the isoform found in most body fluids while the de-sialated form beta-2-transferrin, also known as tau protein, is thought to be found only in cerebral spinal fluid (CSF). The defining modification of beta-2-transferrin is the removal of sialic acid by neuraminidase in the CSF. This modification allows the protein to be detected on a 1-dimensional gel as a distinct band above the beta-1 transferrin band. Because the beta-2 isoform normally is not found in the serum, the secondary higher-molecular-weight protein spot would not be expected to be transferrin; however more information is needed to confirm this. The lack of this protein in the ischemic blood was an interesting and unexpected finding that suggests the modification was removed (i.e., the sialic acid was added or the glycosylation was removed) in the ischemic condition. Because of the nature of a pooled experiment, it cannot be determined whether this protein was expressed in one, several, or all of the stroke patient's circulating blood. Referring back to the individual patients' 2D DIGE gels, the transferrin protein spot did appear to be divided in a few of the gels. However, due to over-saturated image intensity of the primary transferrin protein spot, the presence of this secondary transferrin spot in all patients' gels was inconclusive.

There were many differences between the proteins in ischemic and circulating serum. A high amount of variability was seen in the 2D DIGE gels of the patients. Nonetheless, albumin, transferrin, and immunoglobulin gamma protein spots were significantly higher in the circulating blood serum, and hemoglobin had a large fold change in abundance in the ischemic blood serum of a few patients. When the concentrations of these proteins were compared in peripheral blood in a different cohort of patients, the individual proteins did not appear to have much clinical utility as stroke biomarkers.

Example II

As described above blood from ischemic stroke patients with large vessel occlusions was analyzed. Blood from the ischemic core of patients undergoing mechanical thrombectomy was compared to their own circulating arterial blood to determine if significant changes in protein abundance occurred in the ischemic area. A few blood proteins were identified with statistically different abundances in the ischemic blood sample, but when the concentrations of these proteins were compared in a new cohort of patients, the scatter plots of these proteins were highly overlapping between stroke and non-stroke patients. The proteins did not appear to have much clinical relevance as potential stroke biomarkers, and therefore the search for biomarker candidates continues.

According to another example, the venous blood of stroke patients was compared to that of healthy patients to find stroke-induced protein changes. The main goal was to determine which proteins were uniquely expressed, not expressed, or differentially expressed in the blood of stroke patients when compared to controls using two approaches.

In the first approach, 2D gel analysis was used to visualize overall differences in protein patterns between pooled serum from stroke patients and pooled serum from healthy patients. In short, equal amounts of serum proteins from five stroke patients in their sixth decade of life were pooled and separated via 2D gel electrophoresis, and the same was done for 5 healthy patients of the same age group. This experiment was then repeated with patients in their fifth decade of life. A survey of Get With The Guidelines Stroke database found that 24.9% of stroke victims are aged 70-79, 18.9% are aged 60-69, and 13.7% are aged 50-59. Thus, patients within the selected ages of 50-69 represent nearly a third of stroke victims. From the 22 stroke and 26 healthy samples, 5 patients from both stroke and healthy groups with similar age, sex, and race distributions were selected.

In the second approach, to identify lower-abundance blood proteins that are significantly different between the stroke and healthy groups (age-50 and age-60 cohorts combined), the measurements from the SOMAscan 1310-protein assay were analyzed using univariate analyses. Biomarker candidates identified by this screening process were then evaluated using protein measurements for all stroke and healthy patients (aged 38-90) and then evaluated using protein measurements for all stroke and stroke-mimicking patients (aged 26-90). See above for details on methodology.

Figure 8A:
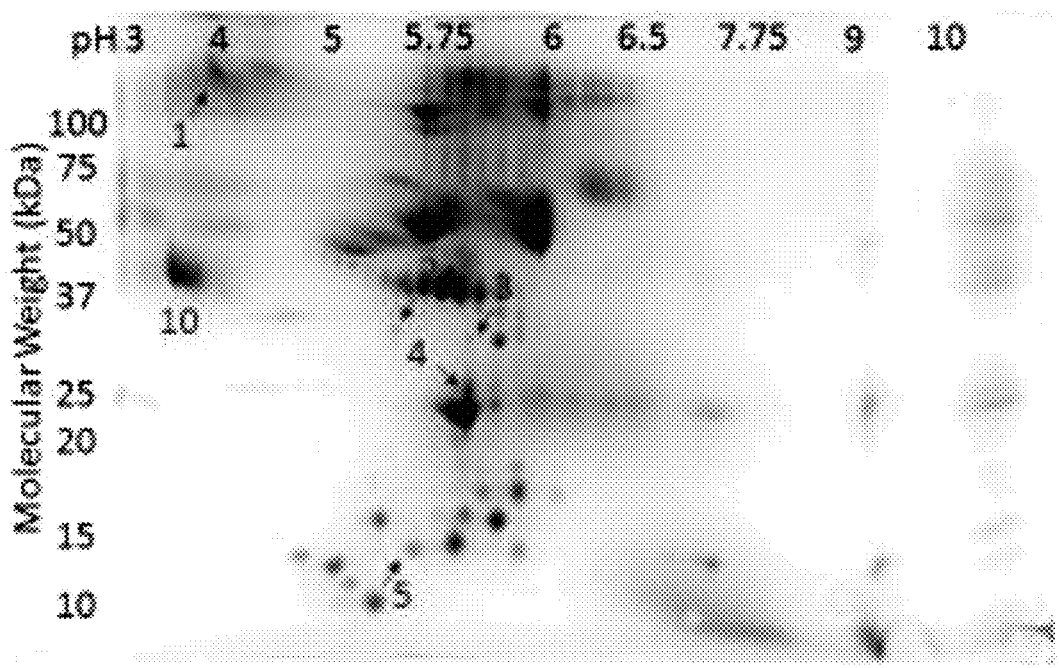
FIG. 8A is a photograph of a 2D gel of pooled stroke serum proteins and pooled control serum proteins from age-60 cohort. Four spots were unique to the gel from healthy patients (Spots 1, 3, 4, 5) and four spots were unique to the gel from stroke patients (Spots 6, 7, 8, 9). The box encloses proteins seen in the age-60 cohort gel which were not seen on the age-50 cohort gel, and are collectively referred to as Spot 15.
Figure 8B:
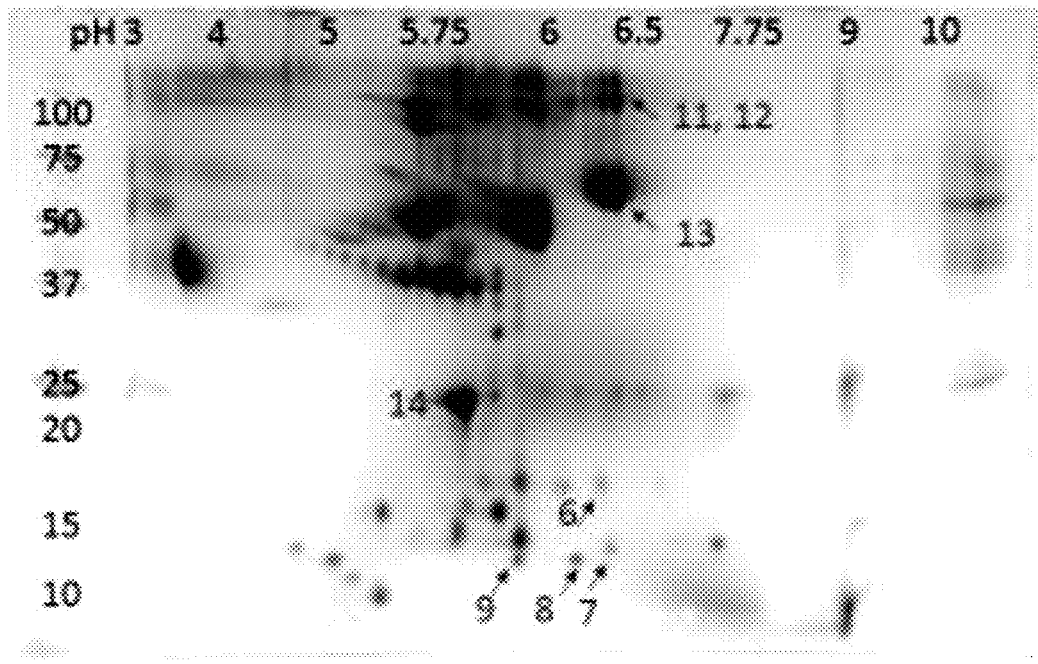
FIG. 8B is a photograph of a 2D gel of pooled stroke serum proteins and pooled control serum proteins from age-60 cohort. Four spots were unique to the gel from healthy patients (Spots 1, 3, 4, 5) and four spots were unique to the gel from stroke patients (Spots 6, 7, 8, 9). The box encloses proteins seen in the age-60 cohort gel which were not seen on the age-50 cohort gel, and are collectively referred to as Spot 15.
Figure 9A:
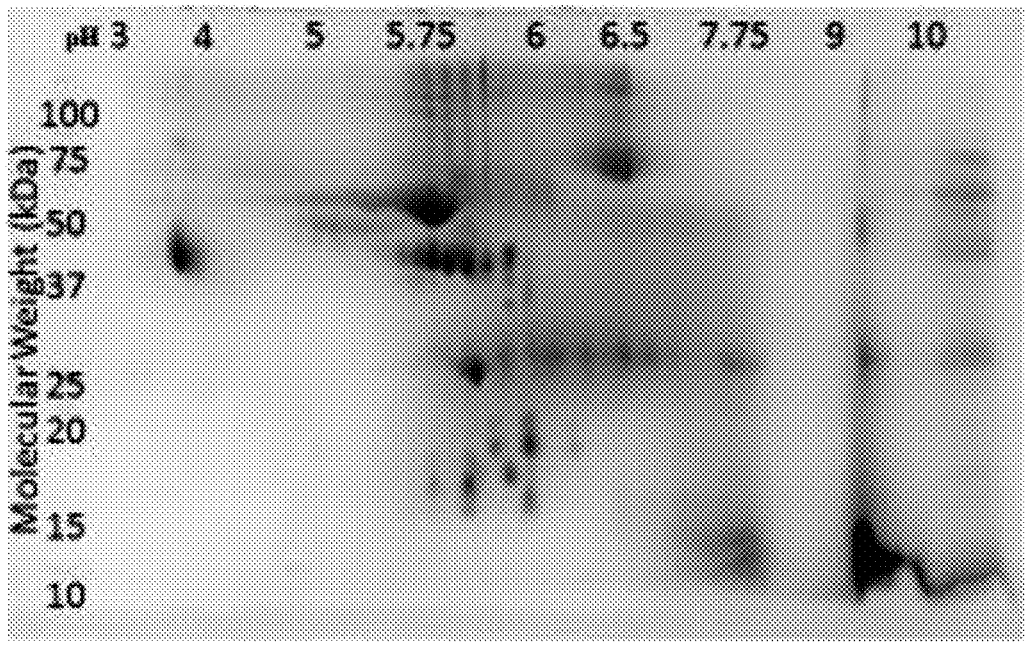
FIG. 9A is a photograph of a 2D gel of pooled stroke serum proteins and pooled control serum proteins from age-50 cohort. Spot 7 was unique to the gel from stroke patients in the age-50 cohort.
Figure 9B:
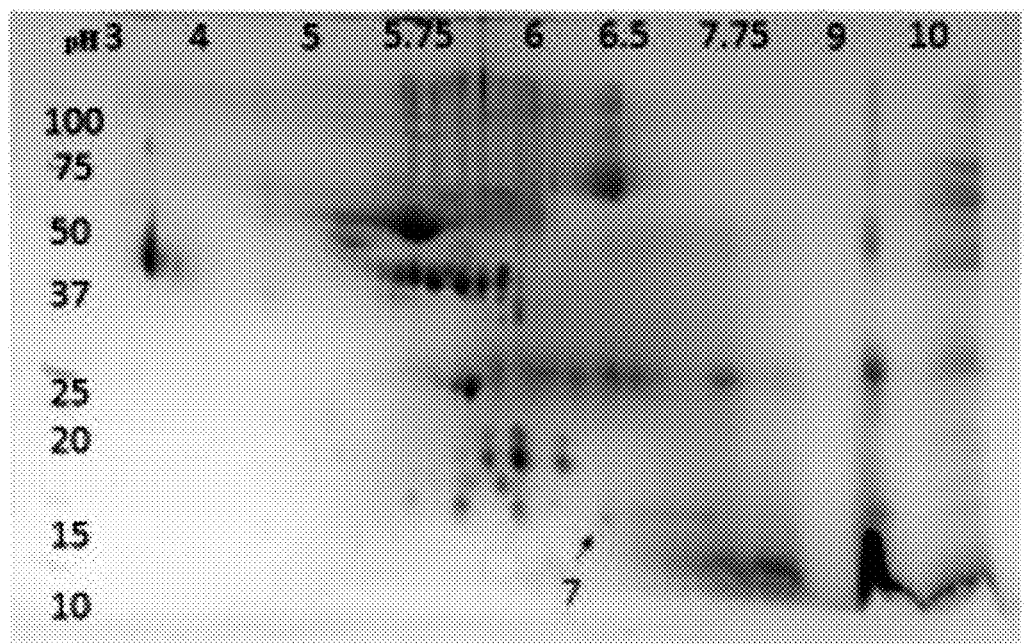
FIG. 9B is a photograph of a 2D gel of pooled stroke serum proteins and pooled control serum proteins from age-50 cohort. Spot 7 was unique to the gel from stroke patients in the age-50 cohort.

To assess major differences in venous blood proteins between stroke patients and healthy patients, the 2D gel of pooled stroke serum proteins was compared to the 2D gel of pooled control serum proteins. When qualitatively comparing the 2D spot patterns between the two pooled samples for the aged-60 cohort, Spots 1, 3, 4, and 5 were unique to the normal gel, and Spots 6, 7, 8, and 9 were unique to the stroke gel (FIGS. 8A and 8B). When comparing the 2D spot patterns between the two pooled samples for the aged-50 cohort, only one protein spot was unique to the stroke gel (FIGS. 9A and 9B, arrow). This protein spot aligns with Spot 7 from the stroke gel for the aged-60 cohort. Of the other unique spots identified on the 2D gels from the aged-60 cohort, Spots 1, 3, 4, 6, 8, and 9 were not seen in the 2D gels of the aged-50 cohort. Only Spot 5 which was present in both the stroke and healthy gel. When comparing gels from the two age groups, there were some spots visible on the gels from the older cohort that were not visible on the gels from the younger cohort. For example, the lower left area of the age-60 gel showed four additional protein spots which were not seen on the age-50 gel (FIGS. 8A and 8B, box).

The protein identities of these spots were determined either by mass spectrometry (Spots 4, 9, 10, 14) or by referencing the SWISS 2D PAGE database human plasma master gel or literature. Additional spots were selected for identification to help spatially align with the 2D PAGE references (Table 7).

TABLE 7

Identifications for protein spots selected from stroke versus healthy comparison.

| Gel Spot | MW (kDa) | pI | Identificataion | Method of identification |
|---|---|---|---|---|
| 1 | >150 | 3-4 | Ceruloplasmin | 2D PAGE spot matching |
| 2 | 25-37 | 5-5.75 | Apolipoprotein J | 2D PAGE spot matching |
| 3 | 25-37 | 5.75-6 | Apolipoprotein E Transthyretin | 2D PAGE spot matching |
| 4 | 20-37 | 5.75-6 | Apolipoprotein A-I | MALDI-TOF MS |
| 5 | 10-15 | 5-5.75 | Transthyretin Haptoglobin | 2D PAGE spot matching |
| 6 | 15-20 | 6-6.5 | Haptoglobin | 2D PAGE spot matching |
| 7 | 10-15 | 6-6.5 | Serum Amyloid A protein | 2D PAGE spot matching |
| 8 | 10-15 | 6-6.5 | Serum Amyloid A protein | 2D PAGE spot matching |
| 9 | 10-15 | 5.75-6 | Serum Amyloid A precursor protein | MALDI-TOF MS |
| 10 | 37-50 | 3-4 | Alpha-1-acid glycoprotein | MALDI-TOF MS |
| 11 | >150 | 6-6.5 | Ig heavy chain | 2D PAGE spot matching |
| 12 | 100-200 | 6-6.5 | Complement factor B Plasminogen | 2D PAGE spot matching |
| 13 | 50-75 | 6-6.5 | Transferrin Ig heavy chain | 2D PAGE spot matching |
| 14 | 20-25 | 5.75-6 | Apolipoprotein A-I | MALDI-TOF MS |
| 15 | 10-15 | 4.5-5.5 | Apolipoproteins C2, C3, A2 | 2D PAGE spot matching |

Gel spots are annotated in FIGS. 8A and 8B. Spots 1, 3, 4, 5 were unique to the gel from healthy patient serum while Spots 6, 7, 8, 9, were unique to the gel from stroke patient serum. Spot 7 was the only spot duplicated in both age cohorts. MW=molecular weight; pI=isoelectric point According to the innovation, biomarker discovery efforts were continued by focusing on lower-abundance blood proteins that are significantly different between stroke and healthy groups (age-50 and age-60 cohorts, combined) using the measurements from the SOMAscan 1310-protein assay. Mann Whitney analyses revealed 195 proteins with p-values less than 0.05. Thirteen proteins were selected as biomarker candidates (Table 8) after the following selection process. To account for proteins with coincidental statistical differences between cohorts of the same population, data from the age-50 healthy cohort was compared to data from the age-60 healthy cohort, and data from the age-50 stroke cohort was compared to data from the age-60 stroke cohort. The proteins from these analyses that had a p-value less than 0.05 and that were also on the original list of 195 proteins were removed from the list of biomarker candidates. There were 19 proteins removed from the list because they were statistically different between the two healthy populations. An additional 7 proteins were removed from the list because they were statistically different between the two stroke populations.

TABLE 8

Thirteen biomarker candidates selected from SOMAscan analysis of stroke and healthy cohorts.

| Protein | p-value |
|---|---|
| BMP-14 | 1.08E−05 |
| LKHA4 | 2.17E−05 |

TABLE 8-continued

Thirteen biomarker candidates selected from SOMAscan analysis of stroke and healthy cohorts.

| Protein | p-value |
| --- | --- |
| Aflatoxin B1 aldehyde reductase | 1.08E−05 |
| C3b | 1.08E−05 |
| GDF2 | 1.08E−05 |
| ERP29 | 1.08E−05 |
| TYK2 | 1.08E−05 |
| iC3b | 4.33E−05 |
| GSK-3 alpha/beta | 0.000325 |
| UB2G2 | 2.17E−05 |
| C5 | 0.000487 |
| M2-PK | 0.000725 |
| PPID | 0.001505 |

Using the SomaLogic SOMAscan assay, serum proteins from 10 stroke patients (age range 50-66 years) were compared to that of 10 healthy patients (age range 51-68 years). Mann Whitney analyses resulted in 195 proteins with $p<0.05$, 13 of which were selected as potential biomarker candidates after removing proteins with age-dependent changes and population-dependent changes. Additionally, proteins that may show an age-dependent change with stroke were removed because a point-of-care diagnostic is likely to be utilized when a person's age is unknown. Therefore, the age-50 stroke cohort was compared to the age-50 healthy cohort and the age-60 stroke cohort was compared to the age-60 healthy cohort. Proteins that were significantly different between stroke and healthy patients in one of the age groups, but not the other, and that were included in the original list of 195 proteins, were taken off the list. There were 169 proteins removed due to suspected age dependence.

In addition to the 13 proteins identified by the SOMAscan assay, the protein identified from the 2D gel analysis as a possible stroke biomarker was included. This Spot 7 was tentatively identified as serum amyloid A protein (SAA). Using the SOMAscan assay data, serum levels of this protein were compared between stroke patients from the age-50+age-60 (combined) cohorts and corresponding controls (all patients described in Table 9) using the Mann Whitney U test.

Figure 10:
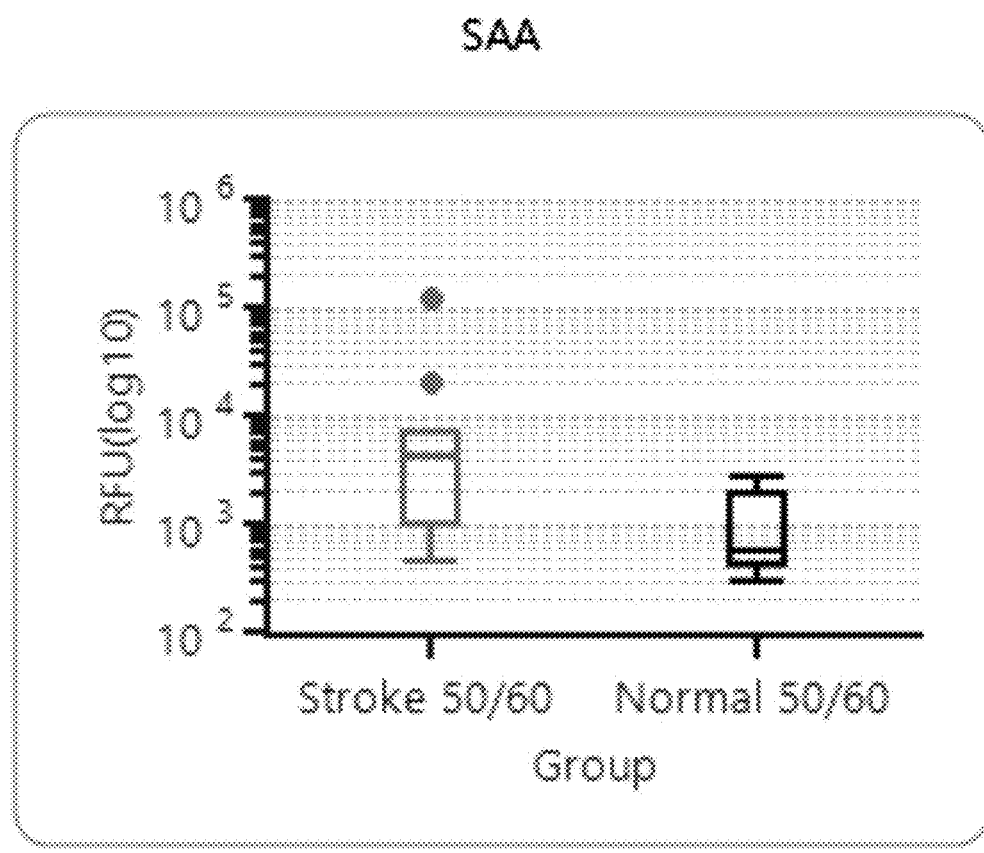
FIG. 10 is a graph depicting comparison of SAA levels in Stroke and Healthy age-50 and age-60 combined cohorts. SAA=Serum Amyloid A; RFU=relative fluorescent units. The interquartile range box represents the middle 50% of data with the whiskers extending to the top and bottom 25%, excluding outliers (dots). The horizontal line represents the median of the data.

A statistically significant difference was seen ($p=0.0089$) (Table 10 and FIG. 10), suggesting elevated levels of SAA is a potential biomarker of ischemic stroke. Interestingly, when the stroke and healthy groups from the age-60 cohort and age-50 cohort were separately compared, SAA was significantly different between stroke and healthy patients for the age-50 group, but not for the age-60 group. However, when analyzing the age-50 and age-60 cohorts together as one cohort, SAA was significantly different between stroke and healthy patients.

TABLE 10

Comparison of SAA levels in Stroke and Healthy age-50 and age-60 combined cohorts.

| | | | | Mean ± SD | |
| --- | --- | --- | --- | --- | --- |
| Target | p | q | U | Stroke Age 50-66 (n = 10) | Healthy Age 51-68 (n = 10) |
| SAA | 0.009 | 0.148 | 84 | 16812.1 ± 37043.3 | 1042.1 ± 906.0 |

Values are the mean ± SD RFU for each cohort.

SAA = Serum Amyloid A; p = p-value; q = false discovery-rate adjusted p-value; U = test statistic for Mann Whitney U test.

Figure 11A:
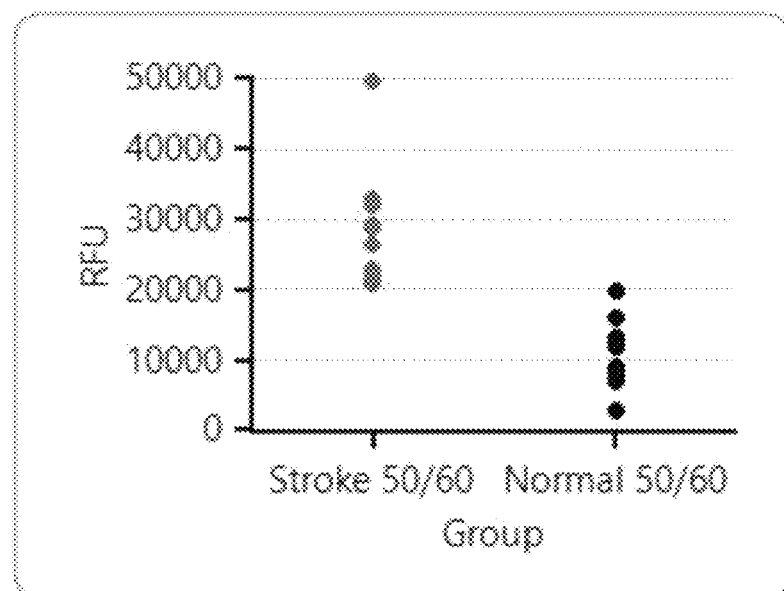
FIG. 11A shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11B:
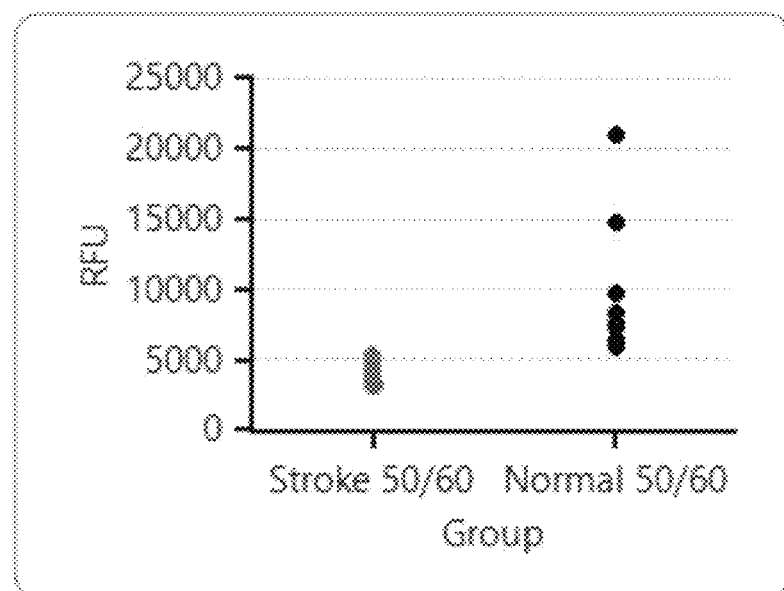
FIG. 11B shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11C:
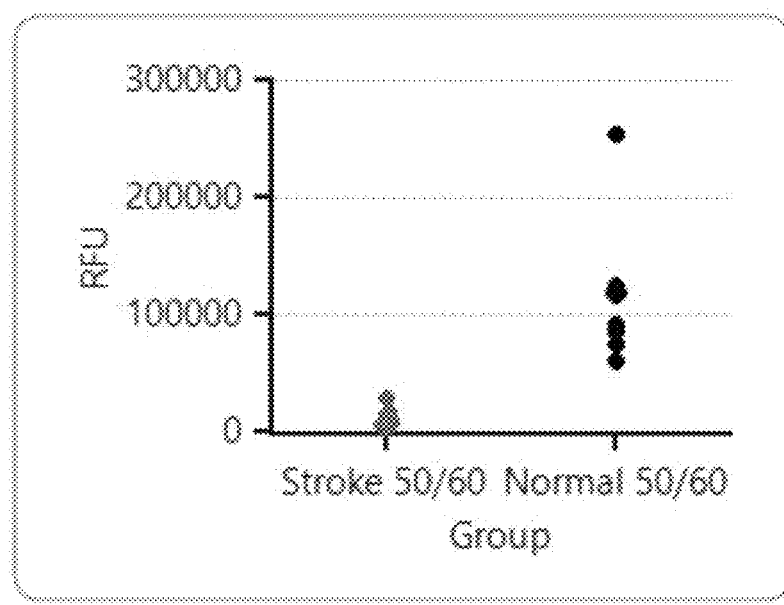
FIG. 11C shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11D:
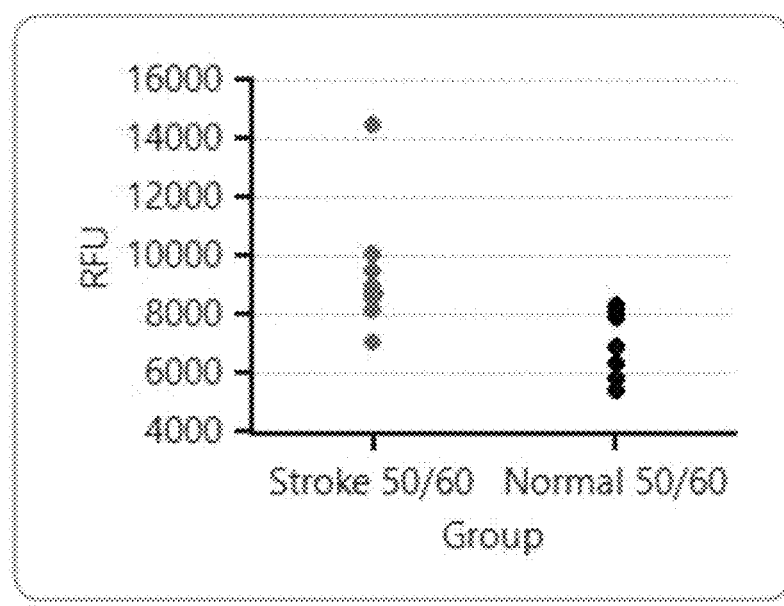
FIG. 11D shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11E:
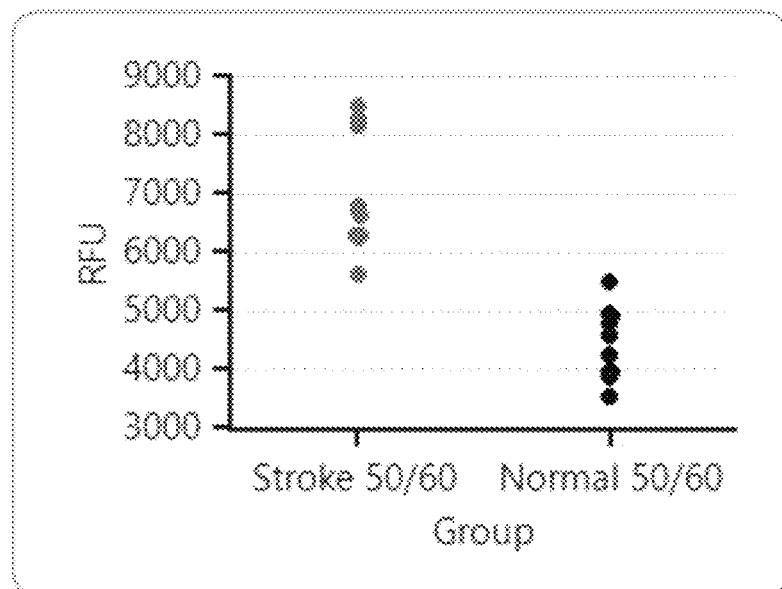
FIG. 11E shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11F:
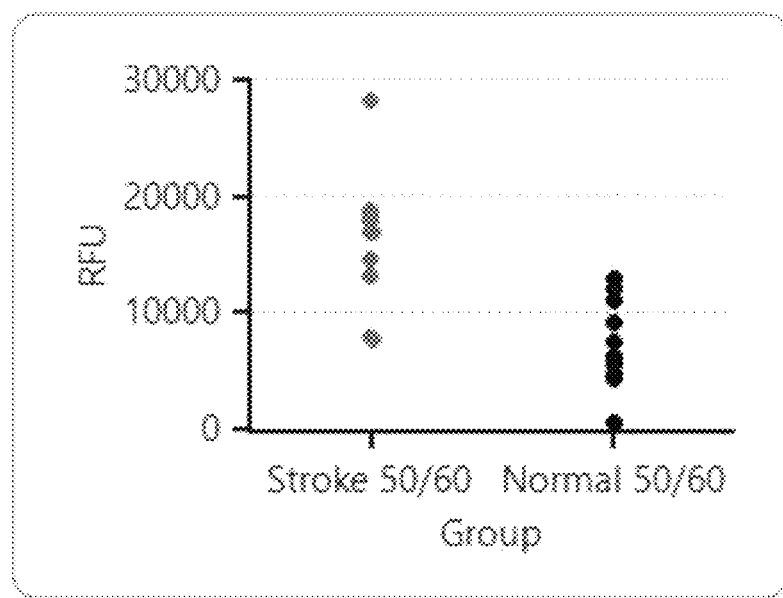
FIG. 11F shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11G:
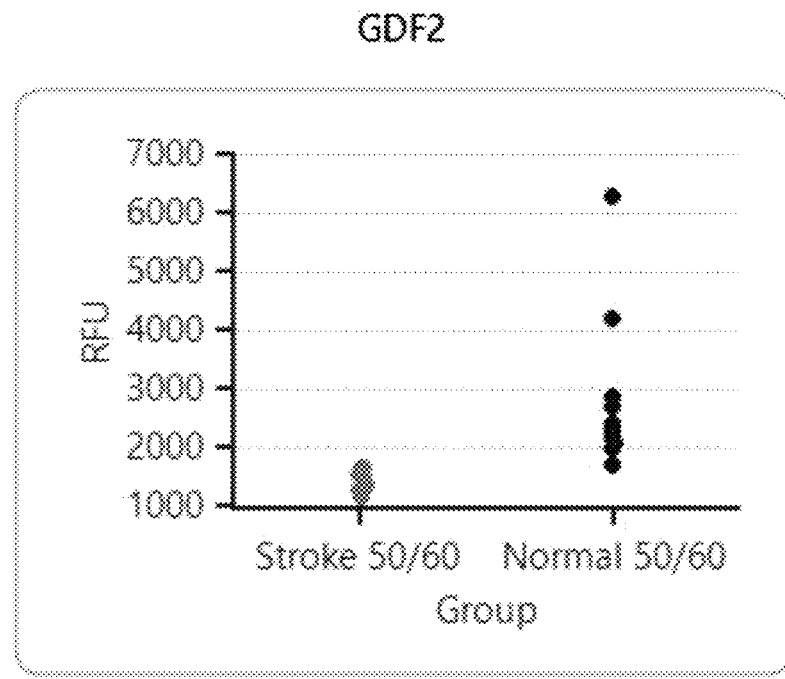
FIG. 11G shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11H:
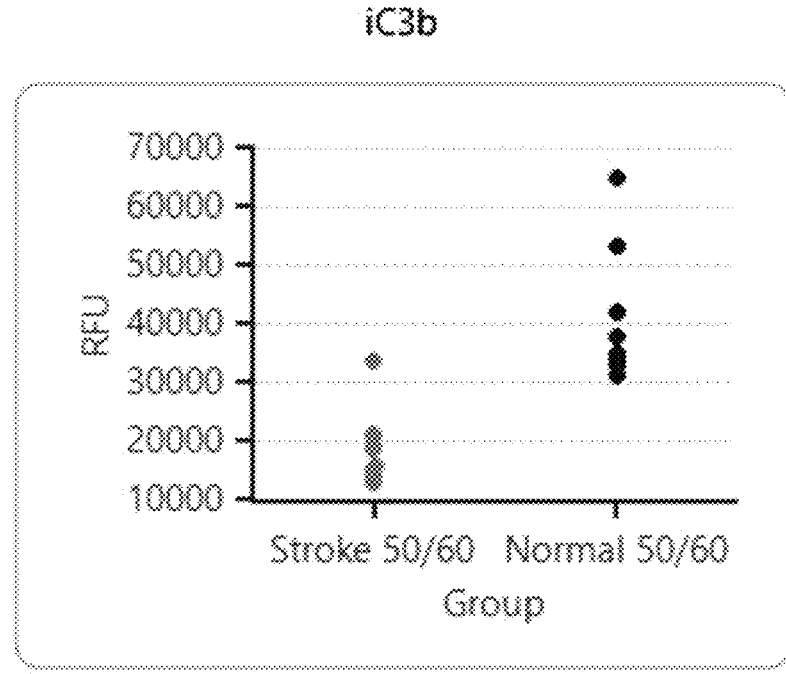
FIG. 11H shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11I:
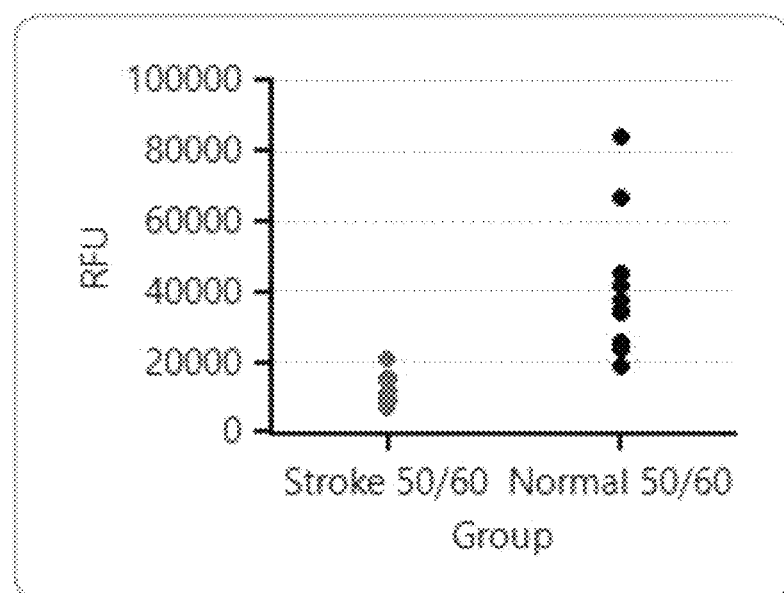
FIG. 11I shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11J:
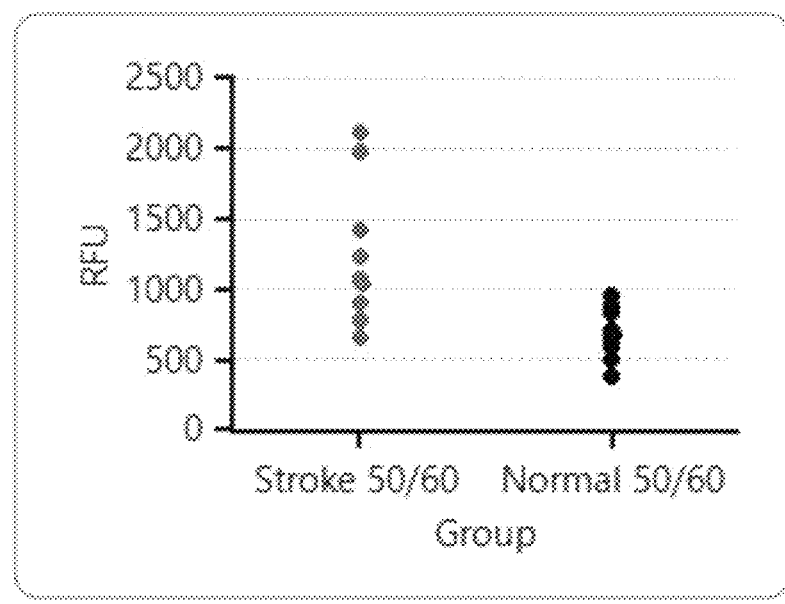
FIG. 11J shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11K:
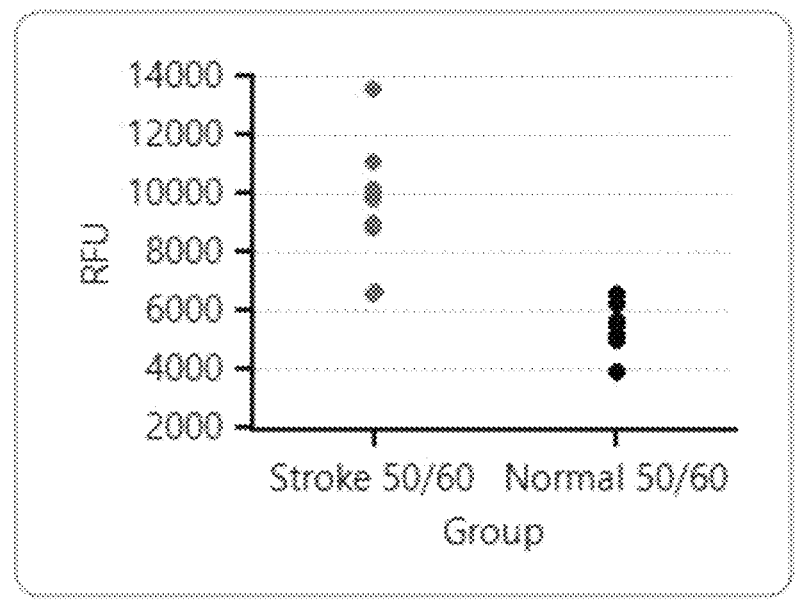
FIG. 11K shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11L:
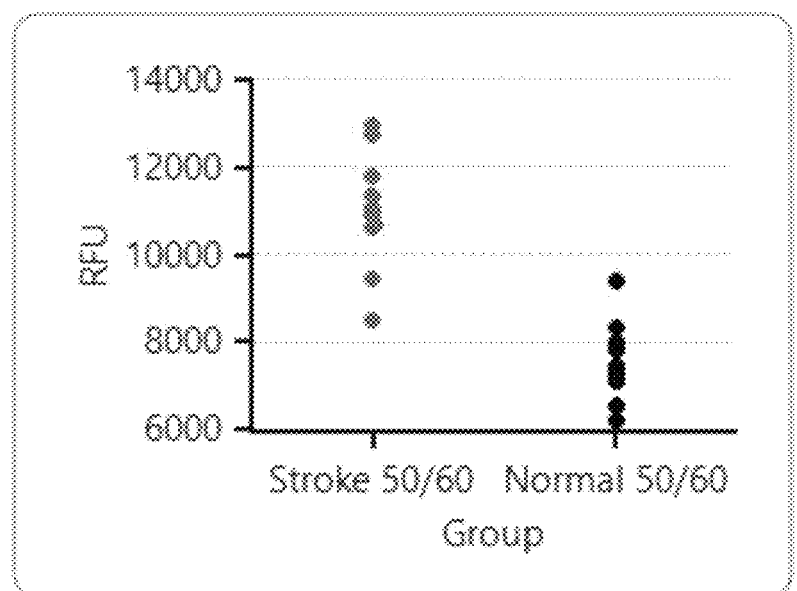
FIG. 11L shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11M:
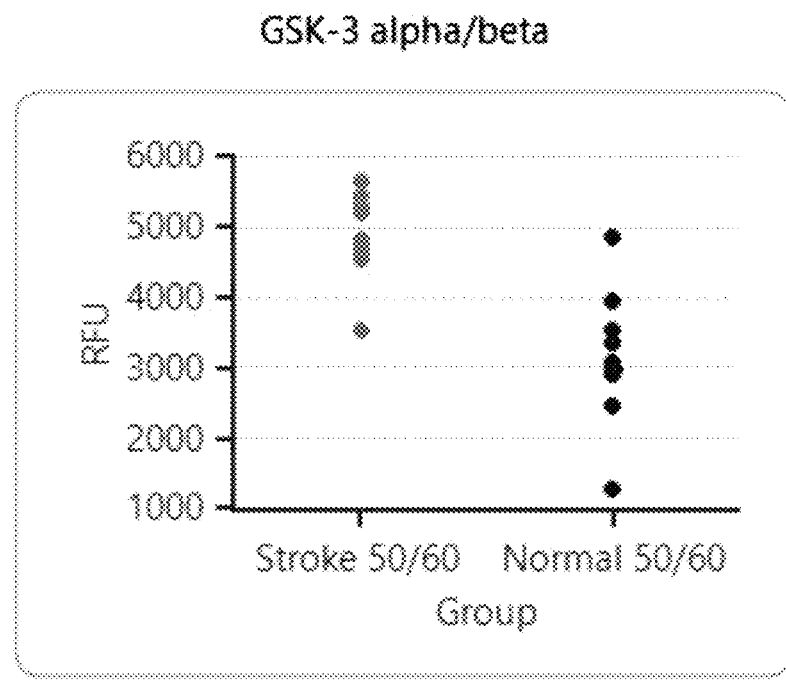
FIG. 11M shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.
Figure 11N:
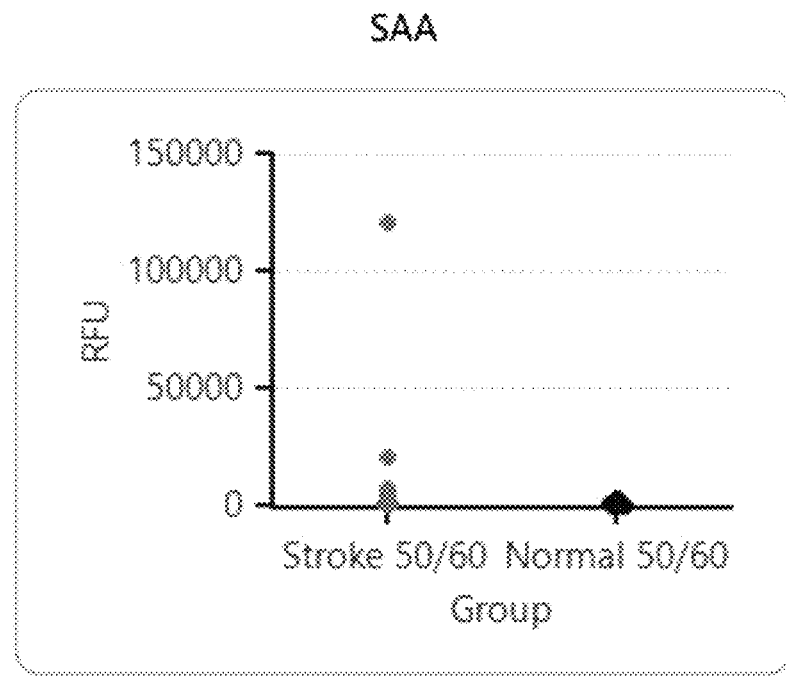
FIG. 11N shows a scatter plot depicting candidate biomarker protein abundances in serum from stroke and healthy patients aged 50-68 years. SOMAscan measurements from 10 stroke patients (age range 50-66 years) and 10 healthy patients (age range 51-68 years). RFU=relative fluorescent units.

Scatter plots for the remaining thirteen proteins and SAA are shown in FIGS. 11A-11N. For nearly every protein, the distribution of relative fluorescent units (RFU) for the stroke patients has minimal overlap with the RFU distribution for the healthy patients. Because of this, threshold values with resulting high diagnostic accuracy could easily be selected to distinguish stroke patients from healthy patients.

Figure 12A:
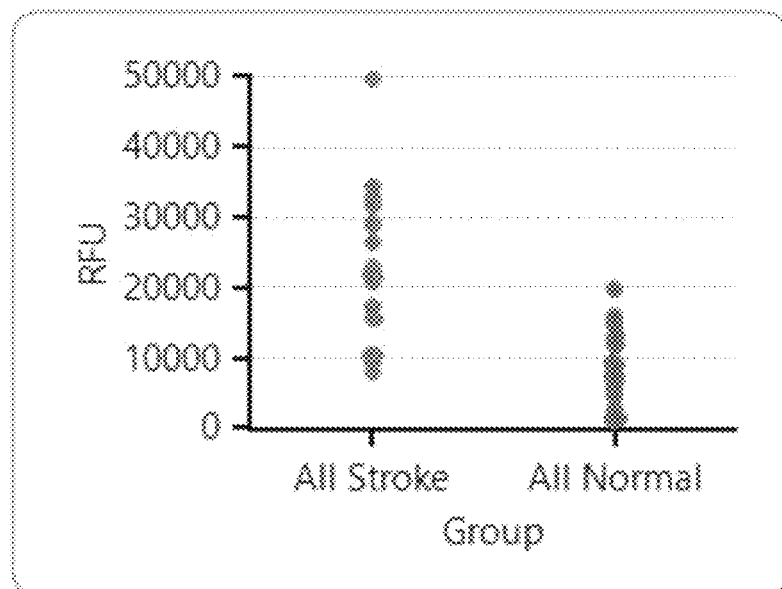
FIG. 12A is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12B:
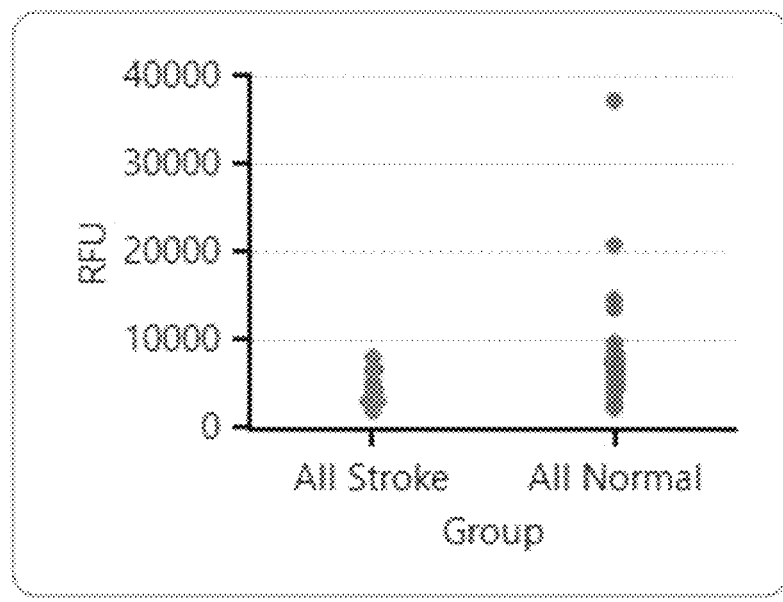
FIG. 12B is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12C:
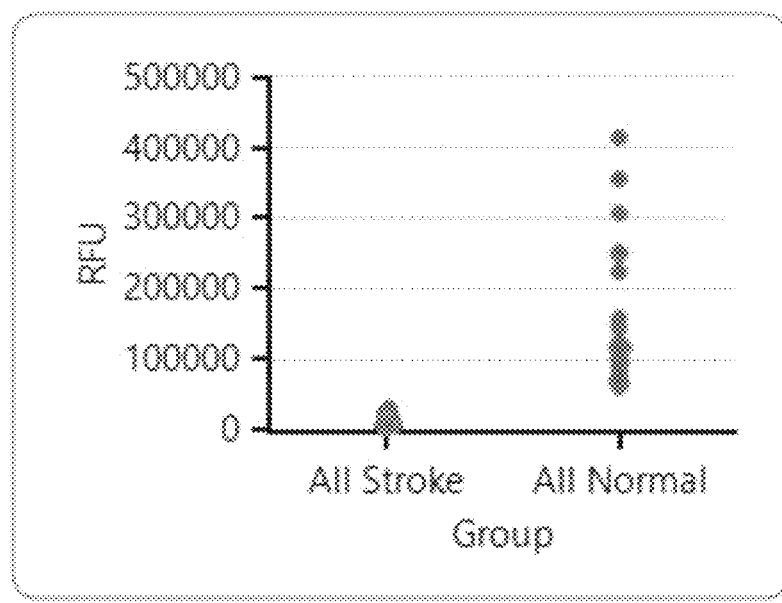
FIG. 12C is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12D:
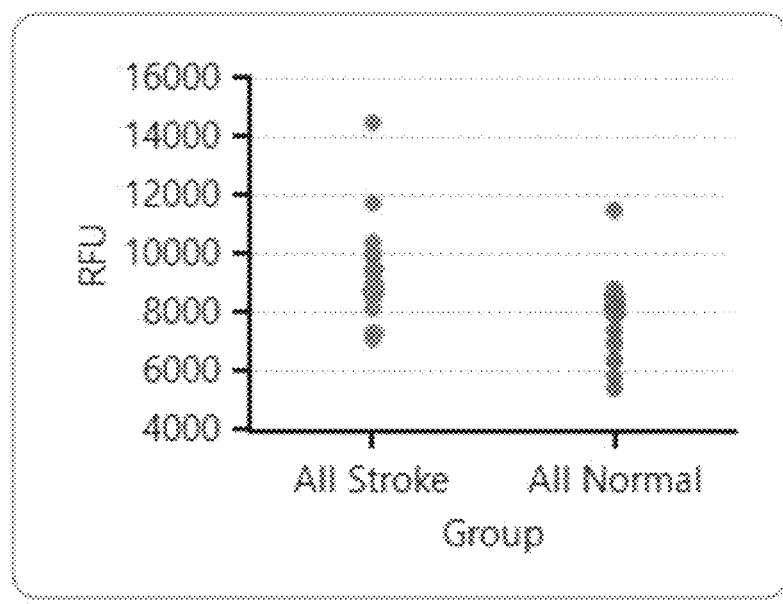
FIG. 12D is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12E:
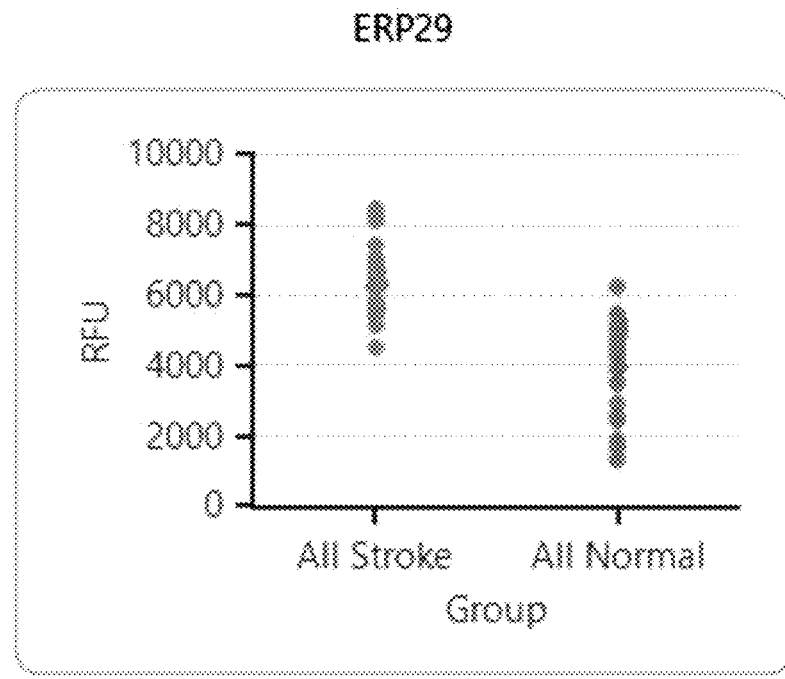
FIG. 12E is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12F:
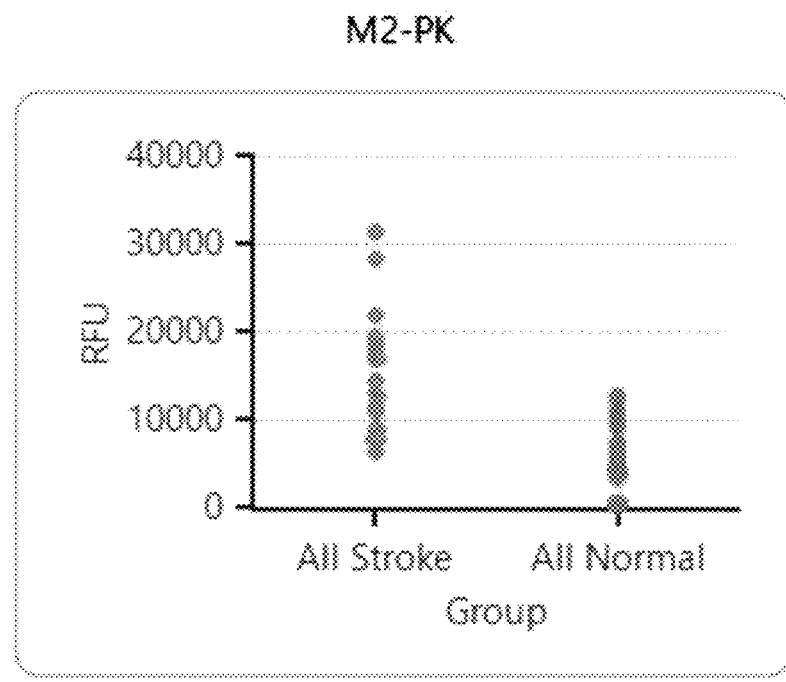
FIG. 12F is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12G:
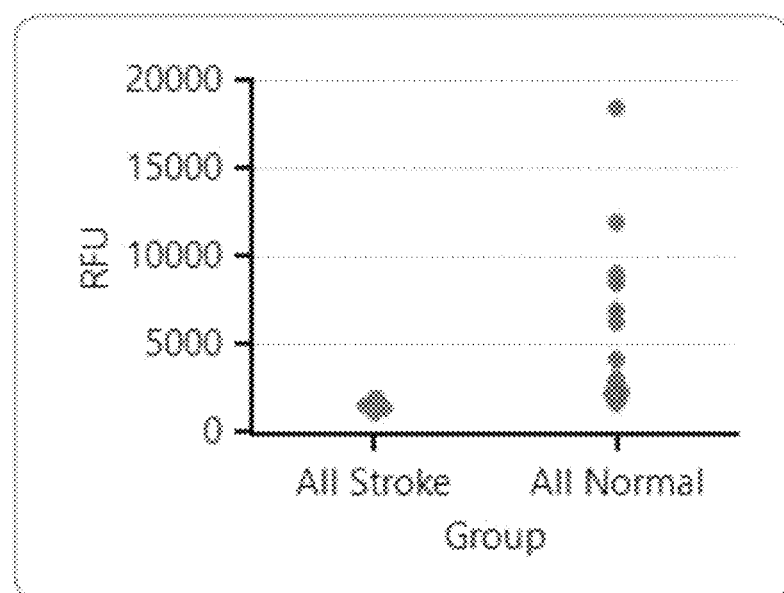
FIG. 12G is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12H:
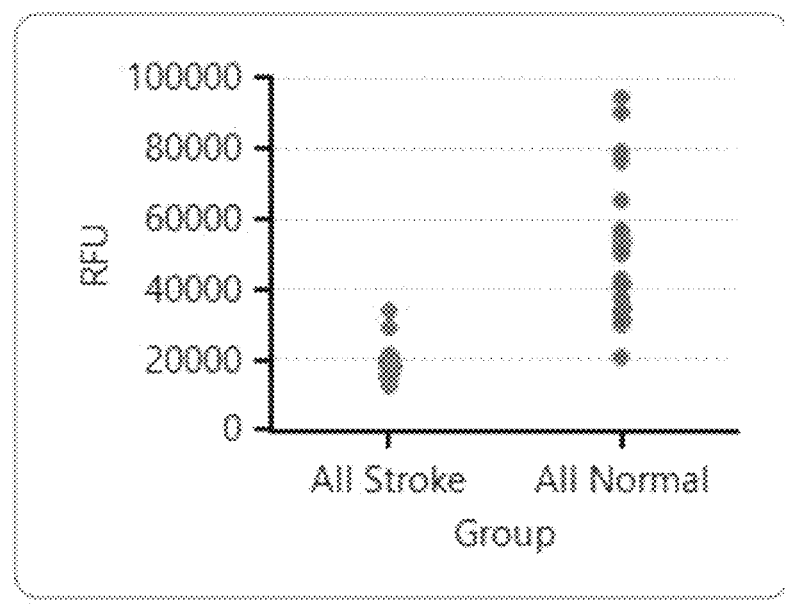
FIG. 12H is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12I:
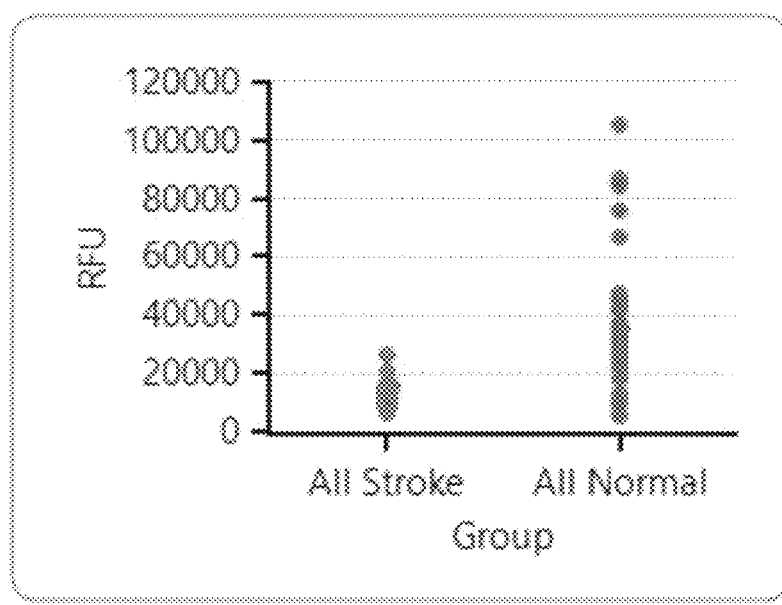
FIG. 12I is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12J:
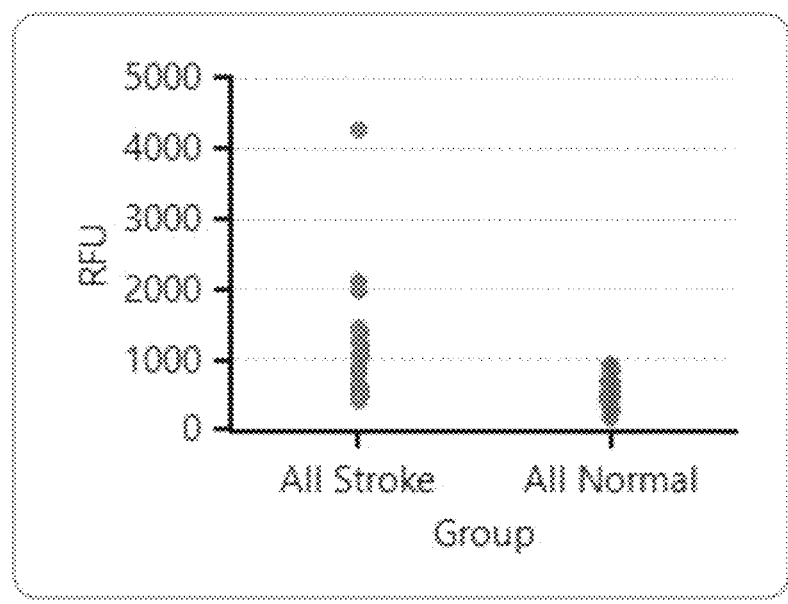
FIG. 12J is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12K:
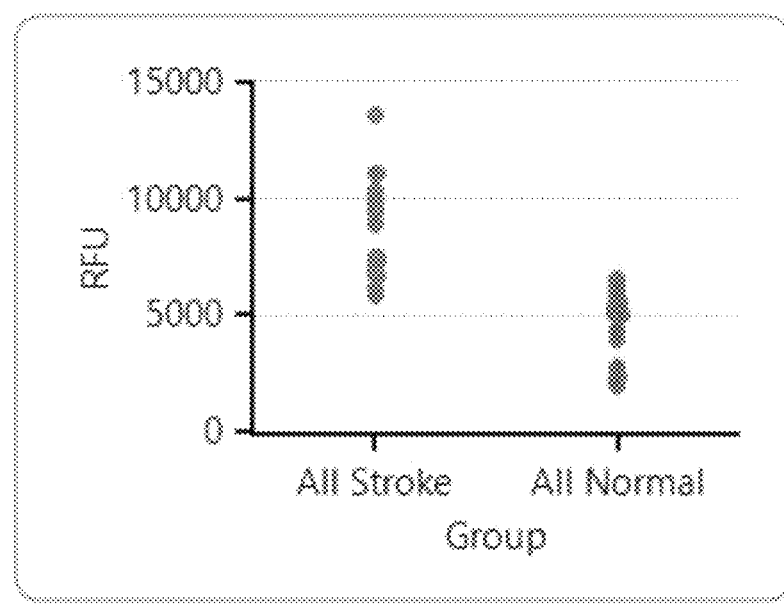
FIG. 12K is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12L:
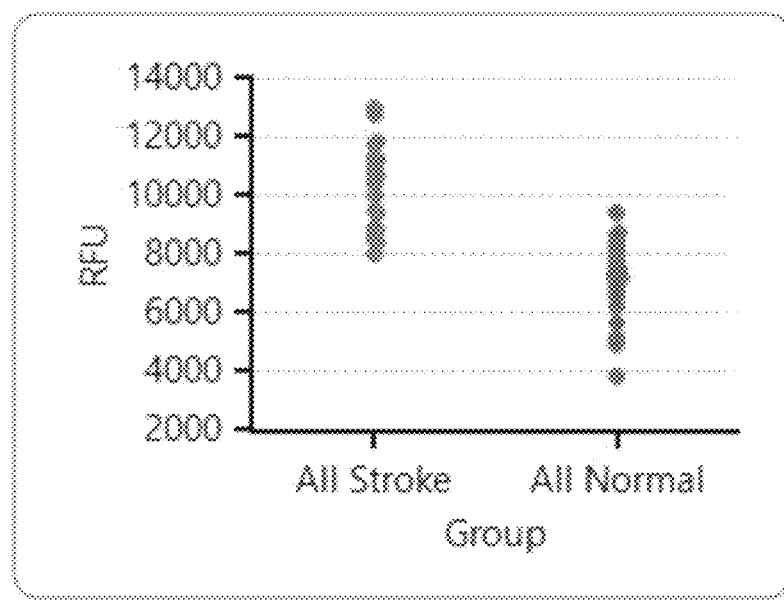
FIG. 12L is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12M:
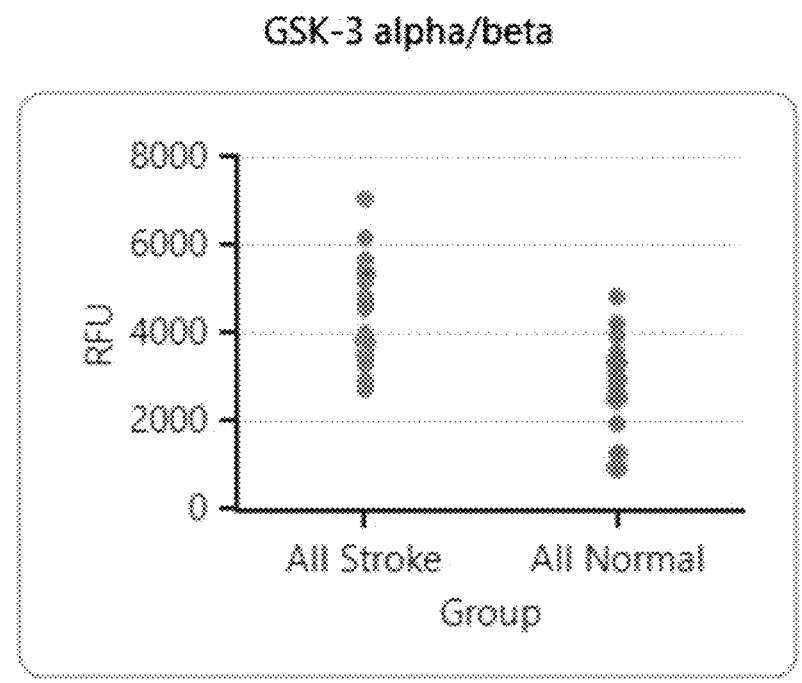
FIG. 12M is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.
Figure 12N:
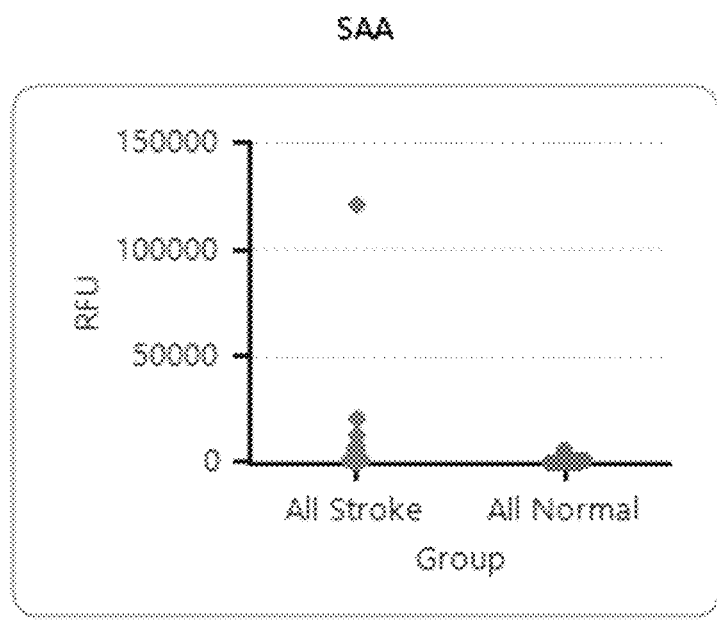
FIG. 12N is a scatter plot depicting candidate biomarker protein abundances in serum from stroke and healthy patients aged 38-90 years. SOMAscan measurements from 22 stroke patients (age range 38-90 years) and 26 healthy patients (age range 48-75 years). RFU=relative fluorescent units.

To validate these initial findings from the limited patient cohorts, these 14 biomarker candidates were then evaluated using SOMAscan measurements for all stroke and healthy patients (aged 38-90). Here, all stroke samples (n=22) were compared to all healthy samples (n=26) (Table 11). While the RFU distributions from the scatter plots are overlapping for many of the proteins, a few still show good separation, including C3b, GDF2, and UB2G2 (FIGS. 12A-12N).

TABLE 9

Patient characteristics for the Age-60 and Age-50 cohorts

| Age-60 Cohort | | | | | Age-50 Cohort | | | | |
| --- | --- | --- | --- | --- | --- | --- | --- | --- | --- |
| Stroke Patient# | Age | Sex | Race | NIHSS | Stroke Patient# | Age | Sex | Race | NIHSS |
| 15 | 64 | F | W | 1 | 8 | 53 | M | W | 3 |
| 18 | 64 | F | W | 15 | 24 | 58 | M | B | 7 |
| 23 | 66 | F | W | 16 | 30 | 50 | M | B | 12 |
| 34 | 63 | M | W | n/a | 45 | 59 | M | W | 27 |
| 50 | 61 | M | W | 2 | 54 | 54 | M | B | 5 |
| Healthy Patient# | Age | Sex | Race | | Healthy Patient# | Age | Sex | Race | |
| 5 | 61 | M | W | n/a | 17 | 54 | M | W | n/a |
| 7 | 62 | M | W | n/a | 18 | 58 | M | W | n/a |
| 8 | 67 | M | W | n/a | 23 | 55 | M | W | n/a |
| 9 | 68 | F | W | n/a | 25 | 51 | M | B | n/a |
| 14 | 60 | F | W | n/a | 26 | 58 | M | B | n/a |

TABLE 11

Patient characteristics for peripheral blood studies.

|  | Stroke n = 22 | Mimic n = 23 | TIA n = 9 | Healthy n = 26 |
|---|---|---|---|---|
| Age (mean ± SD) | 65.4 (±15.3) | 55.8 (±15.5) | 64.4 (±15.4) | 60.9 (±8.7) |
| Female (%) | 45.5% | 60.9% | 33.3% | 38.5% |
| Caucasian (%) | 77.3% | 60.9% | 77.8% | 80.8% |

Figure 13A:
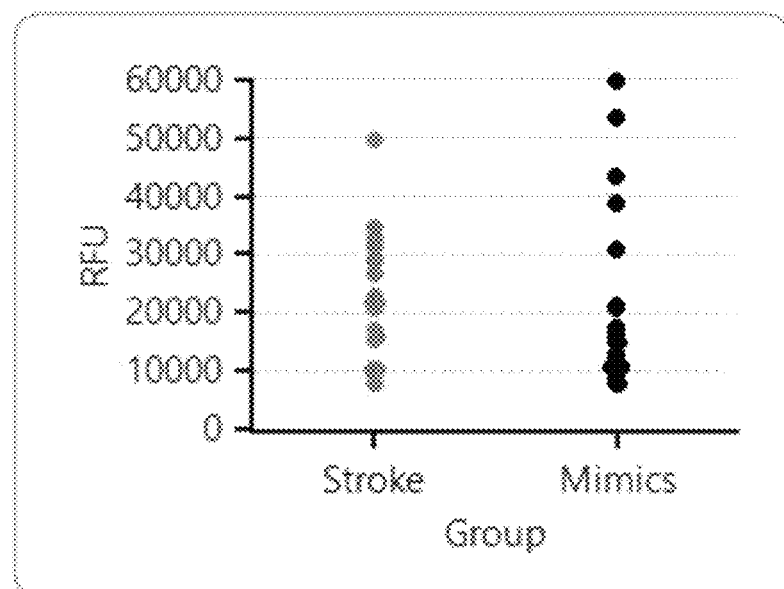
FIG. 13A is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13B:
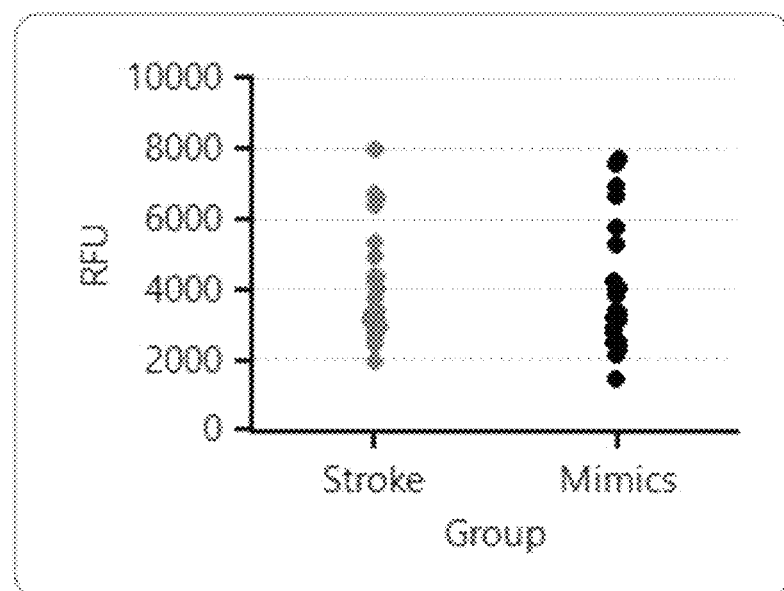
FIG. 13B is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13C:
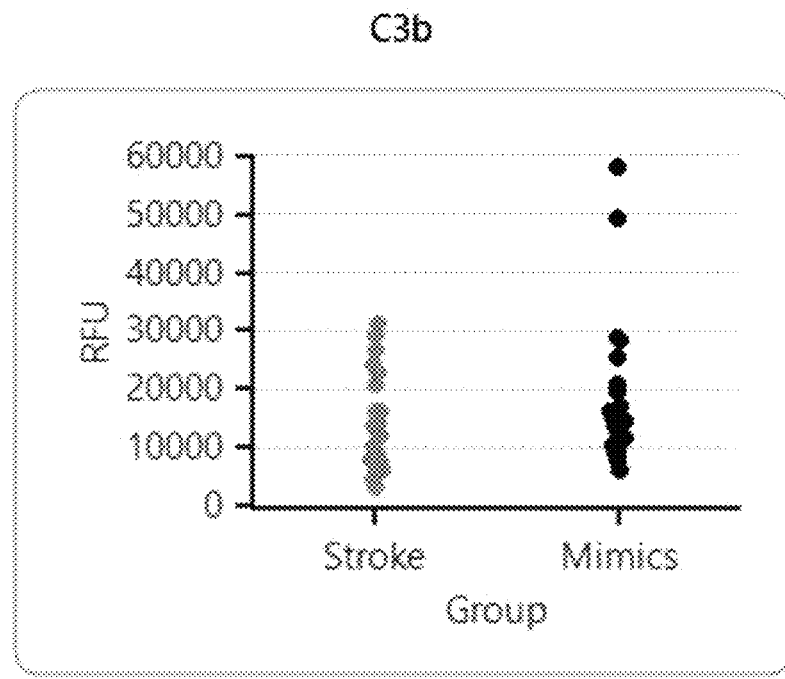
FIG. 13C is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13D:
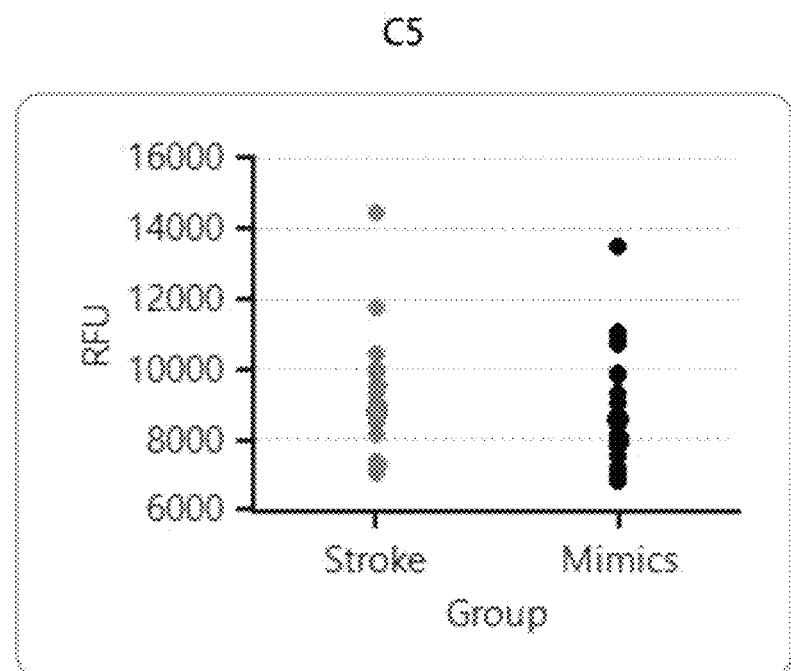
FIG. 13D is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13E:
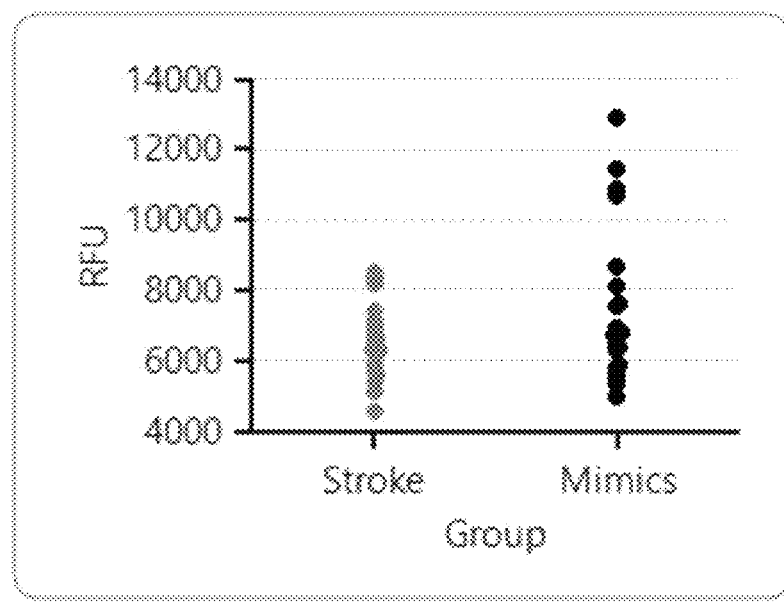
FIG. 13E is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13F:
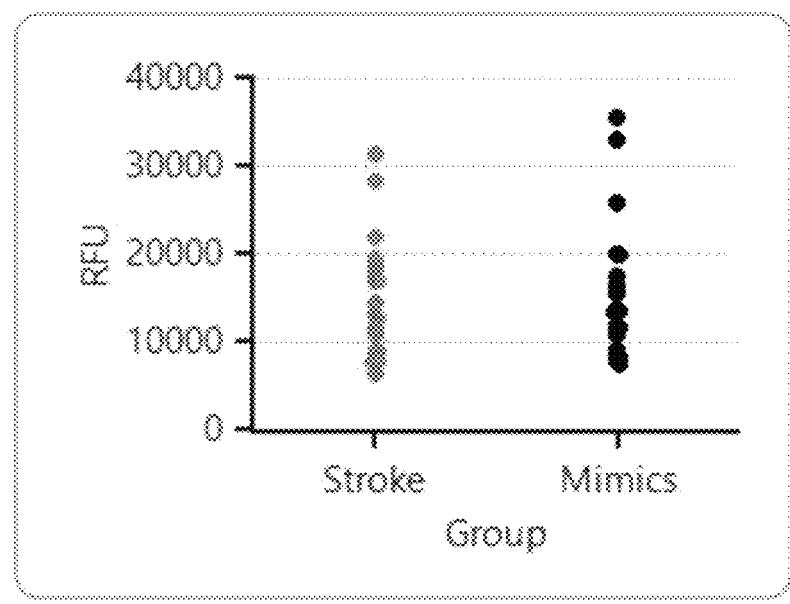
FIG. 13F is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13G:
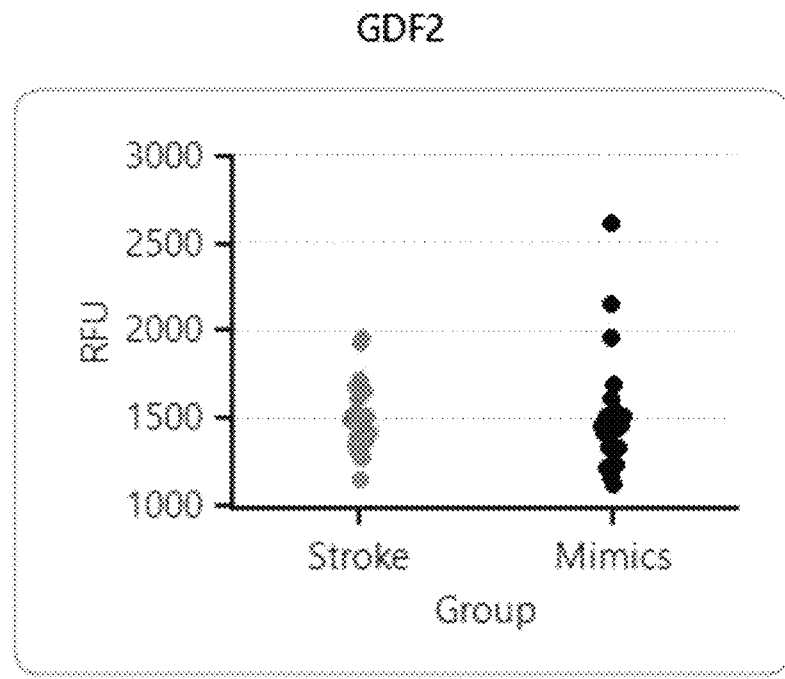
FIG. 13G is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13H:
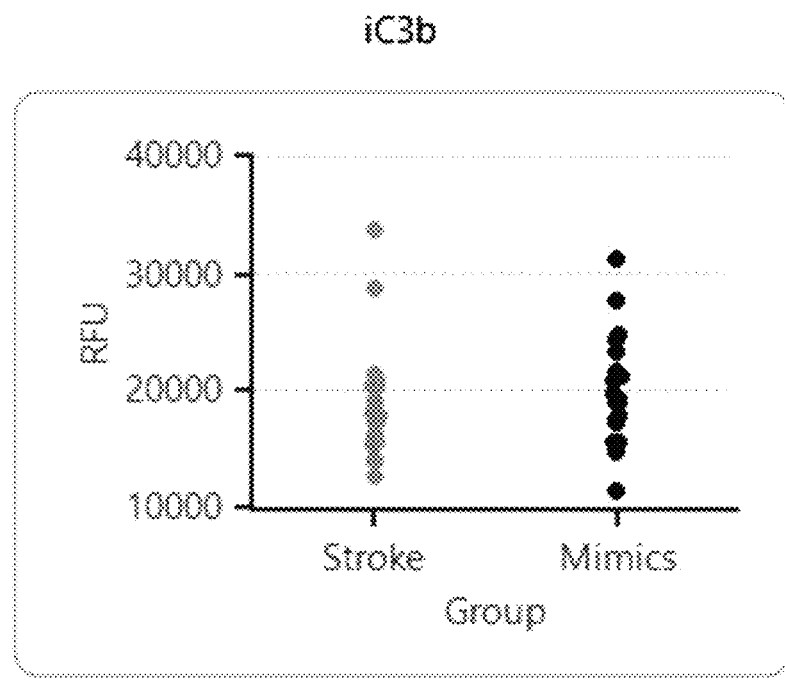
FIG. 13H is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13I:
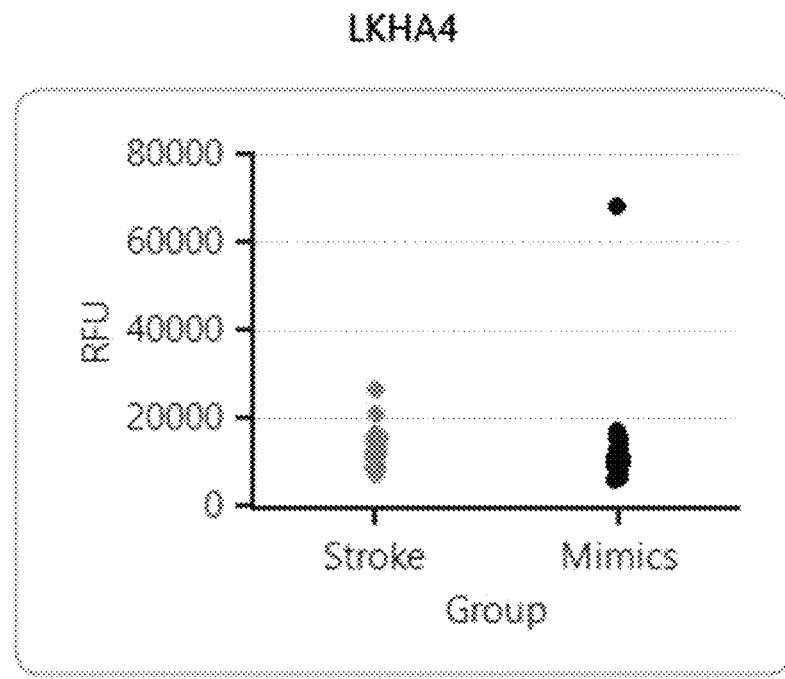
FIG. 13I is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13J:
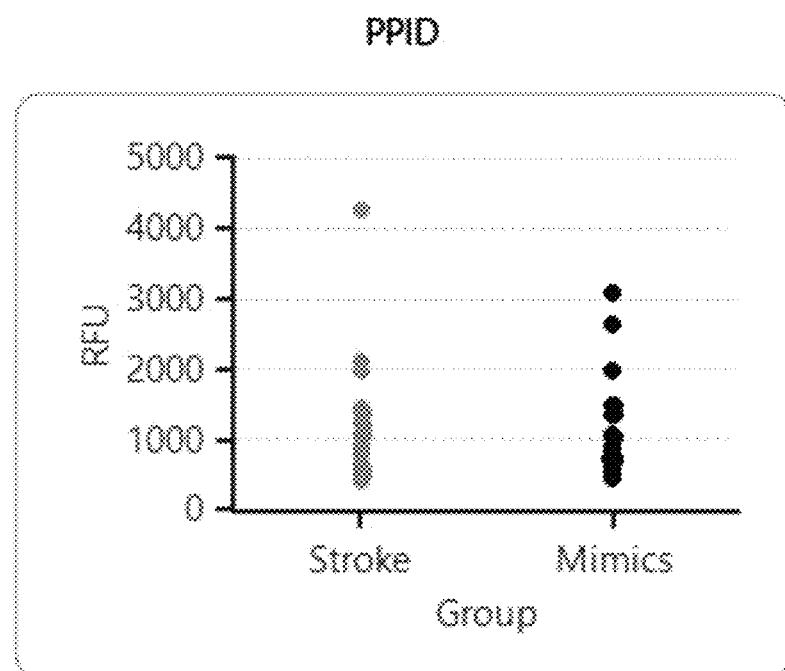
FIG. 13J is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13K:
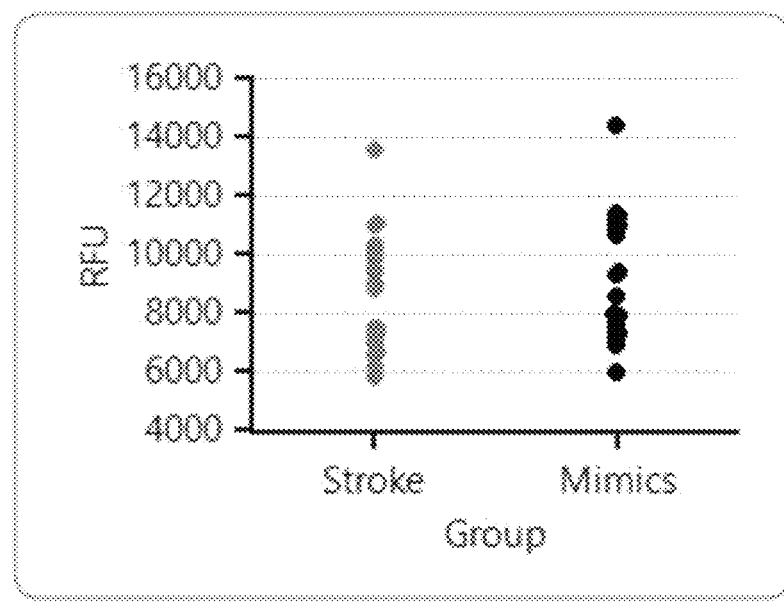
FIG. 13K is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13L:
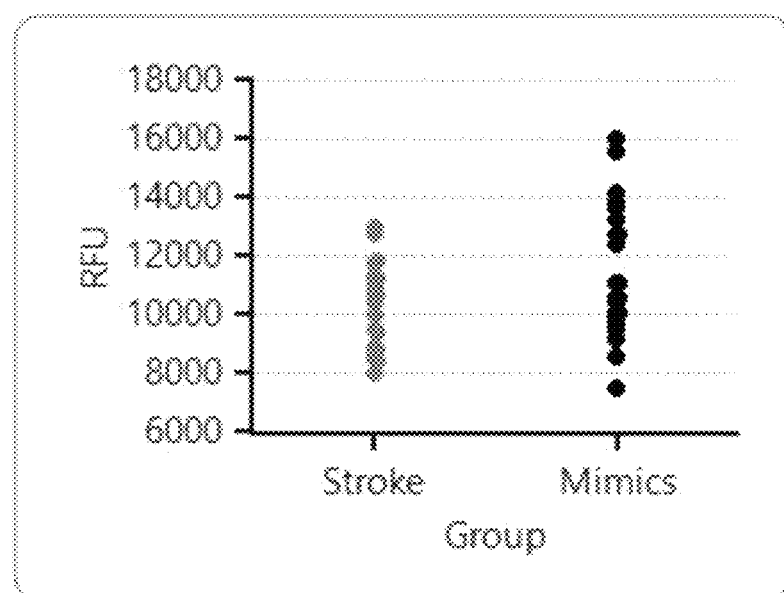
FIG. 13L is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13M:
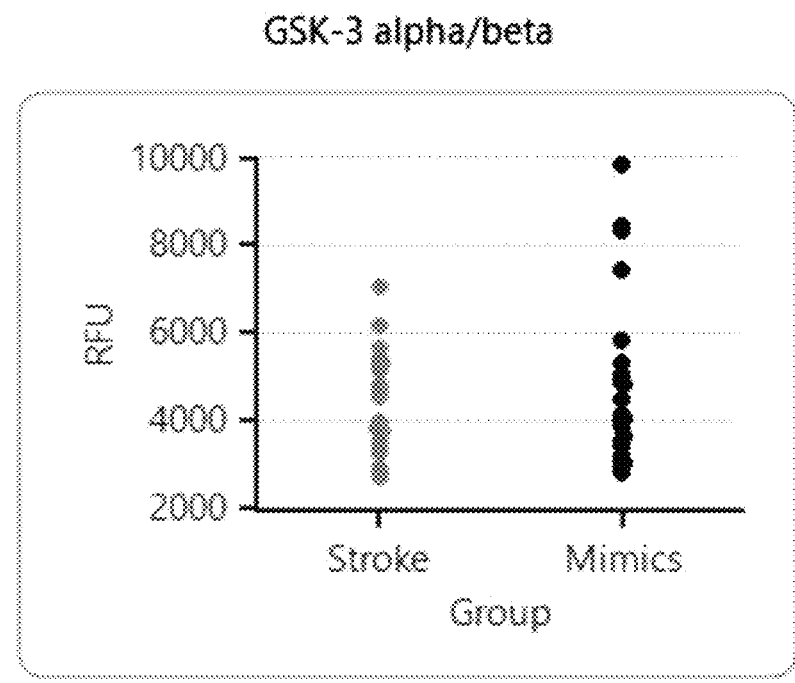
FIG. 13M is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.
Figure 13N:
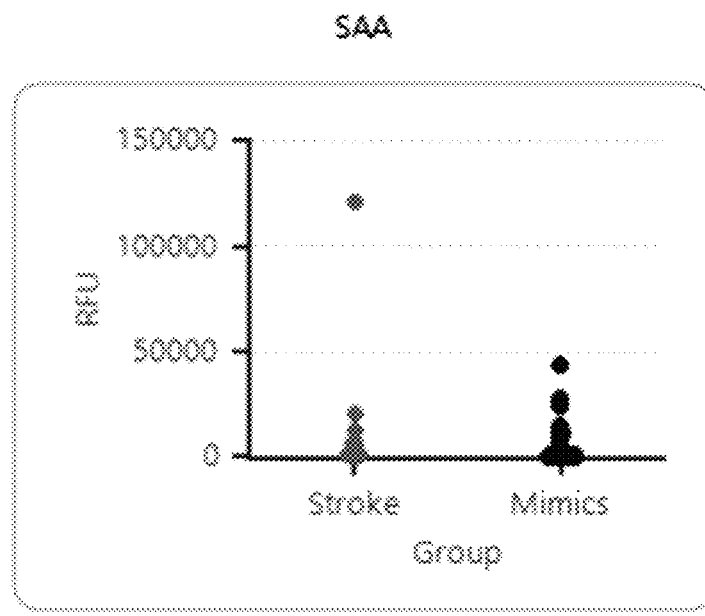
FIG. 13N is a scatter plot depicting candidate biomarker protein abundances in serum from stroke and stroke-mimicking patients aged 26-90 years. SOMAscan measurements from 22 stroke patients (age range 38-90 years) and 32 stroke-mimicking patients (mimic) (age range 26-87 years). RFU=relative fluorescent units.

In an actual clinical setting, physicians and other medical personnel can easily distinguish between a normal healthy person and someone who is unhealthy (i.e., exhibiting symptoms). Because of this, any biomarker candidate must be validated in a more realistic patient cohort. Therefore, all stroke patient samples (n=22) were compared to all stroke-mimicking patient samples (n=32) for the 14 biomarker candidates. Of the mimic group, 9 patients were diagnosed with TIA, 5 with migraine, 3 with seizure, and the remaining were a mix of symptoms with ambiguous etiologies. Scatter plots for the 14 biomarker candidates were used to compare the RFU distribution of all stroke patients to the RFU distribution of all stroke-mimicking patients (FIGS. 13A-13N). There was a large amount of overlap seen in RFU distributions between the two groups.

When comparing pooled serum from stroke patients to that of healthy patients using 2D gel electrophoresis, SAA was found only in the pooled stroke sample, suggesting it was a stroke-induced change. This protein is produced by the liver to transport cholesterol, but also acts as a chemoattractant for immune cells, and binds heparin which is a naturally occurring anticoagulant. SAA isoforms can be constitutively present in the blood or expressed acutely in response to inflammation. A previous study has shown that increased SAA levels differentiate atherothrombotic etiology from cardioembolic etiology in stroke patients. Atherosclerosis is a disease associated with chronic inflammation, suggesting that SAA levels were increased prior to rather than following a stroke event. SAA therefore may be a diagnostic biomarker candidate for ischemic stroke as well as an indicator of an underlying risk factor.

There were a number of differences in the 2D gels of stroke and healthy patients for the aged-60 cohort that were not seen in the aged-50 cohort. As each gel represented five patients, the differences seen between the two age groups might be due to varying patient characteristics (i.e., locations of the strokes). Alternatively, it may suggest age-related differences. Perhaps the protein response to stroke seen in the older cohort is in some way dampened in the younger stroke cohort. The 2D gels from the two healthy age groups also are qualitatively different. Almost all the low molecular weight apolipoproteins are missing from the younger age group (Spot 15, FIGS. 8A and 8B). Age is a known risk factor for stroke, and apolipoproteins—being associated with cholesterol formation—are also predictors of the disease. However, because these are pooled experiments, it cannot be determined if the changes between stroke and healthy seen in the age-60 cohort are from one patient or all patients. Follow up on individual samples may be needed.

Univariate analyses of the entire SOMAscan dataset revealed 195 other protein biomarker candidates. The overlap in serum protein concentrations for these two groups was minimal. However, when the same proteins were compared using stroke and stroke-mimicking patients, there was no longer a distinct threshold value for distinguishing a high sensitivity and specificity. The individual proteins did not appear to be clinically relevant biomarkers as they could not differentiate stroke patients from stroke-mimicking patients with high sensitivity or specificity. In some embodiments, finding a combination of these proteins that differentiates the two groups may also be employed.

Thirteen serum proteins were identified in ischemic stroke patients that may differentiate stroke from healthy patients. Unfortunately, these serum protein biomarker candidates do not appear to be clinically relevant when comparing stroke patients to stroke-mimicking patients.

Example III

As discussed above, proteins in peripheral blood from ischemic stroke patients and healthy individuals were compared. Several proteins were identified that differentiated these patient groups, but when the concentrations of these proteins were compared between stroke and stroke-mimicking patients, the individual proteins did not appear to have a clinically relevant sensitivity and specificity. A study was designed to compare stroke patients to stroke-mimicking patients as opposed to healthy individuals to develop a panel of stroke biomarker proteins to gain sufficient sensitivity and specificity for clinical application.

In this aim, the venous blood of stroke patients was compared to that of stroke-mimicking patients to find clinically relevant protein biomarker candidates. The main goal was to determine what proteins may be differentially expressed in the blood of stroke patients when compared to stroke-mimicking patients, and to find a combination of proteins that predicts ischemic stroke diagnosis.

Serum proteins found in ischemic stroke patients were evaluated in an attempt to identify proteins that can be used to differentiate stroke from stroke-mimicking patients using three approaches.

First, the SOMAscan assay data was used to evaluate previously identified stroke biomarkers from published literature. Second, to identify novel biomarker candidates, univariate analyses were used to identify individual proteins that were significantly different between stroke and stroke-mimicking groups. Third, a machine learning algorithm was employed to identify protein combinations that accurately classify stroke patients from other non-stroke groups. See above for details on methods.

Twenty-five biomarkers were identified from literature reviews (Table 12). Of these, 20 proteins were available for analysis on the SOMAscan assay. Several of these proteins were previously evaluated as components of biomarker panels (Table 1), and the remaining were chosen based on their specific expression to the brain (GFAP, NSE, 14-3-3 protein zeta/delta, dynactin 1, myokinase, cadherin-5, cdk5).

TABLE 12

Protein biomarker candidates previously published.

| Protein | Description | UniProt ID | Ref | Present on SOMAscan Assay |
|---|---|---|---|---|
| *Inflammatory/Apoptotic Mediators* | | | | |
| Vascular Cell Adhesion Molecule (VCAM) | Immunoglobulin, mediates adhesion of immune cells to endothelium | P19320 | Lynch, 2004 | Yes |
| Eotaxin (CCL11) | Chemotaxis of eosinophils | P51671 | Sharma, 2014 | Yes |
| Caspase 3 (CASP3) | Protease, involved in apoptosis | P42574 | Montaner, 2011 | Yes |
| sRAGE | Receptor for glycosylated proteins; Involved in vascular inflammation | Q15109 | Montaner, 2011 | Yes |
| Monocyte Chemoattractant Protein (MCP-1, CCL2) | Chemoattracts monocytes and basophils, implicated in atherosclerosis | P13500 | Reynolds 2003 | Yes |
| S100A12 | Calcium-binding protein, proinflammatory | P80511 | Sharma, 2014 | Yes |
| *Other* | | | | |
| Matrix Metalloproteinase 9 (MMP9) | Proteolytic enzyme of the extracellular matrix | P14780 | Montaner, 2011, Reynolds 2003, Laskowitz, 2009, Lynch, 2004, Vanni, 2011 | Yes |
| Brain natriuretic peptide (BNP) | Cardiac hormone, released following cardiac stress | P16860 | Laskowitz, 2009, Vanni, 2011 | Yes |
| Secretogogin (SCGN) | Calcium-binding protein, expressed in neuroendocrine cells | O76038 | Montaner, 2011 | No |
| Beta Nerve Growth Factor (bNGF) | Nerve Growth factor, metalloprotease inhibitor | P01138 | Reynolds 2003 | Yes |
| Epidermal Growth Factor Receptor (ERBB1) | Growth factor receptor, implicated in reactive gliosis | P00533 | Sharma, 2014 | Yes |
| Metalloproteinase inhibitor-4 | Irreversible inactivation of MMPs | Q99727 | Sharma, 2014 | No |
| Prolactin | Hormone with role in platelet activation | P01236 | Sharma, 2014 | Yes |
| *Central Nervous System Tissue Markers* | | | | |
| S100B | Calcium binding protein, expressed in astroglial cells | P04271 | Reynolds 2003, Laskowitz, 2009, Lynch, 2004, Vanni. 2011 | No |
| Glial Fibrillary Acidic Protein (GFAP) | Intermediate Filament Protein, expressed in astroglial cells | P14136 | Pieper, 2003, Glushakova, 2016, Purrucker, 2014 | Yes |
| Neuron-Specific Enolase (NSE) | Neuronal glycolytic enzyme found mainly in neurons | P09104 | Glushakova, 2016 | Yes |
| Visinin-like Protein-1 (VLP1) | Neuronal intracellular calcium sensor | P62760 | Glushakova, 2016, Laterza, 2006, Stejskal, 2011 | No |
| 14-3-3 zeta/delta | Expressed in nerve terminals of neurons | P63104 | Pieper, 2003 | Yes |
| Dynactin 1 | Vesicle transport protein, expressed specifically in brain tissue | Q14203 | Pieper, 2003 | Subunit 2 |
| Adenylate kinase isoenzyme 5 (AK5) | Enzyme involved in cell energy homeostasis, expressed in brain tissue | Q9Y6K8 | Pieper, 2003, VanRompay, 1999 | Isoenzyme 1 ((Myokinase)) |
| Vascular endothelial cadherin (Cadherin-5) | Cell-adhesion glycoprotein, expressed in brain and endothelial tissue | P33151 | Pieper, 2003 | Yes |
| Cdk5/p35 | Protein kinase involved in neuronal cell cycle arrest and neuronal apoptosis | Q00535 Q15078 | Meyer, 2014 | Yes |
| Chimerin | Signal-transducing protein, expressed in neurons of the brain | P15882 | Montaner, 2011 | No |
| *Coagulation/Thrombosis Markers* | | | | |
| vonWillebrand Factor (vWF) | Glycoprotein involved in coagulation | P04275 | Reynolds 2003, Lynch, 2004 | Yes |
| D-dimer | Breakdown product of fibrin blood clot | P02671 P02675 P02679 | Montaner, 2011, Laskowitz, 2009, Vanni, 2011 | Yes |

Proteins were selected based on brain-tissue specificity or previous evaluation as a stroke biomarker. Of the 25 proteins, 20 were available to measure with the SOMAscan assay. Note: AK5 is not available on the assay, but an isoform (myokinase) was available and therefore used for testing.

Figure 14A:
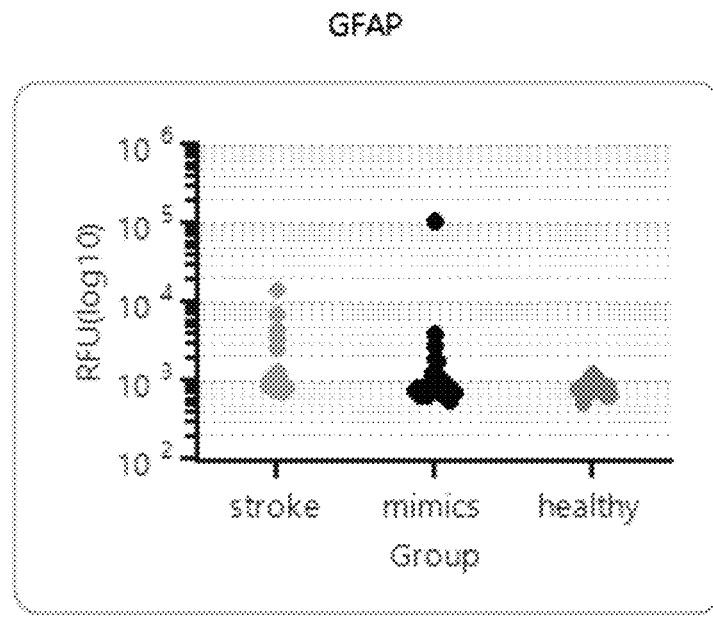
FIG. 14A is a scatter plot depicting comparisons of GFAP, b-NGF, and vWF protein concentrations. Three proteins from Table 14 had a statistical difference between 22 stroke patients and 32 stroke-mimicking (mimic) patients when compared using the Mann Whitney U test. Healthy patients were not included in this analysis, however, protein concentrations for this group are shown as a comparison to the other two groups. RFU=relative fluorescent units.
Figure 14B:
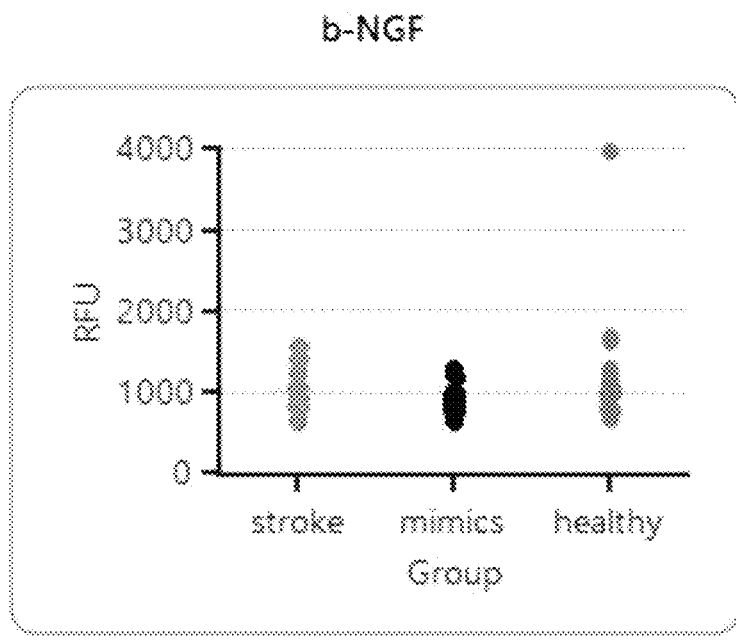
FIG. 14B is a scatter plot depicting comparisons of GFAP, b-NGF, and vWF protein concentrations. Three proteins from Table 14 had a statistical difference between 22 stroke patients and 32 stroke-mimicking (mimic) patients when compared using the Mann Whitney U test. Healthy patients were not included in this analysis, however, protein concentrations for this group are shown as a comparison to the other two groups. RFU=relative fluorescent units.
Figure 14C:
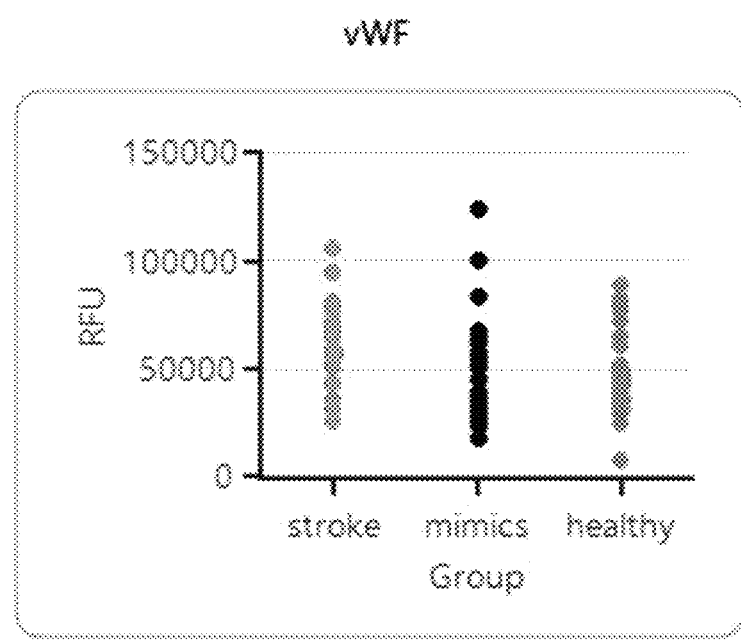
FIG. 14C is a scatter plot depicting comparisons of GFAP, b-NGF, and vWF protein concentrations. Three proteins from Table 14 had a statistical difference between 22 stroke patients and 32 stroke-mimicking (mimic) patients when compared using the Mann Whitney U test. Healthy patients were not included in this analysis, however, protein concentrations for this group are shown as a comparison to the other two groups. RFU=relative fluorescent units.
Figure 15A:
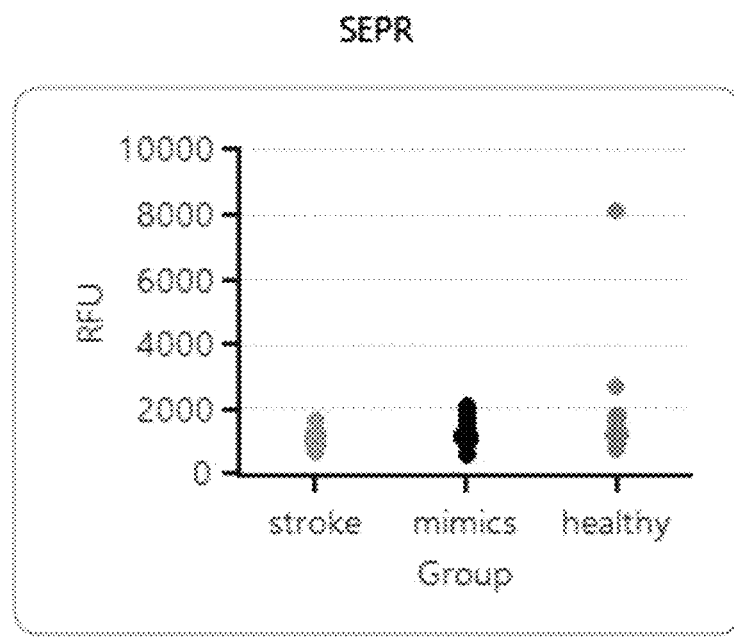
FIG. 15A is a scatter plot depicting comparisons of protein concentrations for proteins significantly different between stroke and stoke mimicking patients. Following Mann Whitney U test on 22 stroke patients and 32 stroke-mimicking patients (mimics), six proteins were found to have a p-value<0.02. Shown in order of decreasing statistical significance. Concentrations from healthy patient samples are shown only for comparison to the other two groups. RFU=relative fluorescent units.
Figure 15B:
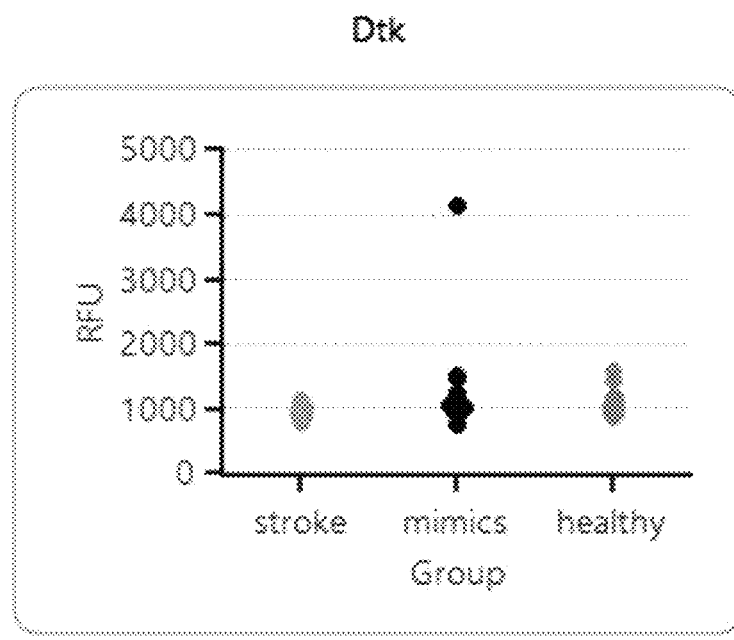
FIG. 15B is a scatter plot depicting comparisons of protein concentrations for proteins significantly different between stroke and stoke mimicking patients. Following Mann Whitney U test on 22 stroke patients and 32 stroke-mimicking patients (mimics), six proteins were found to have a p-value<0.02. Shown in order of decreasing statistical significance. Concentrations from healthy patient samples are shown only for comparison to the other two groups. RFU=relative fluorescent units.
Figure 15C:
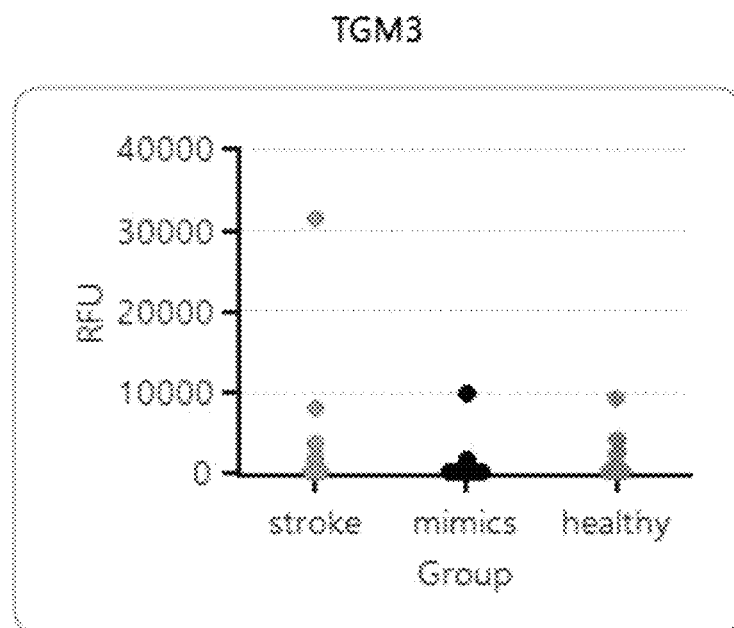
FIG. 15C is a scatter plot depicting comparisons of protein concentrations for proteins significantly different between stroke and stoke mimicking patients. Following Mann Whitney U test on 22 stroke patients and 32 stroke-mimicking patients (mimics), six proteins were found to have a p-value<0.02. Shown in order of decreasing statistical significance. Concentrations from healthy patient samples are shown only for comparison to the other two groups. RFU=relative fluorescent units.
Figure 15D:
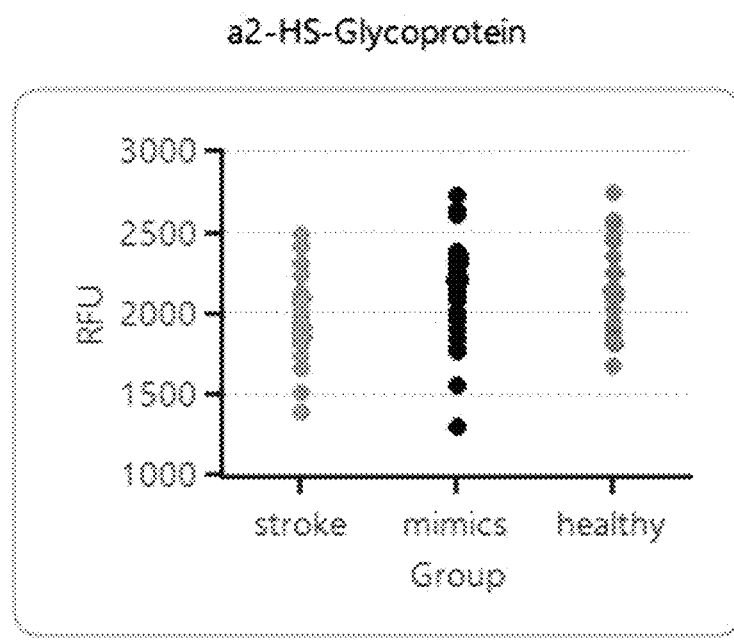
FIG. 15D is a scatter plot depicting comparisons of protein concentrations for proteins significantly different between stroke and stoke mimicking patients. Following Mann Whitney U test on 22 stroke patients and 32 stroke-mimicking patients (mimics), six proteins were found to have a p-value<0.02. Shown in order of decreasing statistical significance. Concentrations from healthy patient samples are shown only for comparison to the other two groups. RFU=relative fluorescent units.
Figure 15E:
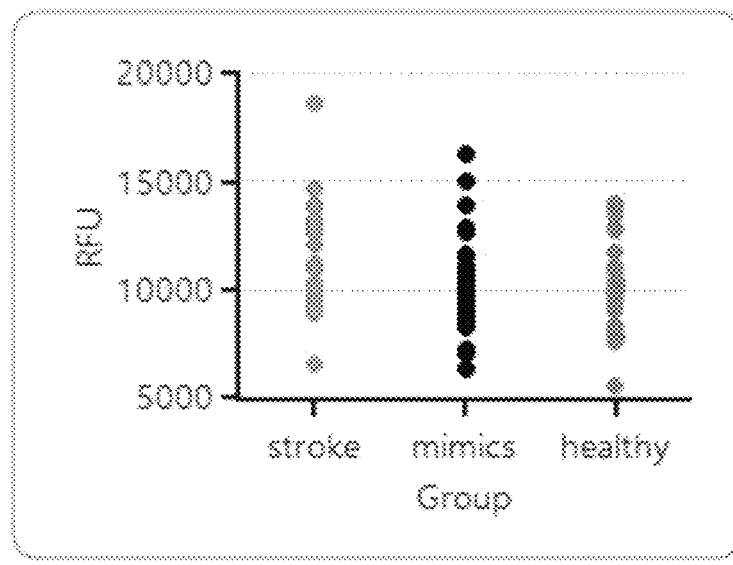
FIG. 15E is a scatter plot depicting comparisons of protein concentrations for proteins significantly different between stroke and stoke mimicking patients. Following Mann Whitney U test on 22 stroke patients and 32 stroke-mimicking patients (mimics), six proteins were found to have a p-value<0.02. Shown in order of decreasing statistical significance. Concentrations from healthy patient samples are shown only for comparison to the other two groups. RFU=relative fluorescent units.
Figure 15F:
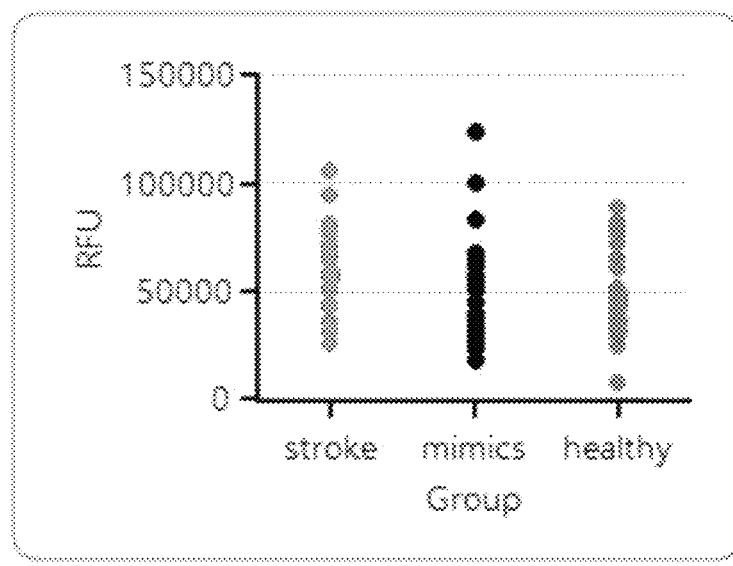
FIG. 15F is a scatter plot depicting comparisons of protein concentrations for proteins significantly different between stroke and stoke mimicking patients. Following Mann Whitney U test on 22 stroke patients and 32 stroke-mimicking patients (mimics), six proteins were found to have a p-value<0.02. Shown in order of decreasing statistical significance. Concentrations from healthy patient samples are shown only for comparison to the other two groups. RFU=relative fluorescent units.
Figure 16A:
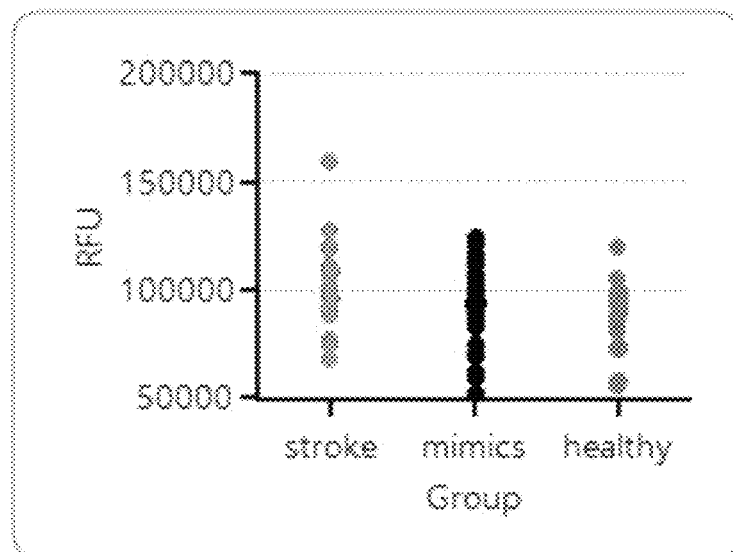
FIG. 16A is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 16B:
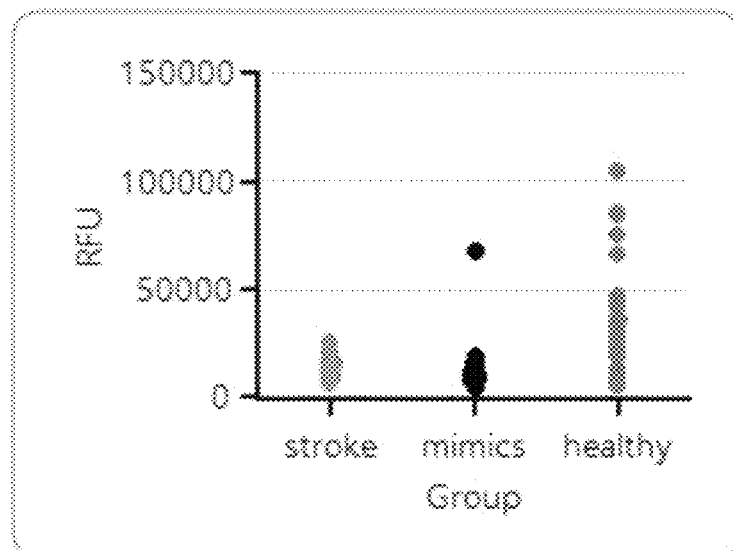
FIG. 16B is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 16C:
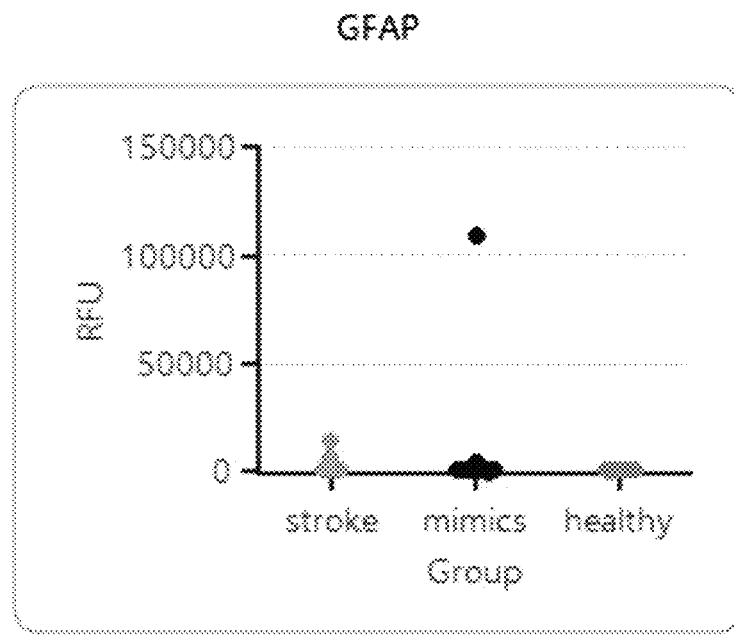
FIG. 16C is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 16D:
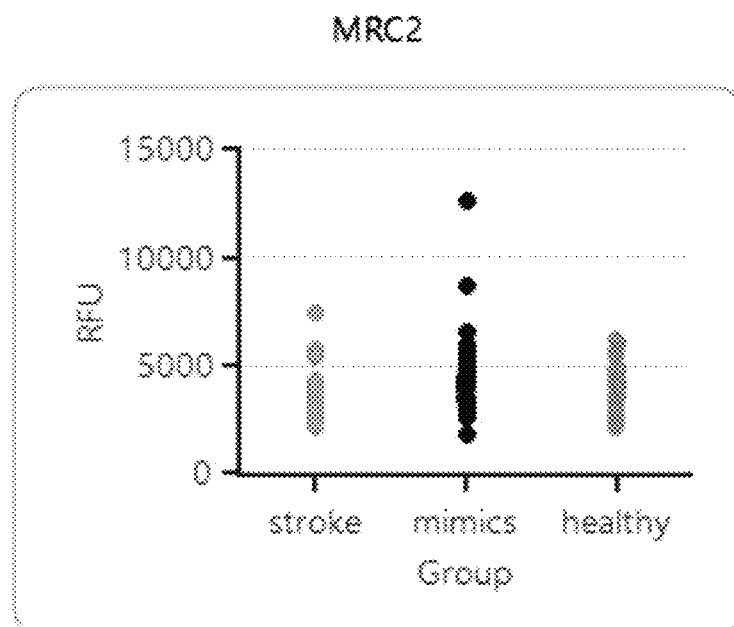
FIG. 16D is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 16E:
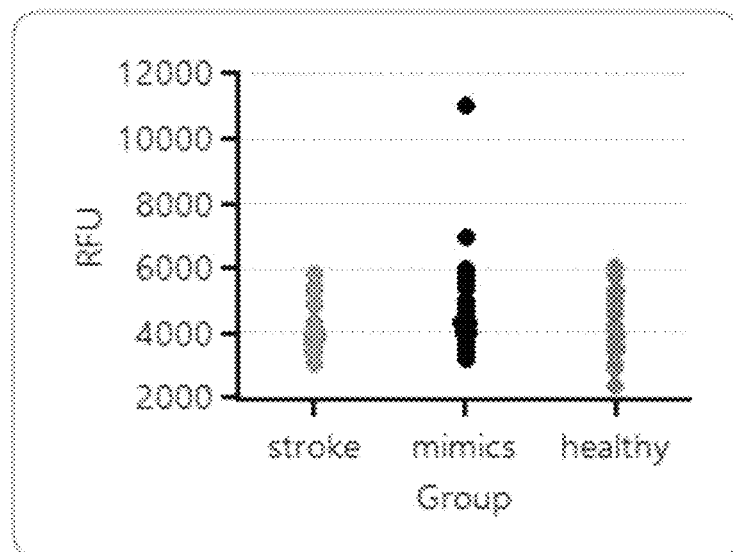
FIG. 16E is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 16F:
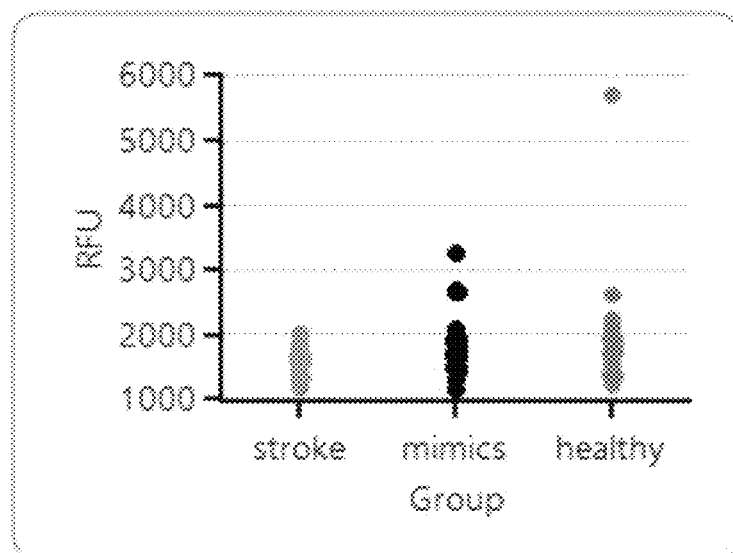
FIG. 16F is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 16G:
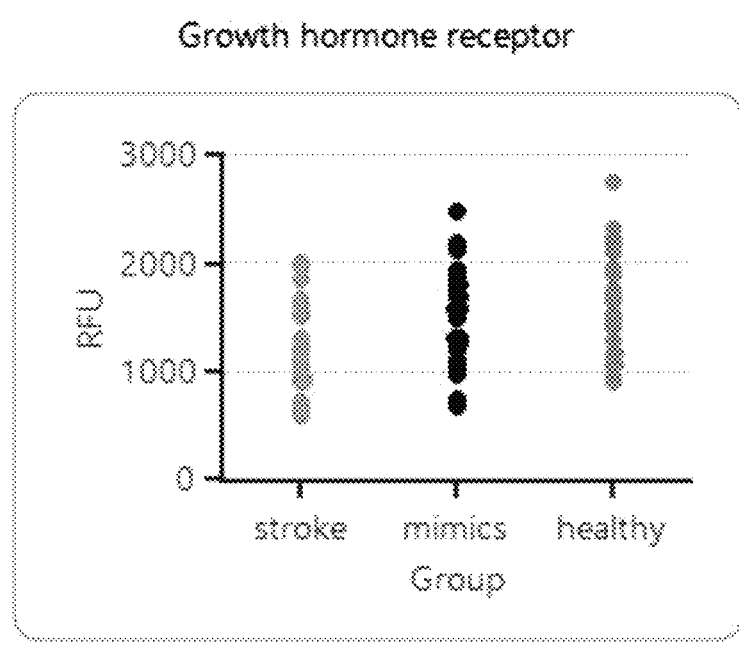
FIG. 16G is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.02<p\leq0.03$. Shown in order of decreasing statistical significance. Concentrations from healthy patient samples are shown only for comparison to the other two groups. RFU=relative fluorescent units.
Figure 17A:
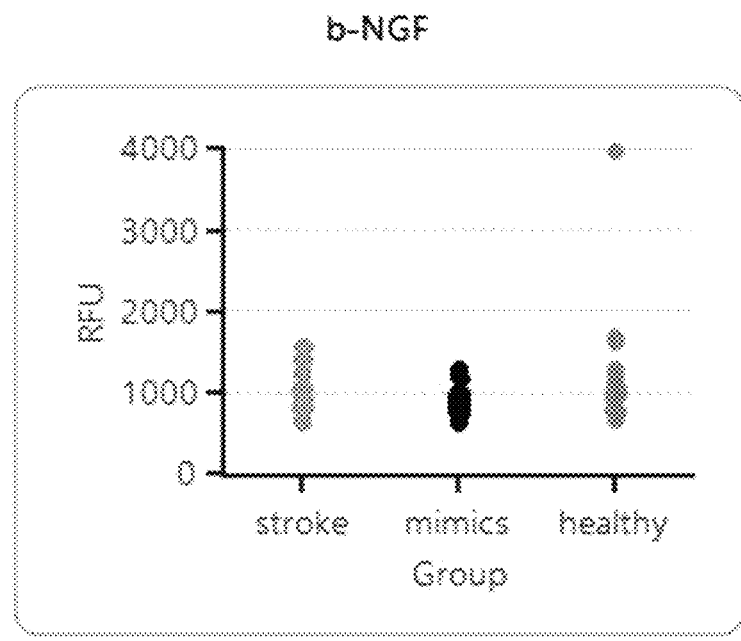
FIG. 17A is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 17B:
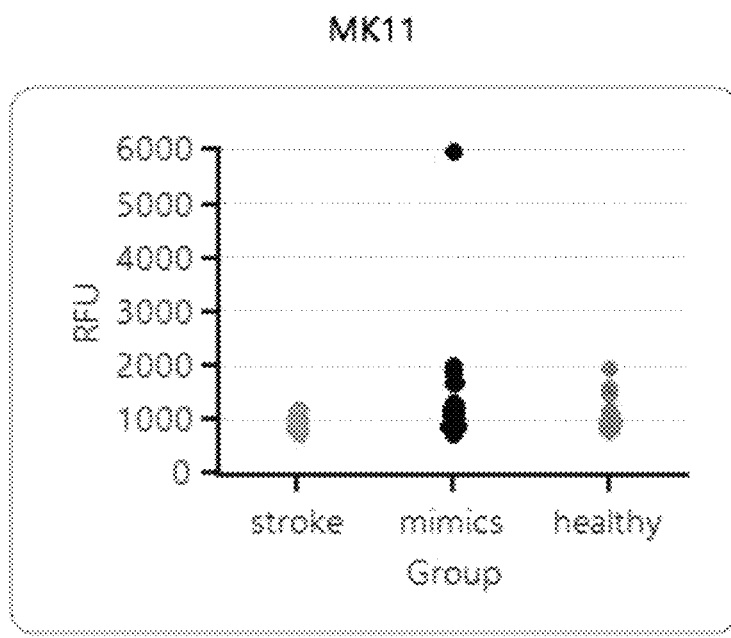
FIG. 17B is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 17C:
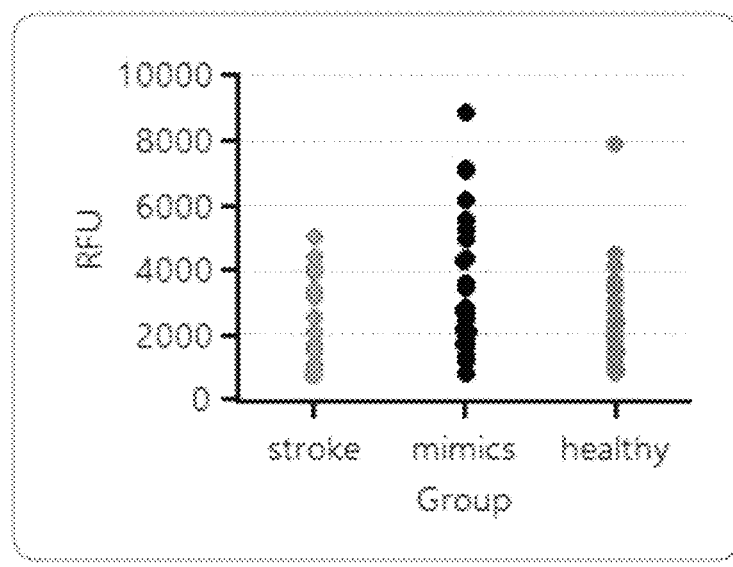
FIG. 17C is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 17D:
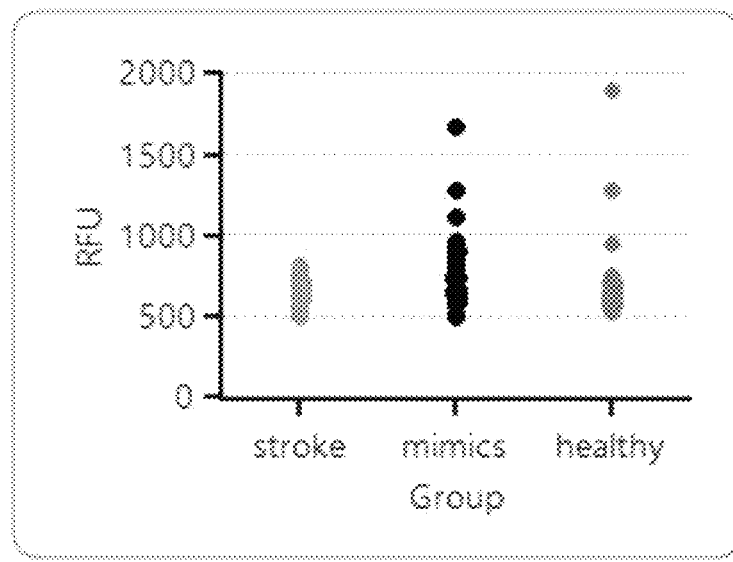
FIG. 17D is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 17E:
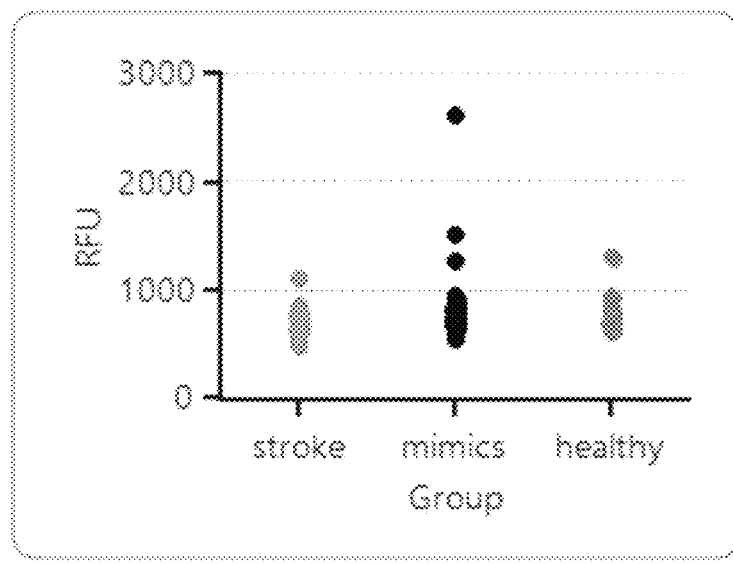
FIG. 17E is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 17F:
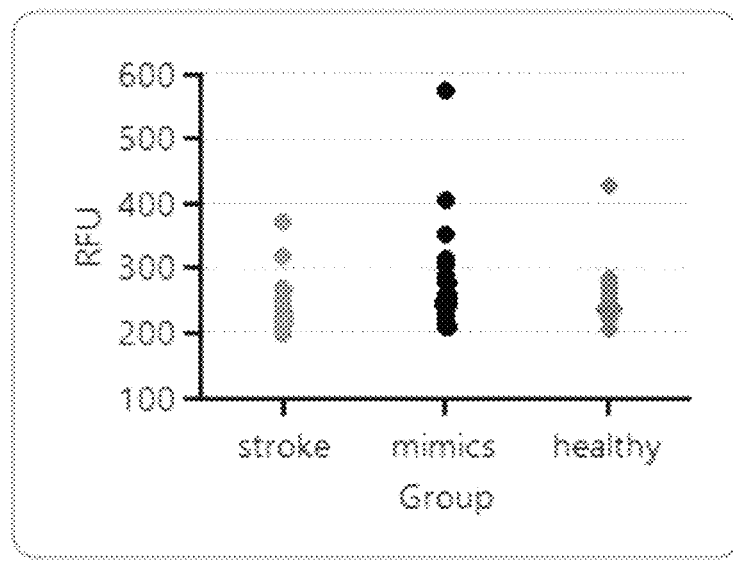
FIG. 17F is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 17G:
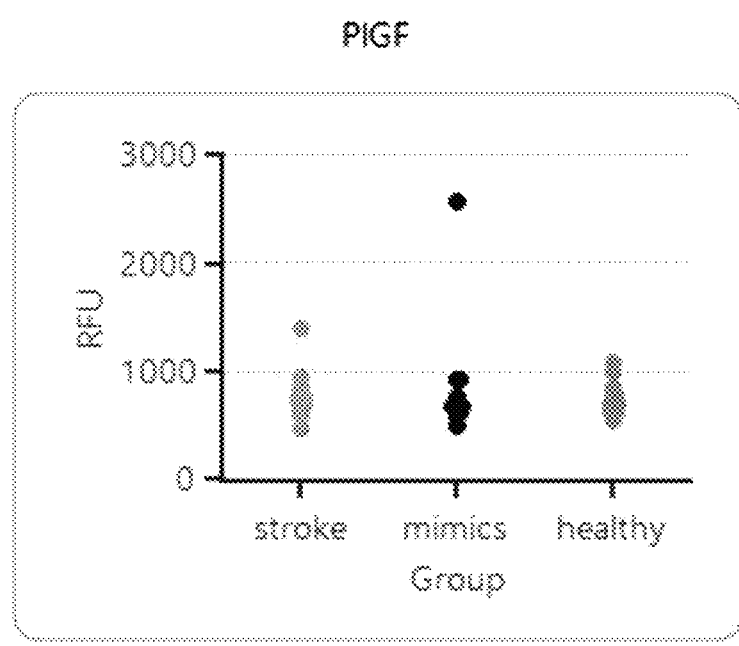
FIG. 17G is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.03<p\leq0.04$. Shown in order of decreasing statistical significance. Concentrations from healthy patient samples are shown only for comparison to the other two groups. RFU=relative fluorescent units.
Figure 18A:
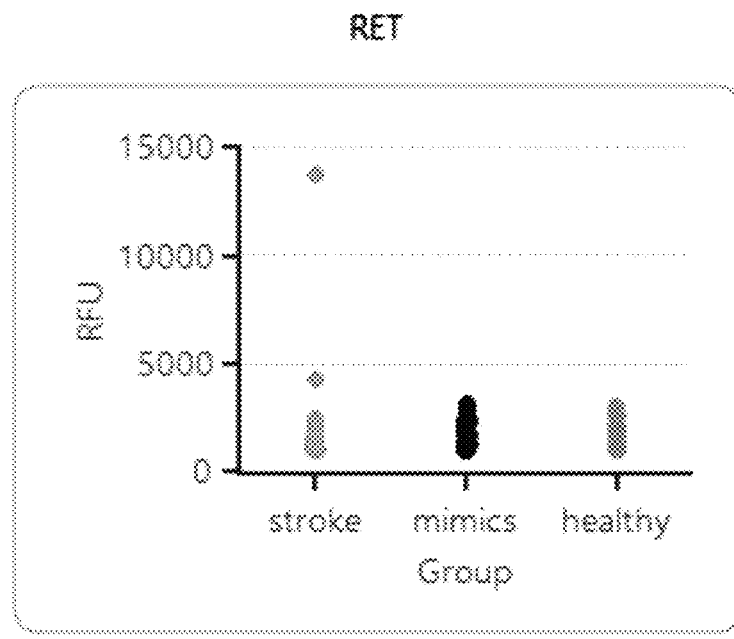
FIG. 18A is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.
Figure 18B:
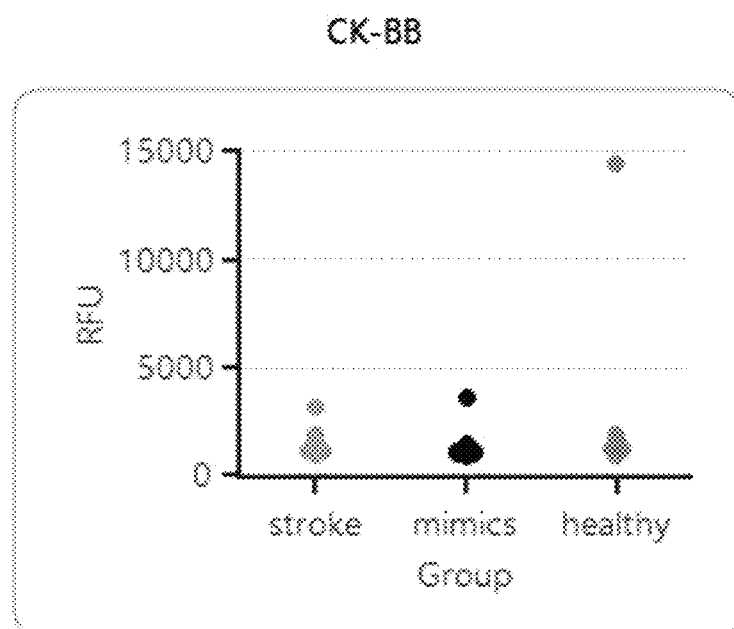
FIG. 18B is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.
Figure 18C:
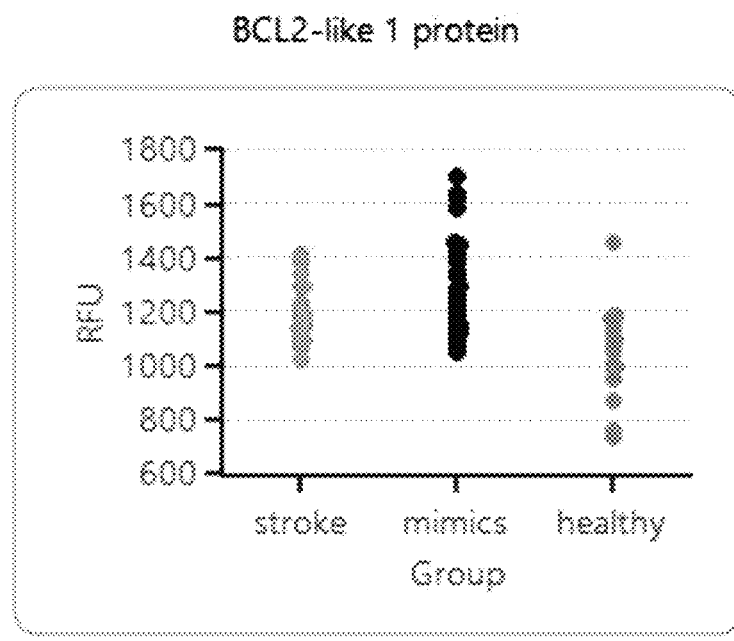
FIG. 18C is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.
Figure 18D:
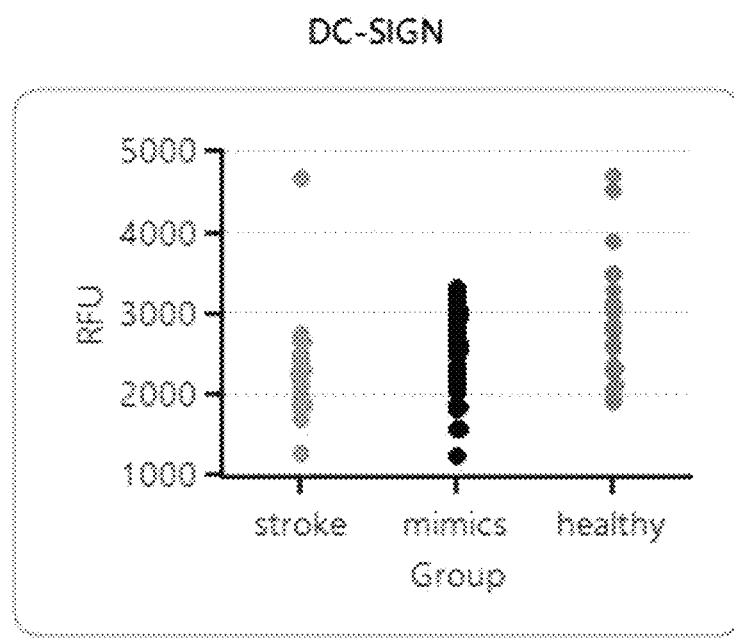
FIG. 18D is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.
Figure 18E:
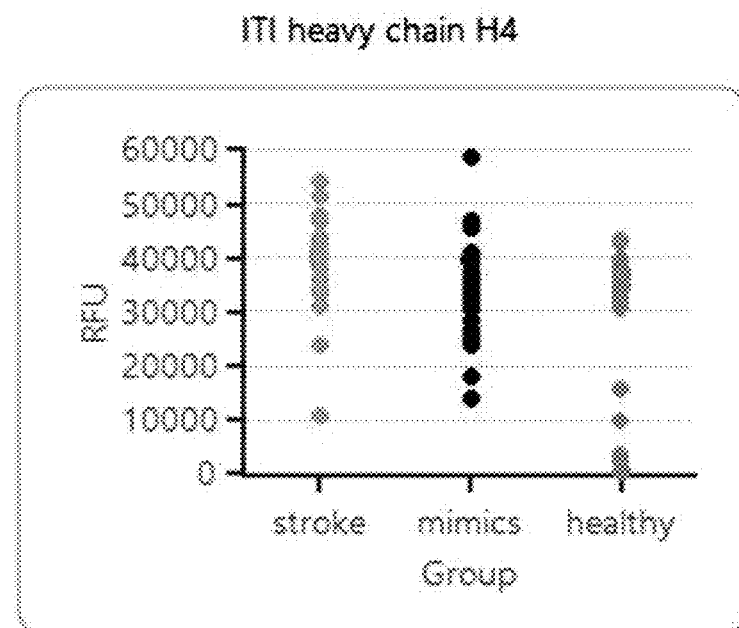
FIG. 18E is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.
Figure 18F:
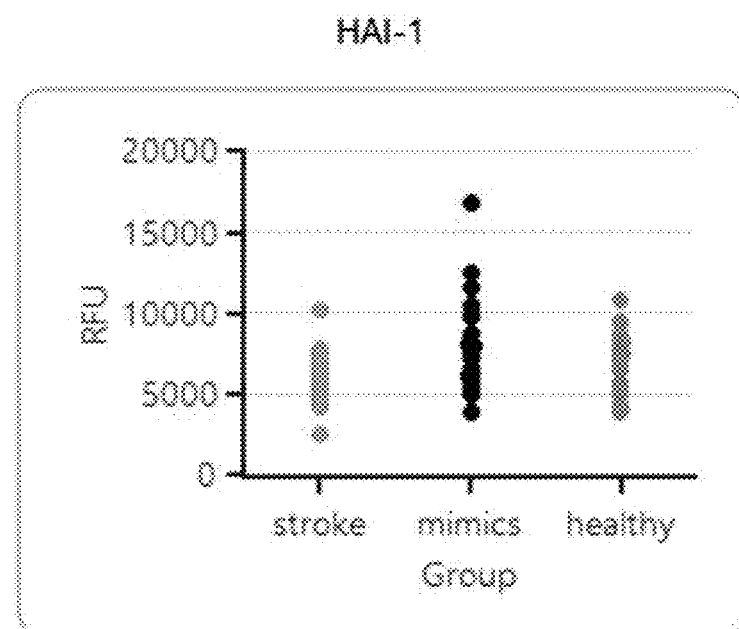
FIG. 18F is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.
Figure 18G:
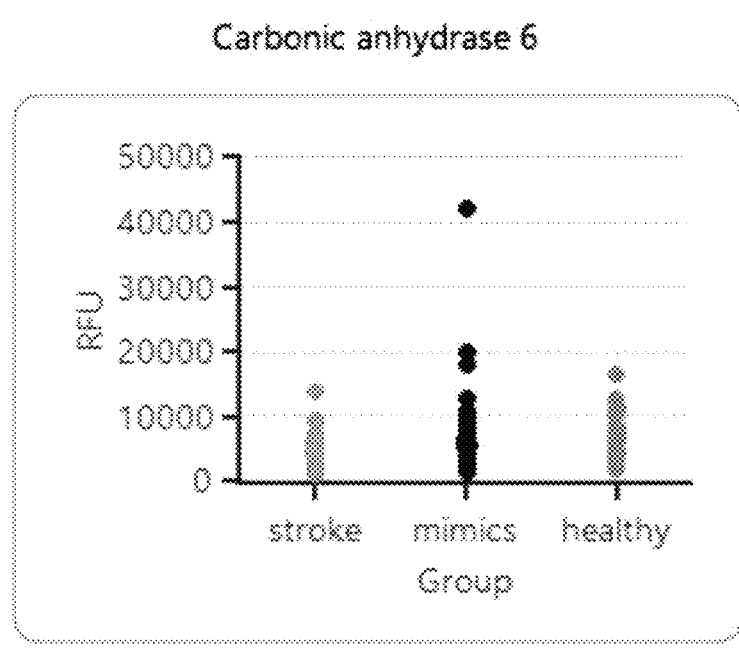
FIG. 18G is a scatter plot depicting comparisons of protein concentrations for proteins significantly different between stroke and stoke mimicking patients. Following Mann Whitney U test on 22 stroke patients and 32 stroke-mimicking patients (mimics), seven proteins were found to have a p-value $0.04<p\leq0.05$. Shown in order of decreasing statistical significance. Concentrations from healthy patient samples are shown only for comparison to the other two groups. RFU=relative fluorescent units.

Peripheral venous blood protein concentrations for stroke, stroke-mimicking, and healthy patient groups were compared using the Kruskal-Wallis test. Of the 20 proteins tested, 10 proteins from literature had a p-value less than or equal to 0.05 (Table 13). With this omnibus test, it cannot be determined which patient group is different from the others. Therefore, the Mann Whitney U test was used to examine the clinically relevant comparison of the stroke patients versus the stroke-mimicking patients. The results showed that GFAP, b-NGF, and vWF were statistically significant ($p=0.024$ 0.032, 0.017 respectively) (Table 14). When examining the scatter plots for these proteins, however, the distribution of the RFU measurements for each group overlaps, making a threshold value for calculating a clinically useful sensitivity and specificity hard to define (FIGS. 14A-14C).

TABLE 13

Comparison of previously-identified stroke biomarkers' protein concentrations between stroke, stoke mimicking, and healthy patients

| Target | p | q | H | Mean ± SD (stroke) | Mean ± SD (mimic) | Mean ± SD (healthy) |
|---|---|---|---|---|---|---|
| GFAP | 0.038 | 0.146 | 6.5 | 2168 ± 3186 | 4408 ± 19128 | 846 ± 179 |
| N-terminal pro-BNP | 0.002 | 0.022 | 12.2 | 8755 ± 11476 | 10471 ± 23455 | 2401 ± 1213 |
| BNP-32 | 0.592 | 0.781 | 1.0 | 671 ± 119 | 701 ± 198 | 682 ± 97 |
| D-dimer | 0.103 | 0.273 | 4.5 | 2587 ± 1677 | 2308 ± 988 | 1968 ± 361 |
| Caspase-3 | 0.000 | 0.002 | 19.2 | 8551 ± 3046 | 9633 ± 5729 | 5349 ± 1708 |
| MMP-9 | 0.264 | 0.492 | 2.7 | 841 ± 237 | 768 ± 388 | 783 ± 372 |
| Eotaxin | 0.205 | 0.423 | 3.2 | 1192 ± 280 | 1155 ± 397 | 1297 ± 500 |
| CDK5/p35 | 0.008 | 0.053 | 9.7 | 1875 ± 525 | 1813 ± 253 | 1585 ± 291 |
| NSE | 0.000 | 0.000 | 51.7 | 850 ± 96 | 838 ± 123 | 1563 ± 298 |
| 14-3-3 protein zeta/delta | 0.940 | 0.977 | 0.1 | 44390 ± 16274 | 44501 ± 19427 | 50468 ± 45467 |
| Cadherin-5 | 0.212 | 0.431 | 3.1 | 11254 ± 2999 | 12720 ± 4352 | 12432 ± 3111 |
| Dynactin subunit 2 | 0.000 | 0.001 | 20.9 | 2412 ± 219 | 2514 ± 387 | 2068 ± 341 |
| Myokinase, human | 0.003 | 0.026 | 11.8 | 28090 ± 16500 | 25962 ± 17567 | 14029 ± 11354 |
| sRAGE | 0.307 | 0.536 | 2.4 | 513 ± 303 | 522 ± 353 | 607 ± 312 |
| b-NGF | 0.050 | 0.177 | 6.0 | 1049 ± 263 | 909 ± 159 | 1157 ± 637 |
| MCP-1 | 0.021 | 0.099 | 7.7 | 1096 ± 221 | 1143 ± 498 | 1334 ± 470 |
| vWF | 0.032 | 0.13 | 6.9 | 60655 ± 19470 | 49096 ± 22902 | 47764 ± 19638 |
| VCAM-1 | 0.812 | 0.923 | 0.4 | 15145 ± 3896 | 18372 ± 12338 | 15798 ± 4846 |
| ERBB1 | 0.959 | 0.985 | 0.1 | 31173 ± 4815 | 31582 ± 6195 | 33382 ± 10344 |
| S100A12 | 0.092 | 0.258 | 4.8 | 3156 ± 774 | 2634 ± 1342 | 2117 ± 815 |
| PRL (prolactin) | 0.521 | 0.736 | 1.3 | 3892 ± 1200 | 3923 ± 1247 | 3516 ± 715 |

Kruskal-Wallis test statistic (H) was used to compare 22 stroke patients, 32 stroke-mimicking patients (mimic), and 26 healthy patients. Ten proteins were found statistically different between these three groups. P-value (p) less than or equal to 0.05 is considered statistically significant; q=false-discovery-rate corrected p-value. Units of measurement are relative fluorescent units (RFU). Protein abbreviations are in Table 12.

TABLE 14

Comparison of previously-identified stroke biomarkers' protein concentrations between stroke and stoke mimicking patients.

| Target | p | q | U | Mean ± SD (stroke) | Mean ± SD (mimic) |
|---|---|---|---|---|---|
| GFAP | 0.024 | 0.994 | 224 | 2168 ± 3186 | 4408 ± 19128 |
| N-terminal pro-BNP | 0.299 | 0.994 | 293 | 8755 ± 11476 | 10471 ± 23455 |
| BNP-32 | 0.771 | 0.994 | 368.5 | 671 ± 119 | 701 ± 198 |
| D-dimer | 0.597 | 0.994 | 322 | 2587 ± 1677 | 2308 ± 988 |
| Caspase-3 | 0.738 | 0.994 | 333 | 8551 ± 3046 | 9633 ± 5729 |
| MMP-9 | 0.135 | 0.994 | 267 | 841 ± 237 | 768 ± 388 |
| Eotaxin | 0.346 | 0.994 | 298.5 | 1192 ± 280 | 1155 ± 397 |
| CDK5/p35 | 0.979 | 0.994 | 353.5 | 1875 ± 525 | 1813 ± 253 |
| NSE | 0.439 | 0.994 | 308 | 850 ± 96 | 838 ± 123 |
| 14-3-3 protein | 0.725 | 0.994 | 332 | 44390 ± 16274 | 44501 ± 19427 |
| Cadherin-5 | 0.172 | 0.994 | 429.5 | 11254 ± 2999 | 12720 ± 4352 |
| Dynactin subunit 2 | 0.384 | 0.994 | 401.5 | 2412 ± 219 | 2514 ± 387 |
| Myokinase, human | 0.538 | 0.994 | 317 | 28090 ± 16500 | 25962 ± 17567 |
| sRAGE | 0.86 | 0.994 | 342 | 513 ± 302 | 522 ± 353 |
| b-NGF | 0.032 | 0.994 | 230 | 1049 ± 263 | 909 ± 159 |
| MCP-1 | 0.316 | 0.994 | 295 | 1096 ± 221 | 1143 ± 498 |
| vWF | 0.017 | 0.994 | 217 | 60655 ± 19470 | 49096 ± 22902 |
| VCAM-1 | 0.738 | 0.994 | 333 | 15145 ± 3896 | 18372 ± 12338 |
| ERBB1 | 0.944 | 0.994 | 356 | 31173 ± 4815 | 31582 ± 6195 |
| S100A12 | 0.408 | 0.994 | 305 | 3156 ± 2511 | 2634 ± 1342 |
| PRL | 0.765 | 0.994 | 369 | 3892 ± 1200 | 3923 ± 1247 |

Mann Whitney U test statistic (U) was used to compare 22 stroke patients and 32 stroke-mimicking patients (mimic). Three proteins were statistically significant between these two groups. P-value (p) less than or equal to 0.05 is considered statistically significant; q=false-discovery-rate corrected p-value. Units of measurement are relative fluorescent units (RFU).

Biomarker discovery efforts were continued using 1310 protein measurements from the SOMAscan assay to compare the stroke and stroke-mimicking groups. Mann Whitney U tests resulted in 27 proteins with p-value less than or equal to 0.05 (Table 15). There was once again a large amount of overlap in the RFU measurements of individual proteins between these two groups, making a useful threshold value to distinguish stroke patients from stroke-mimicking patients with a clinically useful sensitivity and specificity difficult to define (FIGS. 15A-15F, 16A-16G, 17A-17G, and 18A-18G).

TABLE 15

Significantly different proteins found between stroke and stoke mimicking patients.

| Target | p | q | U | mean ± SD (stroke) | mean ± SD (mimic) |
|---|---|---|---|---|---|
| SEPR | 0.003 | 0.994 | 522 | 1053 ± 222 | 1288 ± 321 |
| Dtk | 0.003 | 0.994 | 520 | 962 ± 88 | 1147 ± 565 |
| TGM3 | 0.004 | 0.994 | 190 | 3001 ± 6670 | 797 ± 1754 |
| a2-HS-Glycoprotein | 0.008 | 0.994 | 503 | 1959 ± 266 | 2153 ± 293 |
| Coagulation Factor V | 0.016 | 0.994 | 215 | 11597 ± 2520 | 10134 ± 2201 |
| vWF | 0.017 | 0.994 | 217 | 60655 ± 19470 | 49096 ± 22902 |
| C9 | 0.023 | 0.994 | 223 | 103367 ± 20402 | 90789± 18573 |
| LKHA4 | 0.023 | 0.994 | 223 | 13573 ± 4346 | 12490 ± 10691 |
| GFAP | 0.024 | 0.994 | 224 | 2168 ± 3186 | 4408± 19128 |
| MRC2 | 0.027 | 0.994 | 478 | 3830 ± 1243 | 4680 ± 1951 |
| GNS | 0.028 | 0.994 | 477 | 4147 ± 713 | 4749 ± 1400 |
| TCCR | 0.028 | 0.994 | 477 | 1582 ± 189 | 1826 ± 448 |
| Growth hormone receptor | 0.030 | 0.994 | 475 | 1237 ± 449 | 1513 ± 407 |
| b-NGF | 0.032 | 0.994 | 230 | 1049 ± 263 | 909 ± 159 |
| MK11 | 0.032 | 0.994 | 474 | 954 ± 124 | 1262 ± 910 |
| TECK | 0.035 | 0.994 | 472 | 2289 ± 1380 | 3297 ± 1980 |
| NKp30 | 0.035 | 0.994 | 472 | 648 ± 77 | 770 ± 238 |
| DSC3 | 0.036 | 0.994 | 471 | 692 ± 128 | 835 ± 379 |

TABLE 15-continued

Significantly different proteins found between stroke and stoke mimicking patients.

| Target | p | q | U | mean ± SD (stroke) | mean ± SD (mimic) |
|---|---|---|---|---|---|
| dopa decarboxylase | 0.037 | 0.994 | 471 | 241 ± 40 | 270 ± 70 |
| PlGF | 0.038 | 0.994 | 234 | 748 ± 176 | 740 ± 345 |
| RET | 0.043 | 0.994 | 467 | 2180 ± 2678 | 1970 ± 629 |
| CK-BB | 0.044 | 0.994 | 238 | 1305 ± 471 | 1190 ± 468 |
| BCL2-like 1 protein | 0.045 | 0.994 | 466 | 1191 ± 102 | 1295 ± 178 |
| DC-SIGN | 0.045 | 0.994 | 466 | 2252 ± 642 | 2476 ± 542 |
| ITI heavy chain H4 | 0.045 | 0.994 | 238 | 38815 ± 9113 | 35345 ± 8739 |
| HAI-1 | 0.047 | 0.994 | 465 | 6098 ± 1525 | 7503 ± 2642 |
| Carbonic anhydrase 6 | 0.049 | 0.994 | 464 | 5149 ± 2773 | 8351 ± 7497 |

Mann Whitney U tests were used to compare 22 stroke patients and 32 stroke-mimicking patients (mimics). Twenty-seven proteins were significantly different between these two groups. P-value (p) less than or equal to 0.05 is considered statistically significant; q=false-discovery-rate corrected p-value; U=Mann Whitney test statistic. Units of measurement are relative fluorescent units (RFU).

The lack of clinical utility from individual proteins found through univariate analyses led to an appropriate combination of proteins which could comprise a panel of stroke biomarkers. Random Forest Analysis (RFA), a machine learning algorithm, was employed to help select and evaluate proteins from the 1310-protein assay.

Figure 19:
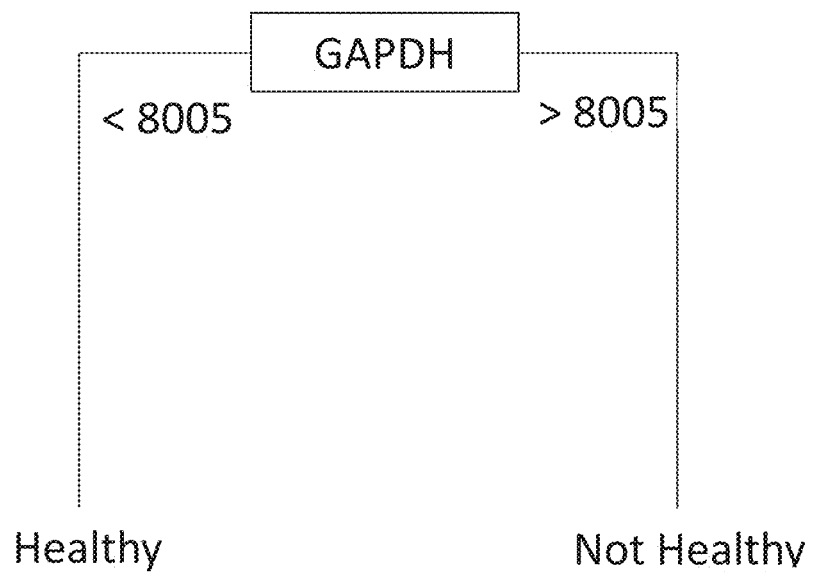
FIG. 19 depicts a decision tree for differentiating healthy patients from patients with stroke-like symptoms. Patient groups are distinguishable based on a GADPH level less than or equal to 8005 RFU, as found by random forest analysis (RFA).

To test RFA's ability to select proteins that will correctly classify patients by diagnosis, a tree first was created to distinguish the healthy individuals from all other patients (stroke and stroke-mimicking). RFA selected the best predictors which were then used to generate a single decision tree. GAPDH alone was found to be an efficient biomarker (FIG. 19). The classification table shows that GAPDH correctly classified 100 percent of the patients as healthy individuals or non-healthy individuals, with healthy individuals having a GAPDH measurement less than 8005 RFU (Table 16).

TABLE 16

Classification table for Healthy vs Not Healthy decision tree.

| | Test Results | |
|---|---|---|
| | Healthy | Not Healthy |
| Healthy Patients | 26 | 0 |
| Unhealthy Patients | 0 | 54 |

Eighty patients were tested using the RFA-generated decision tree to differentiate healthy patients from patients with stroke-like symptoms. GAPDH correctly classified 100% of the patients, giving both a sensitivity and specificity equal to 100%.

Figure 20:
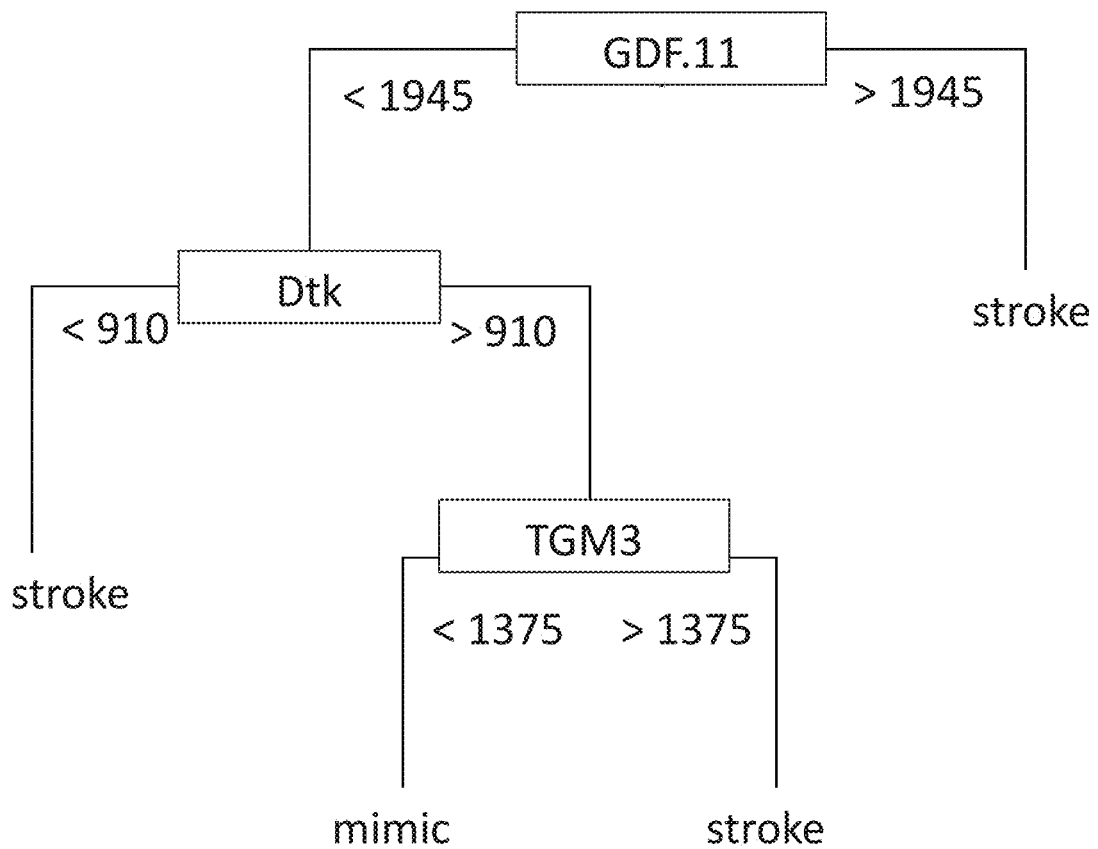
FIG. 20 depicts a decision tree for differentiating stroke patients from stroke-mimicking patients. RFA was able to distinguish these two groups based on the serum concentrations of GDF-11, Dtk, and TGM3 proteins.

RFA then was employed to classify stroke and stroke-mimicking patients. This yielded three proteins selected to define a decision tree: GDF-11, Dtk, and TGM3 (FIG. 20). Of the 22 stroke patients, 21 were correctly classified as stroke, and of the 32 stroke-mimicking patients, 28 were correctly classified as mimics. The panel demonstrated a 95.5% sensitivity and 87.5% specificity (Table 17). The positive likelihood ratio (LR+) was 7.6 and the negative likelihood ratio (LR−) was 0.05.

Figure 21:
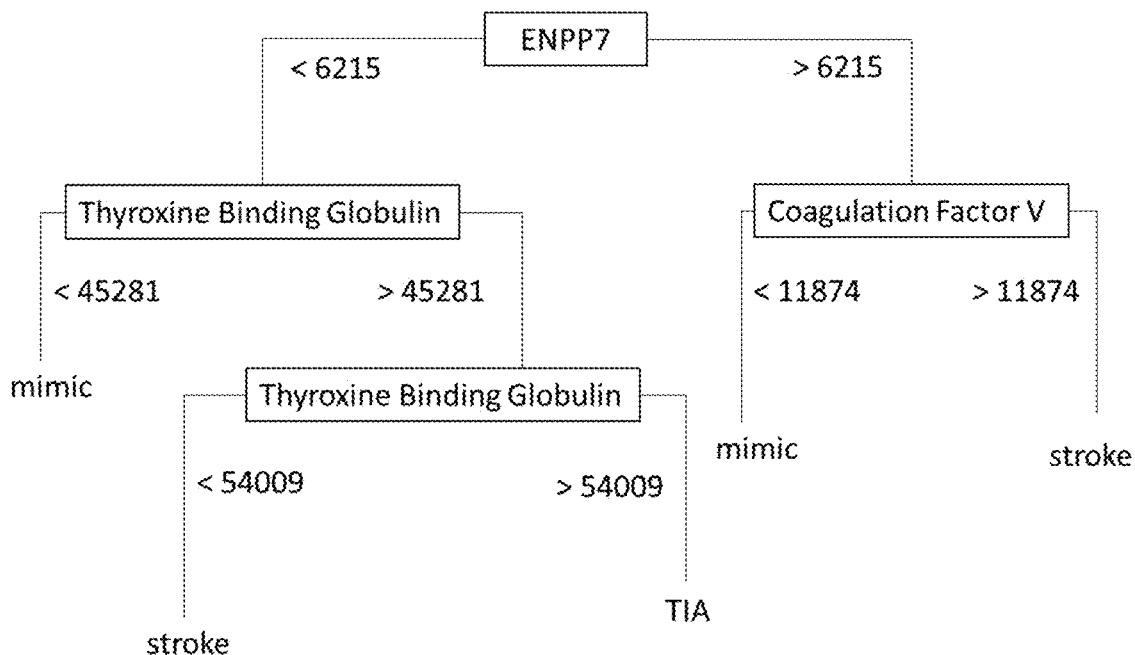
FIG. 21 depicts a decision tree for differentiating stroke, non-TIA stroke-mimicking patients, and TIA patients. RFA was able to distinguish these three groups based on the serum concentrations of ENPP7, TBG, and Coag Factor V proteins.

In the previous analysis, the stroke-mimicking group included patients diagnosed with TIA. TIA patients are very similar to and difficult to distinguish from stroke patients because they exhibit very similar symptoms due to shared pathologies; however, TIA is self-resolving and does not result in the tissue infarction that characterizes stroke pathology. TIA may therefore be better categorized as a separate diagnosis group from both stroke groups and stroke-mimicking groups. When stroke, stroke-mimicking, and TIA patients were analyzed as separate groups by RFA, three proteins were selected as effective discriminators of these patients and were used to generate a decision tree for a biomarker panel: ENPP7, Thyroxine Binding Globulin, and Coagulation Factor V (FIG. 21. When evaluated by this decision tree, 17 of 22 stroke patients were correctly classified as stroke, and 29 of 32 non-stroke patients were correctly classified as either stroke-mimicking or TIA. The panel demonstrated a 77.2% sensitivity and 90% specificity (LR+=7.7 and LR−=0.25) for identifying stroke patients (Table 18). Interestingly, 23 of the 23 non-TIA stroke-mimicking patients were correctly classified as such, giving a 100% sensitivity for a non-stroke, non-TIA diagnosis.

TABLE 17

Classification table for Stroke vs Mimic decision tree.

| | Test Results | |
|---|---|---|
| | Stroke | Mimic |
| Stroke Patients | 21 | 1 |
| Mimic Patients | 4 | 28 |

Fifty-four patients were tested using the RFA-generated decision tree to differentiate stroke patients from stroke-mimicking patients (Mimic). GDF-11, Dtk, and TGM3 proteins correctly classified 21 of 22 stroke patients and 28 of 32 stroke mimicking patients, giving a 95.5% sensitivity and 87.5% specificity for stroke diagnosis.

TABLE 18

Classification table for Stroke vs Mimic vs TIA decision tree.

| | Test Results | | |
|---|---|---|---|
| | Stroke | Mimic | TIA |
| Stroke Patients | 17 | 4 | 1 |
| Mimic Patients | 0 | 23 | 0 |
| TIA Patients | 3 | 2 | 4 |

Fifty-four patients were tested using the RFA-generated decision tree to differentiate stroke patients from non-TIA stroke-mimicking patients (Mimic) and TIA patients. ENPP7, TBG, and Coag Factor V proteins correctly classified 17 of 22 stroke patients, 23 of 23 non-TIA stroke-mimicking patients, and 4 of 9 TIA patients. For stroke diagnosis, this gives a 77.2% sensitivity and 90% specificity. For non-TIA non-stroke diagnosis, the sensitivity is 100% and the specificity is 81%.

Figure 22:
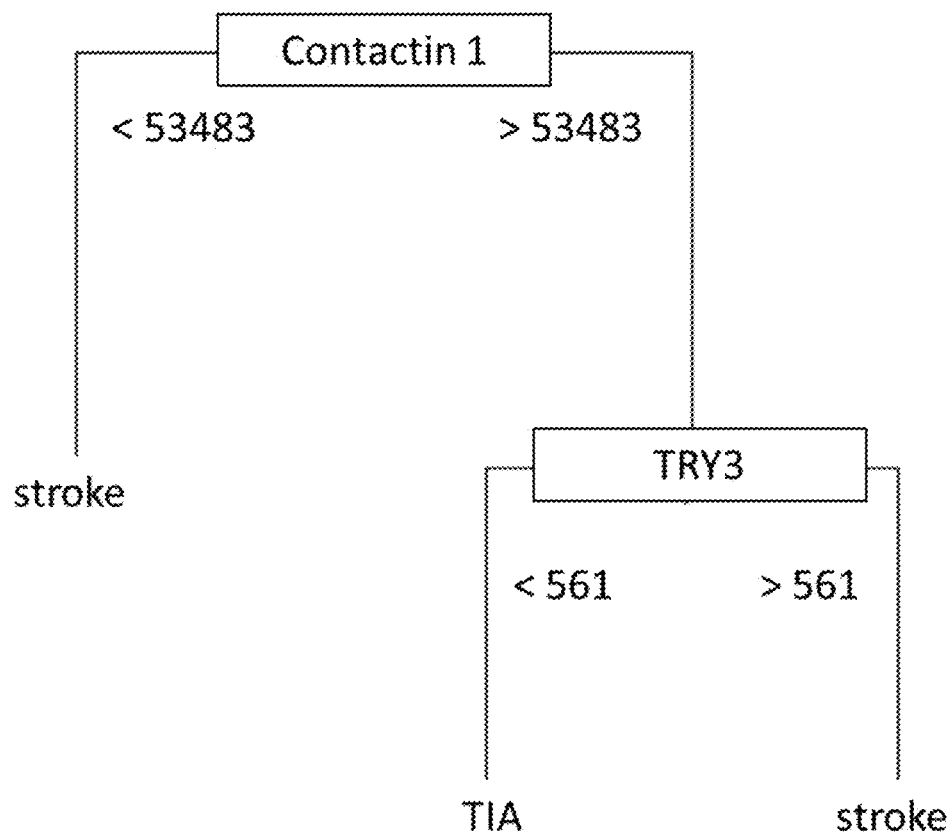
FIG. 22 depicts a decision tree for differentiating stroke and TIA patients. RFA was able to distinguish these two groups based on the serum concentrations of Contactin 1 and TRY3 proteins.

When comparing just the stroke and TIA patients, RFA selected two proteins for a biomarker panel: contactin-1 and TRY3 (FIG. 22). When patients were evaluated by this decision tree, 22 of 22 stroke patients were correctly classified as stroke and 7 of 9 TIA patients were correctly classified as TIA, giving a 100% sensitivity and 77.8% specificity (LR+=4.5 and LR-=0) for stroke diagnosis (Table 19).

TABLE 19

Classification table for Stroke vs TIA decision tree.

| | Test Results | |
|---|---|---|
| | Stroke | TIA |
| Stroke Patients | 22 | 0 |
| TIA Patients | 2 | 7 |

Thirty-one patients were tested using the RFA-generated decision tree to differentiate stroke patients from TIA patients. Contactin 1 and TRY3 proteins correctly classified all 22 stroke patients and 7 of 9 TIA patients. For stroke diagnosis, this gives a 100% sensitivity and 78% specificity.

Of the 19 previously-identified biomarkers from published literature, GFAP, b-NGF, and vWF were found to be statistically different between the stroke and stroke-mimicking groups; however, the scatter plots suggested a sensitivity and specificity of low clinical value. This result agrees with those found in the published literature, as no single protein has been deemed sufficient for stroke diagnosis to date. For example, vWF has been demonstrated to have a 66% sensitivity and 73.8% specificity. Likewise, GFAP was demonstrated to have a c-statistic of 0.556, little better than random chance at predicting stroke diagnosis (0.50), when compared with patients presenting with vertigo.

Univariate analyses for new biomarker candidates identified 27 proteins with statistical differences between stroke and mimicking patients. However, it is unlikely that these proteins—individually—would make valuable biomarkers, as the large overlap seen in the serum measurements would lead to sensitivity and specificity values that are clinically unacceptable. Indeed, it has been previously stated that while identifying a single biomarker would be ideal, this outcome is also improbable due to the diversity of stroke pathophysiology. Therefore, developing a biomarker panel is a more realistic goal than finding the "troponin of stroke".

A random forest analysis found 3 combinations of proteins that do well to differentiate stroke from non-TIA stroke mimicking patients and TIA patients. The first panel separated stroke from the combined mimics and TIA with relatively high diagnostic accuracy. The proteins GDF-11, Dtk, and TGM3 correctly classified 21 of 22 stroke patients. Growth differentiation factor 11 (GDF-11) is an extracellular protein that functions as a growth factor and a cytokine. Serum levels of this protein have been shown to decrease with age in animal models. Furthermore, increased levels are associated with lower risk of cardiovascular events in human. Tyrosine-protein kinase receptor (Dtk or TYRO3) is a cell membrane protein involved in signal transduction. It is found abundantly in the brain and plays a role in neuron protection following excitotoxic injury. Studies have shown it mediates vasculoprotection via Protein S and is associated with a decreased risk of carotid atherosclerosis. Transglutaminase E (TGM3) is an enzyme that helps form cross-links between glutamine and lysine residues in proteins. This protein has not been previously associated with stroke or cardiovascular disease.

The second panel classified stroke from mimics and TIA separately. The proteins ENPP7, Thyroxine Binding Globulin, and Coagulation Factor V correctly classified all mimics, and 17 of the 22 strokes. Ectonucleotide pyrophosphatase/phosphodiesterase family member 7 (ENPP7) is an enzyme that converts sphingomyelin to ceramide. It has been associated with human carotid plaques, and gene expression was found to be significantly different between asymptomatic donors versus donors with a recent stroke. Throxine Binding Globulin (TBG or SERPIN A7) is a serum protein expressed by the liver. Its role is to transport thyroid hormones. Although TBG has not been directly implicated in stroke, thyroid disorders have been associated with increased risk of stroke. The stroke and TIA patients in this study had higher averaged serum levels of TBG than other non-stroke patients. Perhaps, then, this protein is a risk factor. Coagulation Factor V is involved in blood coagulation, acting as an important cofactor for the activation of prothrombin to thrombin. A genetic variant, Factor V Leiden, was found to be associated with ischemic stroke, but it is unknown whether the patients in this study carried this marker.

The third panel of protein biomarkers classified stroke from TIA patients. The proteins contactin-1 and TRY3 correctly classified all 22 stroke patients and 7 of the 9 TIA patients. Contactin-1 (also known as glycoprotein gp135 or neural cell surface protein F3) is a plasma membrane protein expressed in the brain and other tissues. It aids in the signaling between axons and myelinating glial cells and is important during nervous system development. No literature could be found that associates this protein with ischemic stroke or TIA. Trypsin 3 (TRY3), also known as brain trypsinogen is an extracellular serine protease expressed in the pancreas and the brain. Its main function is the degradation of trypsin inhibitors, but it is also involved in endothelial cell migration, neutrophil degranulation, and zymogen activation. This protein has not been previously associated with stroke or cardiovascular disease.

Proteins from any one panel were not repeated in the other panels. The panel that includes TIA patients in the stroke-mimicking group (FIG. 20) and the panel that separates TIA from non-TIA stroke-mimicking patients (FIG. 21) do not have any proteins in common despite being compared to the same stroke patient group. This could be because there are physiological differences between stroke-mimicking and TIA patients and/or pathophysiological similarities between stroke and TIA patients. Ischemic stroke occurs when a cerebral artery is blocked, causing a loss of blood supply and ultimately infarction. During a TIA, there is a temporary disruption of blood flow, but this does not cause an infarction. The etiologies of the non-TIA stroke-mimicking group are diverse and include migraine, seizure, dementia, and metabolic disorders. While the symptoms are very similar, the pathologies may not be. For example, migraine is thought to be associated with cortical spreading depressing and inflammation of the dura mater.

The results suggest that when stroke-mimicking and TIA patients are treated as a combined group or divided into separate groups, different proteins are necessary to correctly classify them from stroke.

The diagnostic accuracies of the protein panels were on par with published stroke biomarker panels. Sensitivities from published studies ranged from 17% to 92% and specificities ranged from 37% to 98% (Table 1). The stroke vs mimic panel according to an embodiment of the innovation had a 95.5% sensitivity, which improves upon these biomarker panels. The panel with the highest diagnostic accuracy included BNGF, MCP-1, MMP-9, S100B, and vWF and demonstrated a 92% sensitivity when comparing stroke to healthy controls. Another panel had a very low sensitivity but a very high specificity. This panel included Caspase-3, Chimerin, D-dimer, MMP-9, Secretagogin, and sRAGE and demonstrated a 98% specificity when comparing stroke to mimic patients. While the present panels far outweighed the 17% sensitivity, they did not improve upon this specificity.

The finding that the present panel achieved a high sensitivity and specificity speaks to the viability of panels over individual biomarkers. Consideration of the univariate analysis results for the proteins from the first panel, the proteins Dtk, GDF-11, and TGM3 had a p-value of 0.0031, 0.4923, and 0.0043, respectively. While Dtk and TGM3 were in the top three results, GDF-11 was not statistically different between the stroke and stroke mimicking groups. Nonetheless it was considered a strong predictor for stroke diagnosis using random forest analysis.

A number of proteins were found that were significantly different between stroke and stroke-mimicking patient groups; however, no protein was identified as a promising single diagnostic biomarker. Random Forest Analysis may have identified a clinically useful combination of proteins to distinguish stroke patients from non-TIA stroke-mimicking patients and TIA patients.

Throughout the specification, proteins have been described by name, by abbreviation, or both. Table 20 (below) provides the protein name for the protein abbreviation used in the specification. It is to be understood that Applicant is not asserting that this list includes all proteins identified herein. In addition, it is noted that some proteins may be referred to by more than one name in the scientific literature and the use of one name over does not impact the identifiability of the protein. The proteins included herein are known in the art and are identifiable by either the protein abbreviation or the protein name regardless of whether the protein appears in Table 20.

TABLE 20

Partial list of corresponding protein abbreviations and protein names

| PROTEIN ABBREVIATION | PROTEIN NAME |
|---|---|
| Activin A | Inhibin beta A chain |
| Activin AB | Inhibin beta A chain/B chain heterodimer |
| AMNLS | Protein amnionless/Amnion Associated Trans-membrane Protein |
| AMPK a1b1g1 | 5'-AMP-activated protein kinase catalytic subunit alpha-1 |
| AMPM2 | Methionine aminopeptidase 2 |
| BMP-14 | Growth/differentiation factor 5 (Bone morphogenetic protein 14) |
| BMX | cytoplasmic tyrosine-protein kinase BMX |
| b-NGF | beta-nerve growth factor |
| C3b | Complement clevage product C3 |
| C5 | Complement component C5 |
| C9 | Complement component C9 |
| CAMK2B | Calcium/calmodulin-dependent protein kinase type II subunit beta |
| CAMK2D | Calcium-calmodulin-dependent kinase type II subunit delta |
| CD70 | CD70 antigen |
| CDK5/p35 | Cyclin-dependent-like kinase 5/Cyclin-dependent kinase 5 activator 1 |
| cIAP-2 | Baculoviral IAP repeat-containing protein 3 (Cellular inhibitor of apoptosis 2) |
| CK-BB | Creatine kinase B-type |
| CLC7A | C-Type Lectin Domain Containing 7A |
| CLF-1/CLC Complex | Cytokin receptor-like factor 1/Cardiotrophin-like cytokine factor 1 Complex |
| COLEC12 | Collectin-12 |
| CRK | adapter molecule crk |
| DC-SIGN | CD209 antigen (Dendritic cell-specific ICAM-3 grabbing non-integrin 1 |
| DSC3 | Desmocollin-3 |
| Dtk | Tyrosine-protein kinase receptor TYRO3 |

TABLE 20-continued

Partial list of corresponding protein abbreviations and protein names

| PROTEIN ABBREVIATION | PROTEIN NAME |
|---|---|
| eIF-5 | Eukaryotic translation initiation factor 5 |
| ENPP7 | Ectonucleotide pyrophosphatase/phosphodiesterase family member 7 |
| EPHA3 | Ephrin type-A receptor 3 |
| ER | Estrogen receptor |
| ERP29 | Endoplasmic reticulum resident protein 29 |
| FABPL | Fatty acid-binding protein, liver |
| FGF23 | Fibroblast growth factor 23 |
| FGFR-2 | Fibroblast-growth factor receptor 2 |
| Fibrinogen g-chain dimer | Fibrinogen gamma chain |
| GAPDH | Glyceraldehyde-3-phosphate dehydrogenase |
| GDF.11 | Growth differentiation factor 11 |
| GDF2 | Growth/differentiation factor 2 |
| GFAP | Glial fibrillary acidic protein |
| GNS | N-acetylglucosamine-6-sulfatase |
| GSK-3 alpha/beta | Glycogen synthase kinase-3 alpha/beta |
| H31 | Histone H3.1 |
| HAI-1 | Kunitz-type protease inhibitor 1 (Hepatocyte growth factor activator inhibitor type 1) |
| HB-EGF | Proheparin-binding EGF-like growth factor |
| HGH | Human growth hormone (somatotropin) |
| hnRNP K | Heterogeneous nuclear ribonucleoprotein K |
| HTRA2 | Serine protease HTRA2, mitochondrial (High temperature requirement protein A2) |
| iC3b | (inactivated C3b) |
| IL-17 | Interleukin-17 |
| IL-18 BPa | Interleukin-18-binding protein |
| IL-1F8 | Interleukin-36 beta |
| IL-7 Ra | Interleukin-7 receptor subunit alpha |
| KI2L4 | Killer cell immunoglobulin-like receptor 2DL4 |
| KI3L2 | Killer cell immunoglobulin-like receptor 3DL2 |
| KLRF1 | Killer cell lectin-like receptor subfamily F member 1 |
| KYNU | Kynureninase |
| LKHA4 | Leukotriene A-4 hydrolase |
| LRRT1 | Leucine-rich repeat transmembrane neuronal protein-1 |
| M2-PK | Pyruvate kinase isosnzyme PKM |
| MCP-1 | C-C motif chemokine 2 |
| MK11 | Mitogen-activated protein kinase 11 |
| MMP-1 | Interstitial collagenase (Matrix metalloproteinase-1) |
| MMP-13 | Collagenase 3 precursor/Matrix metalloproteinase-13 |
| MMP-17 | Matrix metalloproteinase-17 |
| MMP-7 | Matrilysin/matrix metalloproteinase-7 |
| MO2R1 | Cell surface glycoprotein CD200 receptor 1 |
| MRC2 | C-type mannose receptor 2 |
| NANOG | Homeobox protein NANOG |
| NKp30 | Natural cytotoxicity triggering receptor 3 |
| NR1D1 | Nuclear receptor subfamily 1 group D member 1 |
| NSE | Gamma-enolase (Neuron-specific enolase) |
| NSF1C | NSFL1 cofactor p47 |
| N-terminal pro-BNP | (Natriuretic peptides B) |
| OAS1 | 2'-5'-oligoadenylate synthase 1 |
| PDGFRA | Platelet-derived growth factor receptor alpha |
| PIGF | Phosphatidylinositol-glycan biosynthesis class F protein |
| PPID | Peptidyl-prolyl cis-trans isomerase D |
| prostatic binding protein | Phosphatidylethanolamine-binding protein 1 |
| PSME3 | Proteasome activator complex subunit 3 |
| RANTES | (cleaved C-C motif chemokine 5) |
| RASA1 | Ras GTPase-activating protein 1 |
| RET | Proto-oncogene tyrosine-protein kinase receptor Ret |
| SEPR | Prolyl endopeptidase FAP (Seprase) |
| SHP-2 | Tyrosine-protein phosphatase non-receptor type 11 |
| sICAM-5 | soluble Intercellular adhesion molecule 5 |
| Spot 44 | Haptoglobin |
| SREC-II | Scavenger receptor class F member 2 |
| tau | Microtubule-associated protein tau |

TABLE 20-continued

Partial list of corresponding protein abbreviations and protein names

| PROTEIN ABBREVIATION | PROTEIN NAME |
| --- | --- |
| TCCR | Type I T-cell cytokine receptor OR Interleukin-27 receptor subunit alpha |
| TECK | C-C motif chemokine 25 |
| TFPI | Tissue factor pathway inhibitor |
| TGF-b3 | Transforming growth factor beta-3 |
| TGM3 | Protein-glutamine gamma-glutamyltransferase E (Transglutaminase-3) |
| TRY3 | Trypsin-3 |
| TYK2 | Non-receptor tyrosine-protein kinase TYK2 |
| UB2G2 | Ubiquitin-conjugating enzyme E2 G2 |
| Ubiquitin + 1 | Ubiquitin + 1, truncated mutation for UbB |
| UFC1 | Ubiquitin-fold modifier-conjugating enzyme 1 |
| VEGF sR2 | Vascular endothelial growth factor receptor 3 |
| VEGF sR3 | Vascular endothelial growth factor receptor 3 |
| vWF | von Willebrand factor |
| WNT7A | Protein Wnt-7a |

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method for identifying and treating a patient suffering from a stroke comprising: (a) obtaining a sample of blood from the patient; (b) detecting whether the sample of blood includes two or more protein biomarkers constituting a first biomarker panel and the two or more protein biomarkers of the first biomarker panel include at least contactin-1 and TRY3, wherein the presence of the two or more protein biomarkers of the first biomarker panel confirms the stroke; and (c) treating the patient, treating the patient comprising, upon determining that the patient is suffering from the stroke, treating the patient with tissue plasminogen activator or mechanical thrombectomy.

2. The method according to claim 1, wherein the sample of blood is venous blood.

3. The method according to claim 1, wherein detecting the two or more protein biomarkers of the first biomarker panel is selected from one or a combination of immunoassay, protein microarray, western blotting, mass spectroscopy, and flow-cytometry analytics.

4. The method according to claim 3, wherein the detecting includes contacting the sample of blood or an isolate from the sample of blood with at least one antibody that is specific for each of the two or more protein biomarkers of the first biomarker panel.

5. The method according to claim 1, wherein the detecting further includes detecting two or more additional protein biomarkers constituting a second biomarker panel; the two or more additional protein biomarkers are selected from the group consisting of Activin A, Activin AB, AMNLS, AMPK a1b1g1, AMPM2, BMP-14, BMX, b-NGF, C3b, C5, C9, CAMK2B, CAMK2D, CD70, CDK5/p35, cIAP-2, CK-BB, CLC7A, CLF-1/CLC Complex, COLEC12, CRK, DC-SIGN, DSC3, Dtk, eIF-5, ENPP7, EPHA3, ER, ERP29, FABPL, FGF23, FGFR-2, Fibrinogen g-chain dimer, GAPDH, GDF-11, GDF2, GNS, GSK-3 alpha/beta, H31, HAI-1, HB-EGF, HGH, hnRNP K, HTRA2, iC3b, IL-18 BPa, IL-1F8, IL-7 Ra, KI2L4, KI3L2, KLRF1, KYNU, LKHA4, LRRT1, M2-PK, MK11, MMP-1, MMP-13, MMP-17, MMP-7, MO2R1, MRC2, NANOG, NKp30, NR1D1, NSE, NSF1C, N-terminal pro-BNP, OAS1, PDG-FRA, PIGF, PPID, prostatic binding protein, PSME3, RASA1, RET, SEPR, SHP-2, sICAM-5, Spot 44, SREC-II, tau, TCCR, TECK, TFPI, TGF-b3, TGM3, TYK2, UB2G2, Ubiquitin+1, UFC1, VEGF sR2, VEGF sR3, vWF, WNT7A, Thyroxine Binding Globulin (TGB), Coagulation Factor V, and combinations thereof; and the two or more additional protein biomarkers are distinct from the two or more protein biomarkers of the first biomarker panel, and wherein the detected levels of each of the two or more additional protein biomarkers constituting the second biomarker panel is indicative of the patient suffering from the stroke.

6. The method according to claim 1, wherein the patient presents with the symptoms of transient ischemic attack.

7. The method according to claim 5, wherein the second biomarker panel includes GDF-11, Dtk, and TGM3 or ENPP7, Thyroxine Binding Globulin (TGB), and Coagulation Factor V.

8. The method according to claim 5, wherein the detecting further includes detecting two or more further additional protein biomarkers constituting a third biomarker panel, and wherein the detected levels of each of the two or more additional protein biomarkers constituting the third biomarker panel is indicative of the patient suffering from the stroke.

9. The method according to claim 8, wherein the first biomarker panel includes contactin-1 and TRY3, the second biomarker panel includes GDF-11, Dtk, and TGM3, and the third biomarker panel includes ENPP7, Thyroxine Binding Globulin (TGB), and Coagulation Factor V.

* * * * *